(12) United States Patent
Linde et al.

(10) Patent No.: US 12,036,410 B2
(45) Date of Patent: Jul. 16, 2024

(54) MULTI-TARGET ADAPTIVE NEUROSTIMULATION THERAPY CONTROL

(71) Applicant: Medtronic, Inc., Minneapolis, MN (US)

(72) Inventors: David E. Linde, Bremerton, WA (US); Benjamin P. Isaacson, Centerville, MN (US); Nicholas D. Buse, New Brighton, MN (US); Duane L. Bourget, Andover, MN (US); Robert S. Raike, Minneapolis, MN (US); Jonathon E. Giftakis, Maple Grove, MN (US); Caleb C. Zarns, Minneapolis, MN (US); Thomas L. Chouinard, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 286 days.

(21) Appl. No.: 17/062,213

(22) Filed: Oct. 2, 2020

(65) Prior Publication Data

US 2021/0121697 A1   Apr. 29, 2021

Related U.S. Application Data

(60) Provisional application No. 62/925,069, filed on Oct. 23, 2019.

(51) Int. Cl.
*A61N 1/36* (2006.01)
*A61N 1/05* (2006.01)

(52) U.S. Cl.
CPC ....... *A61N 1/36139* (2013.01); *A61N 1/0534* (2013.01); *A61N 1/36067* (2013.01); *A61N 1/36171* (2013.01); *A61N 1/36175* (2013.01); *A61N 1/36192* (2013.01); *A61N 1/36071* (2013.01)

(58) Field of Classification Search
CPC ............ A61N 1/36139; A61N 1/36067; A61N 1/36135; A61N 1/3615; A61N 1/36171; A61N 1/0534
See application file for complete search history.

(56) References Cited

U.S. PATENT DOCUMENTS 5,683,422 A  * 11/1997  Rise .................. A61N 1/36171
                                                                 607/2
9,079,039 B2    7/2015  Carlson et al.
9,155,885 B2 * 10/2015  Wei ...................... A61N 1/3614
(Continued)

OTHER PUBLICATIONS

International Search Report and Written Opinion of International Application No. PCT/US2020/056666, dated Feb. 3, 2021, 18 pp.
(Continued)

*Primary Examiner* — William J Levicky
(74) *Attorney, Agent, or Firm* — Shumaker & Sieffert, P.A.

(57) ABSTRACT

A medical device or system of medical devices can be configured to detect an indicator of a symptom in a patient; in response to detecting the indicator of the symptom in the patient, deliver to the patient a first stimulation therapy; and in response to determining that the indicator of the symptom has been present for more than a threshold amount of time after beginning to deliver the first stimulation therapy a second stimulation therapy different than the first stimulation therapy.

35 Claims, 37 Drawing Sheets

(56) References Cited

U.S. PATENT DOCUMENTS

| | | | |
|---|---|---|---|
| 2011/0160796 A1* | 6/2011 | Lane | A61N 1/36082 |
| | | | 607/45 |
| 2013/0218232 A1* | 8/2013 | Giftakis | A61N 1/3615 |
| | | | 607/45 |
| 2013/0331906 A1 | 12/2013 | Krueger et al. | |
| 2014/0163627 A1 | 6/2014 | Starr et al. | |
| 2015/0012057 A1 | 1/2015 | Carlson et al. | |
| 2019/0282821 A1* | 9/2019 | Masuda | A61N 1/3621 |
| 2019/0290900 A1* | 9/2019 | Esteller | A61N 1/0551 |

OTHER PUBLICATIONS

Hell et al., "Deep Brain Stimulation Programming 2.0: Future Perspectives for Target Identification and Adaptive Closed Loop Stimulation," Frontiers in Neurology, vol. 10, Apr. 3, 2019, 11 pp.

* cited by examiner

|  |  | LD1 | | |
|---|---|---|---|---|
|  |  | Out < LB | LB < Out < UB | Out > UB |
| LD2 | Out < UB | ⬇<br>State0<br>⇩ | Hold<br>State1<br>⇩ | ⬆<br>State2<br>⇩ |
|  | LB > Out < UB | ⬇<br>State3<br>Hold | Hold<br>State4<br>Hold | ⬆<br>State5<br>Hold |
|  | Out > UB | ⬇<br>State6<br>⇧ | Hold<br>State7<br>⇧ | ⬆<br>State8<br>⇧ |

FIG. 11A

State Machine :
Switches between 9 states based on LD 1 & LD2 Output

|  |  | LD1 | | |
|---|---|---|---|---|
|  |  | Low | In Range | High |
| LD2 | Low | P1 Targets<br>P2 Targets<br>P3 Targets<br>P4 Targets | P1 Targets<br>P2 Targets<br>P3 Targets<br>P4 Targets | P1 Targets<br>P2 Targets<br>P3 Targets<br>P4 Targets |
|  | In Range | P1 Targets<br>P2 Targets<br>P3 Targets<br>P4 Targets | P1 Targets<br>P2 Targets<br>P3 Targets<br>P4 Targets | P1 Targets<br>P2 Targets<br>P3 Targets<br>P4 Targets |
|  | High | P1 Targets<br>P2 Targets<br>P3 Targets<br>P4 Targets | P1 Targets<br>P2 Targets<br>P3 Targets<br>P4 Targets | P1 Targets<br>P2 Targets<br>P3 Targets<br>P4 Targets |

FIG. 14A

State 0

| P1 Targets :<br>Amp: 5 mA<br>Rise: 0.1 mA/s<br>Fall: 1 mA/s | P2 Targets :<br>Amp: 4 mA<br>Rise: 0.2 mA/s<br>Fall: 3 ma/s |
|---|---|
| P3 Targets :<br>Amp: 7 mA<br>Rise: 0.4 mA/s<br>Fall: 2 mA/s | P4 Targets :<br>Amp: 3 mA<br>Rise: 0.3 mA/s<br>Fall: 4 mA/s |

Rate: 130Hz

State 1

| P1 Targets :<br>Amp: 2 mA<br>Rise: 0.1 mA/s<br>Fall: 1 ma/s | P2 Targets :<br>Amp: HOLD<br>Rise: 0.2 mA/s<br>Fall: 3 ma/s |
|---|---|
| P3 Targets :<br>Amp: HOLD<br>Rise: 0.4 mA/s<br>Fall: 2 ma/s | P4 Targets :<br>Amp: 1 mA<br>Rise: 0.3 mA/s<br>Fall: 4 mA/s |

Rate: 150Hz

State 2
...

State 3

| P1 Targets :<br>Amp: 6 mA<br>Rise: 0.1 mA/s<br>Fall: 1 mA/s | P2 Targets :<br>Amp: 5 mA<br>Rise: 0.2 mA/s<br>Fall: 3 mA/s |
|---|---|
| P3 Targets :<br>Amp: 3 mA<br>Rise: 0.4 mA/s<br>Fall: 2 mA/s | P4 Targets :<br>Amp: HOLD<br>Rise: 0.3 mA/s<br>Fall: 4 mA/s |

Rate: 90Hz

State 4

| P1 Targets :<br>Amp: HOLD<br>Rise: 0.1 mA/s<br>Fall: 1 ma/s | P2 Targets :<br>Amp: 2 mA<br>Rise: 0.2 mA/s<br>Fall: 3 ma/s |
|---|---|
| P3 Targets :<br>Amp: 5 mA<br>Rise: 0.4 mA/s<br>Fall: 2 mA/s | P4 Targets :<br>Amp: 6 mA<br>Rise: 0.3 mA/s<br>Fall: 4 mA/s |

Rate: HOLD

State 5
...

State 6
...

State 7
...

State 8
...

FIG. 14B

P1:
Amp: 0 / 8 mA
Rise: 0.3 mA/s
Fall: 2 ma/s

P2:
Amp: 2 / 5 mA
Rise: 0.5 mA/s
Fall: 5 ma/s

P3:
Amp: 3 / 7 mA
Rise: 0.6 mA/s
Fall: 4 ma/s

P4:
Amp: 1 / 6 mA
Rise: 0.4 mA/s
Fall: 6 ma/s

Freq: 50 / 150 Hz

FIG. 14C

Closed Loop State Diagram with Control Policy Actions

| | Linear Detector 1– Detect Event Biomarker<br>Control therapy delivery to Stimulation Mode 1<br>Example<br>Frequency = 100Hz<br>Onset and Term = low (Fast response) | |
|---|---|---|
| | Biomarker Not Detected | Biomarker Detected |
| Linear Detector 2– detect presence of Stimulation Mode 1<br>Control therapy delivery to Stimulation Mode 2<br>Example<br>Frequency = 130Hz<br>Onset = 5 secs<br>Termination = 13 secs | | |
| Stimulation Target 1 Not Detected | Stimulation Mode 1 = Off<br>Stimulation Mode 2 = Off<br>State 1 | Stimulation Mode 1 = On<br>Stimulation Mode 2 = Off<br>State 2 |
| Stimulation Target 1 Detected | Stimulation Mode 1 = Off<br>Stimulation Mode 2 = On<br>State 3 | Stimulation Mode 1 = Off<br>Stimulation Mode 2 = On<br>State 4 |

FIG. 17

Closed Loop State Diagram with Control Policy Actions - Biomarker Not Detected

| | | Biomarker Not Detected | Biomarker Detected |
|---|---|---|---|
| | Linear Detector 1 – Detect Event Biomarker<br>Control therapy delivery to Stimulation Mode 1<br>Example<br>Frequency = 100Hz<br>Onset and Term = low (Fast response) | | |
| Linear Detector 2 – detect presence of Stimulation Mode 1<br>Control therapy delivery to Stimulation Mode 2<br>Example<br>Frequency = 130Hz<br>Onset = 5 secs<br>Termination = 13 secs | Stimulation Target 1 Not Detected | Stimulation Mode 1 = Off<br>Stimulation Mode 2 = Off<br><u>162</u>  State 1 | Stimulation Mode 1 = On<br>Stimulation Mode 2 = Off<br><u>164</u>  State 2 |
| | Stimulation Target 1 Detected | Stimulation Mode 1 = Off<br>Stimulation Mode 2 = On<br><u>166</u>  State 3 | Stimulation Mode 1 = Off<br>Stimulation Mode 2 = On<br><u>168</u>  State 4 |

FIG. 18

Closed Loop State Diagram with Control Policy Actions

| | | Biomarker Not Detected | Biomarker Detected |
|---|---|---|---|
| | Linear Detector 1 -- Detect Event Biomarker<br>Control therapy delivery to Stimulation Mode 1<br>Example<br>Frequency = 100Hz<br>Onset and Term = low (Fast response) | | |
| Linear Detector 2 -- detect presence of Stimulation Mode 1<br>Control therapy delivery to Stimulation Mode 2<br>Example<br>Frequency = 130Hz<br>Onset = 5 secs<br>Termination = 13 secs | Stimulation Target 1 Not Detected | Stimulation Mode 1 = Off<br>Stimulation Mode 2 = Off<br><u>162</u><br>State 1 | Stimulation Mode 1 = On<br>Stimulation Mode 2 = Off<br><u>164</u><br>State 2 |
| | Stimulation Target 1 Detected | Stimulation Mode 1 = Off<br>Stimulation Mode 2 = On<br><u>166</u><br>State 3 | Stimulation Mode 1 = Off<br>Stimulation Mode 2 = On<br><u>168</u><br>State 4 |

FIG. 26

Closed Loop State Diagram with Control Policy Actions

| | Linear Detector 1 – Detect Event Biomarker<br>Control therapy delivery to Stimulation Mode 1<br>Example<br>Frequency = 100Hz<br>Onset and Term = low (Fast response) | |
|---|---|---|
| | Biomarker Not Detected | Biomarker Detected |
| Stimulation Target<br>1 Not Detected | Stimulation Mode 1 = Off<br>Stimulation Mode 2 = Off<br><br>162                          State 1 | Stimulation Mode 1 = On<br>Stimulation Mode 2 = Off<br><br>164                          State 2 |
| Stimulation Target<br>1 Detected | Stimulation Mode 1 = Off<br>Stimulation Mode 2 = On<br><br>166                          State 3 | Stimulation Mode 1 = Off<br>Stimulation Mode 2 = On<br><br>168                          State 4 |

Linear Detector 2 – detect presence of Stimulation Mode 1
Control therapy delivery to Stimulation Mode 2
Example
Frequency = 130Hz
Onset = 5 secs
Termination = 13 secs

FIG. 28

|  | | INS Computed LD1 | |
| --- | --- | --- | --- |
|  | | LD1 Low | LD1 High |
| Second Device Controlling LD2 | LD2 Low | Brain State Nominal. Stimulation Targets are X. | Brain State Seizure (from Nominal) Stimulation Targets are Q1. |
|  | LD2 In Range | Brain State Asleep. Stimulation Targets are Y. | Brain State Seizure (from Asleep) Stimulation Targets are Q2. |
|  | LD2 High | Brain State Pre-Seizure. Stimulation Targets are Z. | Brain State Seizure (from Pre-Seizure) Stimulation Targets are Q3. |

FIG. 32

MULTI-TARGET ADAPTIVE NEUROSTIMULATION THERAPY CONTROL

This application claims the benefit of U.S. Provisional Patent Application 62/925,069, filed 23 Oct. 2019, the entire content of which is incorporated herein by reference.

TECHNICAL FIELD

This disclosure describes techniques related to medical devices and, more particularly, to medical devices that deliver neurostimulation therapy.

BACKGROUND

Medical devices may be used to treat a variety of medical conditions. Medical electrical stimulation devices, for example, may deliver electrical stimulation therapy to a patient via implanted electrodes. Electrical stimulation therapy may include stimulation of nerve, muscle, or brain tissue, or other tissue within a patient. An electrical stimulation device may be fully implanted within the patient. For example, an electrical stimulation device may include an implantable electrical stimulation generator and one or more implantable leads carrying electrodes. Alternatively, the electrical stimulation device may comprise a leadless stimulator. In some cases, implantable electrodes may be coupled to an external electrical stimulation generator via one or more percutaneous leads or fully implanted leads.

Medical electrical stimulators may be used to deliver electrical stimulation therapy to patients to relieve a variety of symptoms or conditions such as chronic pain, tremor, Parkinson's disease, depression, obsessive compulsive disorder, epilepsy, urinary or fecal incontinence, pelvic pain, sexual dysfunction, obesity, or gastroparesis. An electrical stimulator may be configured to deliver electrical stimulation therapy via leads that include electrodes implantable proximate to the spinal cord, pelvic nerves, gastrointestinal organs, peripheral nerves, or within the brain of a patient. Stimulation proximate the spinal cord and within the brain are often referred to as spinal cord stimulation (SCS) and deep brain stimulation (DBS), respectively.

SUMMARY

This disclosure describes techniques for multi-target adaptive neurostimulation therapy control, including techniques for having an implantable medical device (IMD) transition between a no stimulation mode and at least two or more different stimulation modes.

According to one example, a method includes detecting an indicator of a symptom in a patient; in response to detecting the indicator of the symptom in the patient, delivering to the patient by an implantable medical device (IMD), a first stimulation therapy; and in response to determining that the indicator of the symptom has been present for more than a threshold amount of time after beginning to deliver the first stimulation therapy, delivering to the patient by the IMD, a second stimulation therapy different than the first stimulation therapy According to another example, a medical device system for therapy deliver includes stimulation circuitry; and processing circuitry configured to detect an indicator of a symptom in a patient; in response to detecting the indicator of the symptom in the patient, deliver to the patient, by the stimulation circuitry, a first stimulation therapy; and in response to determining that the indicator of the symptom has been present for more than a threshold amount of time after beginning to deliver the first stimulation therapy, deliver to the patient, by the stimulation circuitry, a second stimulation therapy different than the first stimulation therapy.

According to another example, a computer-readable medium storing instructions that when executed by one or more medical devices cause the one or more medical devices to detect an indicator of a symptom in a patient; in response to detecting the indicator of the symptom in the patient, deliver to the patient a first stimulation therapy; and in response to determining that the indicator of the symptom has been present for more than a threshold amount of time after beginning to deliver the first stimulation therapy, deliver to the patient a second stimulation therapy different than the first stimulation therapy.

According to another example, a system includes means for detecting an indicator of a symptom in a patient; means for delivering to the patient a first stimulation therapy in response to detecting the indicator of the symptom in the patient; and means for delivering to the patient a second stimulation therapy different than the first stimulation therapy in response to determining that the indicator of the symptom has been present for more than a threshold amount of time after beginning to deliver the first stimulation therapy.

The details of one or more aspects of the disclosure are set forth in the accompanying drawings and the description below. Other features, objects, and advantages will be apparent from the description and drawings, and from the claims.

BRIEF DESCRIPTION OF DRAWINGS

FIGS. 11A and 11B show examples of state tables that may be used by an IMD to implement state transitions according to techniques of this disclosure.

FIG. 14A shows an example of a state machine with 9 states.

FIG. 14B shows example targets for each state of a program in FIG. 14A.

FIG. 14C shows an example of limits that may be used for setting the parameters in FIGS. 14A and 14B.

FIG. 17 is a table illustrating an example of a closed loop state diagram with control policy actions.

FIG. 18 is a table illustrating an example of the closed loop state diagram of FIG. 17 corresponding to a first state (State 1).

FIG. 26 is a table illustrating an example of the closed loop state diagram of FIG. 17 corresponding to a transition from the second state (State 2) to a fourth state (State 4).

FIG. 28 is a table illustrating an example of the closed loop state diagram of FIG. 17 corresponding to a transition from the fourth state (State 4) to a third state (State 3).

FIG. 32 is a table illustrating another example of a closed loop state diagram for a multi-target adaptive neurostimulation therapy control algorithm in accordance with another example of this disclosure.

DETAILED DESCRIPTION

Figure 1:
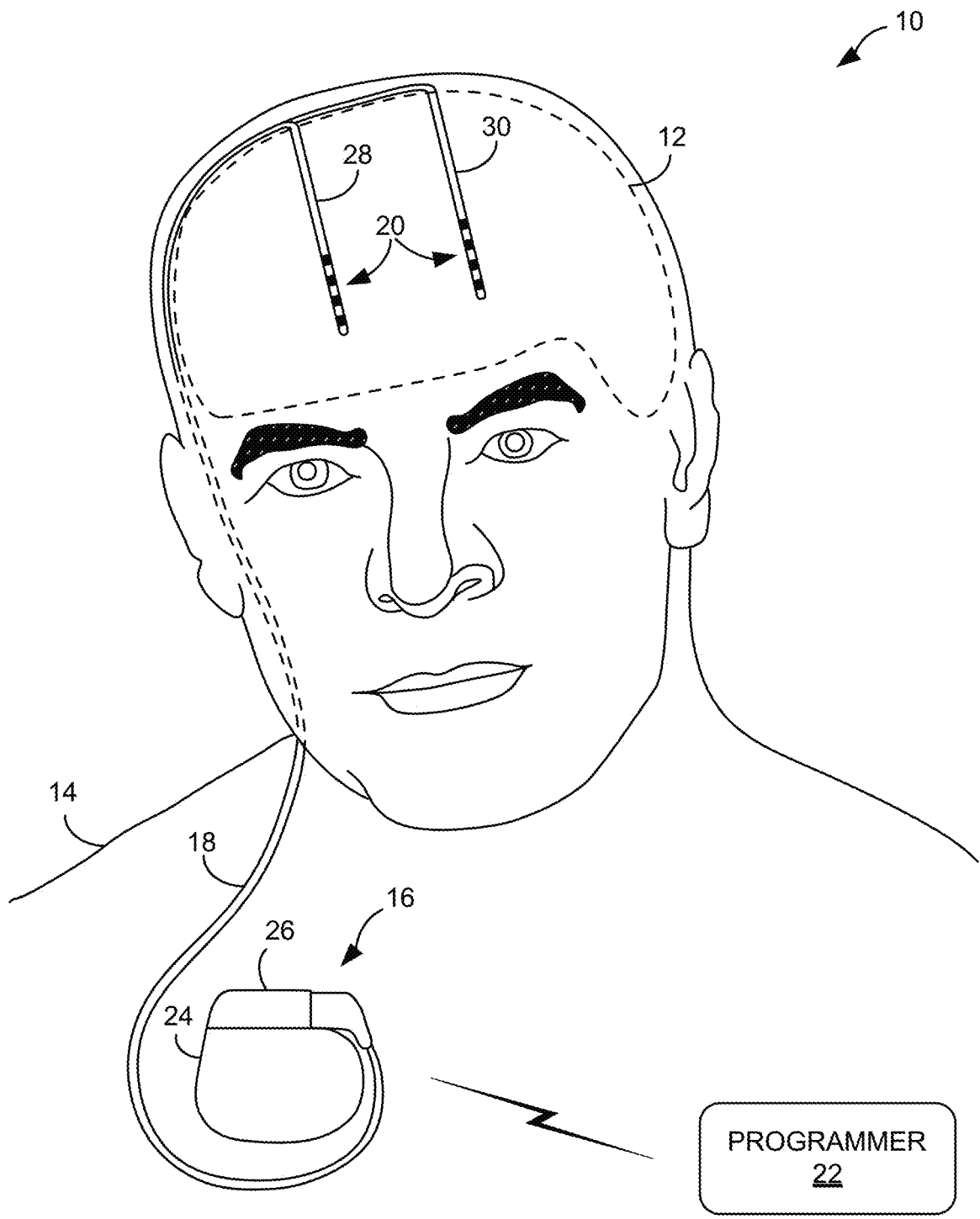
FIG. 1 is a conceptual diagram illustrating an example therapy system that may be used to implement multi-target adaptive neurostimulation therapy control in accordance with an example of this disclosure.

This disclosure describes techniques for multi-target adaptive neurostimulation therapy control, including techniques for having an implantable medical device (IMD) transition between a no stimulation mode and at least two or more different stimulation modes. As one example, an IMD may be configured to not deliver stimulation while a patient is asymptomatic, but in response to detecting an indicator of a symptom, the IMD may begin stimulating the patient in a first stimulation mode. The indicator of the symptom may, for example, correspond to a symptom or the onset of a symptom or may correspond to a condition with an increased chance of symptom onset, such as neural network excitability, which may be detectible prior to the onset of a symptom. Thus, as used in this disclosure, detecting a symptom may generally refer to actually detecting the presence of the symptom, detecting the onset of a symptom, or detecting, prior to the onset of a symptom, a condition with an increased likelihood of symptoms occurring. In the first stimulation mode, the IMD may, for example, deliver stimulation to a first target area. If the IMD detects that the symptoms are aborted (i.e., have been terminated as a result of the stimulation or otherwise stopped), then the IMD can cease stimulating in the first stimulation mode, e.g., cease stimulating the first target area or cease delivery of stimulation altogether.

If, however, the indicator of the symptoms continues for a certain period of time or if the IMD detects a change in monitored signal content, such as a change in frequency or intensity, then the IMD may transition to a second stimulation mode that delivers stimulation to a second target area. In some examples, the IMD may also be configured to transition to more than two target areas. In this context, a target area refers to a spatial location on a patient where therapy is being delivered. Different areas can be targeted by selecting different electrodes such as different ring electrodes along an axial length of lead and/or selecting different segmented electrodes at different axial positions and different circumferential positions on a lead to direct stimulation toward a different target area. As one example, for Tourette's syndrome, the IMD may deliver stimulation to the centromedian (CM) nucleus of the thalamus, and if after a period of time, the indicator of the symptoms has not aborted, then the IMD may alternatively or additionally begin delivering stimulation to the premotor cortex and/or motor Cortex In some examples, stimulation parameter settings (e.g., amplitude, frequency and/or pulse width) in the first stimulation mode may be the same as or different than the stimulation parameter settings in the second stimulation mode. In the second stimulation mode, the IMD may stimulate the second target area in addition to, or instead of, the first target area. In response to either the symptoms aborting or a time threshold being exceeded, the IMD may be configured to turn off all stimulation, i.e., stop delivering stimulation.

The techniques of this disclosure represent advancements in the technical field of adaptive neurostimulation, which may address shortcomings of some stimulation techniques, which are often tonic and not variant. One technique of this disclosure includes the use of multiple therapeutic target areas, where a target area refers to a location of the stimulating lead in neural tissue. For instance, utilizing the techniques of this disclosure, an IMD may be configured to selectively deliver electrical stimulation in a first stimulation mode to a primary target area but also deliver electrical stimulation in a second stimulation mode to a secondary target for a specific patient or disease state.

Potential benefits of the techniques described herein include better efficacy, longer device life, and increased ease of use. Delivering the stimulation in different stimulation modes to multiple, different target areas, i.e., locations, may allow for better treatment of diseases that are localizable to multiple nodes in a brain circuit model or have different symptoms that can be treated more effectively by stimulation of different targets. The delivery of stimulation to the multiple targets may be based on the efficacy of the stimulation for the primary target, the varying patient state, which may be classified by the IMD in real time, and other such factors. The techniques of this disclosure may enable an IMD to be adaptive and reactive to a current patient state, which may lead to less habituation and help to reduce side effects by only delivering stimulation when needed. The techniques of this disclosure may also provide secondary (e.g., backup) treatment in the even that symptomatic signals persist or progress (e.g., become more severe).

Furthermore, this disclosure also describes various state machine frameworks, including a table-based state machine framework, for programming closed-loop algorithms that control the delivery of multi-target adaptive neurostimulation therapy to a patient by an IMD in the manner described above. The table-based state machine framework may be used to implement a fixed number of possible states. Other types of state machine frameworks may be used to implement an arbitrary number of stated defined by a user. The state machine frameworks described in this disclosure represent some of, but not the only, mechanisms for implementing the therapy delivery techniques described in this disclosure. Additionally, this disclosure describes some, but not necessarily, all therapy delivery techniques that can be implemented using the state machine framework described herein. The state machine framework may use one or more programmable state parameters to define at least part of a structure of a state machine that generates one or more therapy decisions, including transitioning from one stimulation mode (e.g., delivering stimulation to a first target area and/or according to a first set of parameter settings) to another stimulation mode (e.g., delivering stimulation to a second target area different than the first target area and/or according to a second set of parameter settings different than the first set of parameter settings), based on one or more classified states of the patient.

An example of a state machine framework may include a state machine runtime environment that executes on an IMD and that is configurable to implement a variety of different state machines depending on programmable state parameters that are received from an external device. Using a state machine runtime environment that operates based on downloadable state parameters may allow, in some examples, different state machines to be implemented on an IMD at different times with the same generic, state machine-independent firmware code. In this way, the techniques of this disclosure may allow IMD developers and/or users to program, change, and/or download new closed-loop control policy algorithms during the lifespan of the IMD without requiring new firmware code to be downloaded onto the IMD.

FIG. 1 is a conceptual diagram illustrating an example therapy system 10 that may be used to implement stimulation techniques of this disclosure and the state machine framework of this disclosure. Therapy system 10 is configured to deliver electrical stimulation therapy to brain 12 of patient 14. Patient 14 may ordinarily, but not necessarily, be a human. Therapy system 10 includes an implantable medical device (IMD) 16, a lead 18, electrodes 20, and a programmer 22.

IMD 16 is configured to sense one or more physiological states of patient 14 via one or more sensors, and to deliver electrical stimulation to brain 12 of patient 14 via electrodes 20 based on the sensed physiological states of patient 14. The electrodes 20 used to deliver electrical stimulation may be implantable electrodes that are deployed on one or more implantable medical leads (e.g., lead 18) and, in some cases, deployed on a can electrode, i.e., an electrode carried on or formed by a conductive housing, or "case" or "can," of an implantable stimulation pulse generator connected to the lead or leads. In the example of therapy system 10 of FIG. 1, IMD 16 is implanted within a subcutaneous pocket in a clavicle region of patient 14. IMD 16 may be configured to communicate with one or more external devices (e.g., programmer 22). IMD 16 is mechanically and electrically coupled to lead 18 and to electrodes 20 via lead 18. IMD 16 includes a housing 24 and a connector block 26.

Housing 24 is configured to carry components that perform some or all of the functionality attributed to IMD 16 in this disclosure. For example, housing 24 may include electrical circuitry and components that control the operation of IMD 16. Housing 24 may also include one or more power sources (e.g., one or more batteries) to power the electrical components inside of housing 24. In addition, housing 24 may include telemetry circuitry that is configured to communicate with one or more external devices via radio telemetry techniques. Housing 24 may be formed from any material capable of carrying the components that perform the functionality attributed to IMD 16. In some cases, housing 24 may be formed from a conductive material. In additional cases, housing 24 may be a hermetically-sealed housing. Housing 24 is mechanically coupled to connector block 26.

Connector block 26 is configured to mechanically and electrically couple lead 18 to housing 24 of IMD 16. For example, connector block 26 may include a connection port configured to receive a proximal end of lead 18. When the proximal end of lead 18 is inserted into the connection port of connector block 26, connector block 26 may be configured to electrically couple lead 18 to one or more electrical components in housing 24. In some cases, connector block 26 may be formed from a flexible, insulative material. Connector block 26 is mechanically coupled to housing 24.

In some examples, IMD 16 may deliver, as neurostimulation therapy, deep brain stimulation (DBS) or cortical stimulation (CS) therapy to patient 14 via electrodes 20 based on the sensed physiological states of patient 14 to treat any of a variety of neurological disorders or diseases. Example neurological disorders may include depression, dementia, Alzheimer's disease, and obsessive-compulsive disorder. Example neurological disorders may also include movement disorders, such as Parkinson's disease, Tourette's syndrome spasticity, epilepsy, essential tremor, dyskinesia, dystonia, and other movement disorders detectable by local field potential sensors and/or inertial-based sensors. DBS also may be useful for treating other patient conditions, such as migraines and obesity.

Lead 18 is configured to mechanically and electrically couple electrodes 20 to IMD 16. A proximal end of lead 18 may be connected to housing 24 of IMD 16. A distal end of lead 18 may include electrodes 20 that are implanted in brain 12 of patient 14. As shown in FIG. 1, lead 18 may traverse from the implant site of IMD 16 along the neck of patient 14 to the cranium of patient 14 to access brain 12. Although the example therapy system 10 of FIG. 1 illustrates a lead 18 that is electrically and mechanically coupled directly to connector block 26, in other examples, lead 18 may be electrically or mechanically coupled indirectly to connector block 26 via one or more lead extensions. In additional examples, therapy system 10 may include multiple implantable leads instead of a single lead 18.

The example lead 18 illustrated in FIG. 1 is a bifurcated lead that includes lead segments 28, 30 (also referred to as leads 28, 30) at the distal end of lead 18. Lead segments 28, 30 each include a set of electrodes that form a part of electrodes 20. Conductors in the lead body may electrically couple stimulation electrodes located on lead segments 28, 30 to IMD 16. In various examples, lead segments 28, 30 may each carry four, eight, or sixteen electrodes. In the example therapy system 10 if FIG. 1, each of lead segments 28, 30 carries four electrodes that are configured as ring electrodes at different axial positions near the distal ends of lead segments 28, 30. For purposes of simplicity, the remainder of this disclosure may generally refer to electrodes carried on "leads" rather than "lead segments." In additional examples, IMD 16 may be coupled to one or more leads that may or may not be bifurcated. In such examples, the leads may be coupled to lead 18 via a common lead extension or via separate lead extensions.

In some examples, lead segments 28, 30 may include segmented electrodes that are distributed at different axial and circumferential positions around the lead and may be used to directionally deliver stim to precise targets. These electrode segments may be individually controllable/addressable and be used to deliver stim in a more directional manner. For instance, rather than transmitting stimulation 360 degrees around the lead body, an individual electrode segment may transmit stimulation in an angular region of 90 degrees, making the stimulation more selectively target particular tissue in a particular direction and enabling the delivery of stimulation to different target areas by selecting different ring electrodes and/or different segmented electrodes.

Leads 28, 30 may be implanted within a desired location of brain 12 through respective holes in the cranium of patient 14. In general, leads 28, 30 may be placed at any location within brain 12 such that the electrodes located on leads 28, 30 are capable of providing electrical stimulation to targeted tissue during treatment. The region of patient 14 to which electrical stimulation is delivered may, in some examples, be selected based on the patient condition or disorder. In the example therapy system 10 of FIG. 1, lead segments 28, 30 are implanted within the right and left hemispheres, respectively, of patient 14 in order to deliver electrical stimulation to one more regions of patient 14. Other example locations for lead segments 28, 30 within brain 12 may include the pedunculopontine nucleus (PPN), thalamus, basal ganglia structures (e.g., globus pallidus, substantia nigra, subthalamic nucleus), zona inserta, fiber tracts, lenticular fasciculus (and branches thereof), ansa lenticularis, and/or the Field of Forel (thalamic fasciculus). In the case of migraines, lead segments 28, 30 may be implanted to provide stimulation to the visual cortex of brain 12 in order to reduce or eliminate migraine headaches afflicting patient 14. Again, the target therapy delivery site may depend upon the patient condition or disorder being treated.

In the example therapy system 10 of FIG. 1, electrodes 20 are ring electrodes. Ring electrodes are commonly used in DBS applications because they are simple to program and are capable of delivering an electrical field to any tissue adjacent to lead segments 28, 30. In other examples, electrodes 20 may have different configurations. For example, electrodes 20 may have a complex electrode array geometry that is capable of producing shaped electrical fields. The complex electrode array geometry may include multiple electrodes (e.g., partial ring or segmented electrodes) around the perimeter of each of electrodes 20, rather than one ring electrode. In this manner, electrical stimulation may be directed in a specific direction from lead segments 28, 30 to enhance therapy efficacy and reduce possible adverse side effects from stimulating a large volume of tissue. In alternative examples, lead segments 28, 30 may have shapes other than elongated cylinders as shown in FIG. 1. For example, lead segments 28, 30 may be paddle leads, spherical leads, bendable leads, or any other type of shape effective in delivering electrical stimulation therapy to patient 14.

Each of electrodes 20 may be configured to deliver electrical stimulation to brain 12 of patient 14 and/or to sense electrical activity that occurs in brain 12 of patient 14. For examples, each of electrodes 20 may be configured to function as a stimulation electrode, a sense electrode, or a combination stimulation/sense electrode. As shown in FIG. 1, each of electrodes 20 is implanted in brain 12 of patient 14. In additional examples, one or more electrodes that are not implanted in brain 12 of patient 14 may be used for sensing and/or for delivery of therapy in addition to or in lieu of electrodes 20. For example, a can electrode that is formed on housing 24 of IMD 16 may be used for the delivery of therapy in combination with electrodes 20. IMD 16 may be configured to deliver stimulation in a bipolar mode (e.g., by an anode and cathode on a lead), a multipolar mode (e.g., by multiple anodes and/or cathodes on a lead), or in a unipolar mode (e.g., by one or more cathodes on lead and one anode on housing 24, or one or more anodes on a lead and one cathode on housing 24).

The electrical stimulation therapy delivered to brain 12 of patient 14 may take the form of constant current or voltage pulses or substantially continuous waveforms. Various parameters of the pulses or waveforms may be defined by a stimulation program. The pulses or waveforms may be delivered substantially continuously or in bursts, segments, or patterns, and may be delivered alone or in combination with pulses or waveforms defined by one or more other stimulation programs.

Programmer 22 is an external computing device that is configured to wirelessly communicate with IMD 16. The wireless communication facilitated by programmer 22 may include transmitting and receiving data and/or controlling the operation of programmer 22. A user, e.g., a clinician and/or patient 14, may use programmer 22 to communicate with IMD 16. In some examples, programmer 22 may be a clinician programmer that a clinician uses to communicate with IMD 16 (e.g., to program one or more therapy programs for IMD 16). In further examples, programmer 22 may be a patient programmer that a patient uses to communicate with IMD 16 (e.g., to select programs, view electrical stimulation parameters, and/or modify electrical stimulation parameters). The clinician programmer may, in some examples, include more programming features than the patient programmer. In other words, certain types of complex and/or sensitive tasks may, in such examples, only be allowed by the clinician programmer to prevent an untrained patient from making undesired changes to IMD 16.

Programmer 22 may be any type of computing device including, for example, a hand-held computing device, a computer workstation, a notebook computer, a tablet computer, a cellular phone, a personal digital assistant (PDA), etc. In some cases, programmer 22 may be implemented on a computing device that executes a software application that enables the computing device to operate as a programmer 22. In some cases, the computing device may include a wireless adapter that enables secure communication between programmer 22 and IMD 16.

Programmer 22 may include a display viewable by the user and an interface for providing input to programmer 22 (i.e., a user input mechanism). For example, programmer 22 may include a small display screen (e.g., a liquid crystal display (LCD) or a light emitting diode (LED) display) that provides information to the user. In addition, programmer 22 may include a touch screen display, keypad, buttons, a peripheral pointing device or another input mechanism that allows the user to navigate through the user interface of programmer 22 and provide input. In cases where the display is a touch screen display, the user may, in some examples, use a stylus or a finger to provide input to the display.

When programmer 22 is configured for use by the clinician, programmer 22 may be used to transmit initial programming information to IMD 16. The programming information may include the type of lead 18, the electrode arrangement of electrodes 20, the position of lead 28 and/or 30 within brain 12, the configuration of an electrode array formed by electrodes 20, programs defining electrical stimulation parameter values, and any other information the clinician desires to program into IMD 16. In some cases, programmer 22 may be configured to upload operational or physiological data stored by IMD 16. For example, the clinician may use programmer 22 to periodically interrogate IMD 16 to evaluate efficacy and, if necessary, modify the programs or create new programs.

Programmer 22 may be used by a clinician to control the delivery of electrical stimulation, such as, e.g., activating electrical stimulation, deactivating electrical stimulation, or adjusting one or more stimulation parameters of therapy being delivered to patient 14. The clinician may also use programmer 22 to store therapy programs within IMD 16. During a programming session, the clinician may determine one or more therapy programs that may provide efficacious therapy to patient 14 in order to address symptoms associated with a disorder of patient 14. Patient 14 may provide feedback to the clinician as to the efficacy of the specific program being evaluated.

When programmer 22 is configured for use by patient 14, programmer 22 may provide patient 14 with a user interface for control of the stimulation therapy delivered by IMD 16. For example, patient 14 may use programmer 22 to start, stop or adjust electrical stimulation therapy. As another example, programmer 22 may permit patient 14 to adjust stimulation parameters of a program such as duration, current or voltage amplitude, pulse width and pulse rate. Patient 14 may also select a program, e.g., from among a plurality of stored programs, as a program to control delivery of stimulation by IMD 16.

Programmer 22 may also provide various indications to patient 14 to alert patient 14 of various operating conditions of IMD 16. For example, IMD 16 may provide an indication of when therapy is being delivered, when a patient input has triggered a change in electrical stimulation parameters or when a power source within programmer 22 and/or IMD 16 needs to be replaced or recharged. For example, programmer 22 may include an alert LED that may flash a message to patient 14 via a programmer display, or may generate an audible sound or somatosensory cue to confirm patient input was received, e.g., to indicate a patient state or to manually modify an electrical stimulation parameter.

Programmer 22 may communicate with IMD 16 and, optionally, another computing device, via wireless communication. Programmer 22 may, for example, communicate via wireless communication with IMD 16 using radio frequency (RF) telemetry techniques known in the art. Programmer 22 may also communicate with another programmer or computing device via a wired or wireless connection using any of a variety of local wireless communication techniques, such as, e.g., RF communication according to the 802.11 or Bluetooth™ specification sets, infrared (IR) communication according to the Infrared Data Association (IRDA) specification set, or other standard or proprietary telemetry protocols.

In additional examples, programmer 22 may communicate with other programming or computing devices via exchange of removable media, such as magnetic or optical disks, memory cards or memory sticks. In further examples, programmer 22 may communicate with IMD 16 and another programmer via remote telemetry techniques, a local area network (LAN), a wide area network (WAN), a public switched telephone network (PSTN), or a cellular telephone network, for example. In further examples, programmer 22 may communicate with IMD 16 via a cable. Each of programmer 22 and IMD 16 may include a transceiver to permit bi-directional communication.

According to some examples of this disclosure, IMD 16 may be configured to adaptively control the delivery of neurostimulation therapy to multiple targets of patient 14, e.g., based on a state machine that has a structure which is defined at least in part by one or more programmable state parameters. The state machine may generate one or more therapy decisions based on one or more sensed states of patient 14. In some examples, IMD 16 may receive the programmable state parameters from a device other than IMD 16 (e.g., programmer 22). Using a state machine that has a structure which is defined at least in part by one or more programmable state parameters to control the delivery of therapy to patient 14 may allow execution paths for therapy delivery control policy algorithms to be programmed and/or reconfigured during the operational lifespan of IMD 16.

In some examples, IMD 16 may execute a state machine runtime environment that is configurable to implement a variety of different state machines depending on programmable state parameters that are received from an external device (e.g., programmer 22). The state machine runtime environment, in some cases, may be part of a set of firmware code that is executed by IMD 16. Using a state machine runtime environment that operates based on downloadable state parameters may allow, in some examples, different state machines to be implemented on IMD 16 at different times with the same generic, state machine-independent firmware code executing on IMD 16. In this way, the techniques of this disclosure may allow IMD developers and/or users to program, change, and/or download new closed-loop control policy algorithms during the operational lifespan of IMD 16 without requiring new firmware code to be downloaded onto IMD 16.

In some examples, the therapy decisions generated by the state machine implemented by IMD 16 may include selecting one or more stimulation programs from a set of stimulation programs to use for delivering electrical stimulation therapy to a patient, determining whether to enable or disable the delivery of electrical stimulation therapy to the patient, determining whether to increase, decrease, or keep constant one or more stimulation parameters used for delivering electrical stimulation therapy, and/or determining whether to provide stimulation to a particular target area, such as a second target area in addition to or instead of a first target area. Example stimulation parameters that may be adjusted may include, e.g., an amplitude of the stimulation, a pulse width of the stimulation, a frequency of the stimulation, and a target area for the stimulation. Other therapy decisions may also be used in addition to or lieu of the above-mentioned therapy decisions.

The inputs to the state machine implemented by IMD 16 may include data indicative of the sensed states of patient 14 (e.g., classified states of patient 14) or other data such as data indicative of a stimulation state (e.g., delivered or not delivered) or data indicative of a medication state of patient 14. The data indicative of the sensed states of patient 14 may be generated based on data received from one or more sensors. These sensors may be included in IMD 16 or external to IMD 16. In some examples, the sensors may include inertial sensors (e.g., an accelerometer), chemical sensors, pressure sensors, temperature sensors, optical sensors, impedance sensors, bioelectrical sensors, etc. In some examples, an inertial sensor may be configured to sense and/or detect patient posture, patient activity, patient movement, patient tremor, the motor characteristics of a seizure, etc. Bioelectrical sensors may include sensors that sense bioelectrical signals, such as, e.g., local field potential (LFP) signals, electrocardiography (ECG) signals, electromyography (EMG) signals, evoked potentials, etc.

In some cases, the bioelectrical sensors may sense one or more electrical characteristics of patient 14 via electrodes 20 in order to sense a physiological state of brain 12. Bioelectrical sensors may include, for example, one or more sense electrodes and electrical sensing circuitry. The bioelectrical sensors may, for example, be configured to detect whether biomarkers are present or not present. Biomarkers may, for example, refer to changes in sensed electrical activity, such as amplitude, power, or other changes in an LFP, or may also refer to other detectable patient characteristics, such as movement.

Bioelectrical sensors may detect biomarkers based on, for example, amplitudes or power of the LFP in one or more spectral bands. As an example, a bioelectrical sensor may detect biomarkers based on the power within a band exceeding a threshold or based on ratios between amplitude or power of LFPs in different spectral bands. For example, a given biomarker may be detected based on a threshold power ratio between two or more spectral bands (e.g., beta vs. gamma activity). In other words, a biomarker may be detected if the ratio of power in one spectral band to power in another spectral band meets or exceeds a threshold ratio value. A motion sensor may, for example, detect a motion event by measuring motion, using an accelerometer for instance, and identifying the motor component of seizure, such as for a tonic seizure or tonic-clonic seizure, or detect a fall. The motion sensor may also use a timer to classify motion events, for example, only identifying motion events that last for a certain amount of time in order to minimize false positives. To process the data indicative of the sensed states of patient 14, IMD 16 may execute one or more classifiers. Each of the classifiers may be configured to detect and/or classify whether patient 14 is in a given state based at least in part on a stimulation state, a medication state, and/or physiological data received from one or more sensors, such as a detection of a biomarker, and generate data indicative of whether the given state has been detected for patient 14. Example states may include detection of a biomarker, which may indicate states whether a patient is experiencing a particular patient condition, such as, e.g., seizure onset, an ongoing seizure, a Parkinson's disease (PD) episode, network suppression, desynchronization, and/or depression. In some examples, the biomarkers may be based on bioelectrical signal characteristics such as, e.g., beta-to-gamma power ratio states. Alternatively, or additionally, states may be detected by inertial sensors, e.g., in the case of Parkinson's disease, epilepsy, Tourette's syndrome, or other movement disorder episodes.

Using sensed states of a patient to control therapy decisions generated by a state machine may allow IMD 16 to implement closed-loop control policy algorithms that control the delivery of therapy by IMD 16 to patient 14. Because the state machine has a structure that is defined by downloadable, programmable state parameters, a flexible framework may be provided for downloading and programming closed-loop control policy algorithms onto IMD 16.

In some examples, the electrical stimulation therapy delivered by IMD 16 to patient 14 may be neurological stimulation therapy, which may be referred to as neurostimulation or neuromodulation therapy, and at least some of the sensed states of patient 14 may be sensed neurological states of patient 14. In further examples, the electrical stimulation therapy delivered by IMD 16 to patient 14 may be electrical stimulation therapy delivered to brain 12 of patient 14, and at least some of the sensed states of patient 14 may be sensed brain states of patient 14, e.g., where states are detected or inferred by bioelectrical sensors, inertial sensors, or other sensors.

As discussed above, the programmable state parameters may define at least part of the structure of the state machine implemented by IMD 16. In some examples, the structure of a state machine may refer to one or more of the following: the number of states in the state machine, the configuration of state transitions that occur between the different states in the state machine, the entry actions for each of the states in the state machine, the exit conditions for each of the states in the state machine, the time delays between each of the states in the state machine, whether timeouts are enabled for each of the states in the state machine, and/or the length of timeout specified for states in the state machine where timeouts are enabled.

In some examples, the structure of a state machine may be defined at least in part by a next state transfer function that determines which state is the next state to execute based on the current state and one or more inputs to the state machine. In other words, the structure of the state machine may specify under what conditions transitions between the various states in the state machine are to occur. In some cases, each of the inputs used to determine the next state may correspond to one or more sensed states of the patient (e.g., one or more signals generated by one or more classifiers that classify sensed states of the patient). In additional examples, the structure of the state machine may be defined at least in part by one or more actions that occur when operating in each of the states. In some cases, the actions may include actions that control the delivery of electrical stimulation therapy.

In some examples, the state parameters may include state parameters that specify one or more entry actions for one or more states in the state machine. Entry actions may refer to actions that are performed when entering the state (e.g., transitioning to the state from another state). Example entry actions may include one or more of an action that selects one of a plurality of stimulation programs to be used for delivery of stimulation, an action that turns on the delivery of the stimulation to a first target area, an action that turns off the delivery of the stimulation, an action that causes no change to an activation state of the stimulation, an action that increases or decreases (e.g., increments or decrements) one or more stimulation parameters, an action that turns off the delivery of stimulation to the first target area, an action that turns on the delivery of stimulation to a second target area, and an action that causes a timeout to occur if no exit conditions are satisfied after a specified period of time. The stimulation parameters that may be increased or decreased via entry actions may include, in some examples, an amplitude of the stimulation, a pulse width of the stimulation, and a frequency of the stimulation. In addition, or alternatively, entry actions may cause selection of different electrode combinations or different stimulation programs. In some cases, individual entry actions or groups of entry actions may correspond to therapy decisions made by the state machine. Using state parameters to specify entry actions for the states in a state machine may provide a flexible framework for programming control policy algorithms that are capable changing and/or adjusting stimulation programs based on sensed states of a patient during the execution of the control policy algorithm.

In further examples, the state parameters may include state parameters that specify one or more exit conditions for one or more states in the state machine. An exit condition may specify a condition that is to occur prior to transferring to a next state associated with the exit condition. Each exit condition may include a condition portion that specifies a condition to be evaluated and a next state portion that specifies to which state the state machine is to transition if the condition specified in the condition portion is satisfied. Example exit conditions may include a user-specified combination of one or more of a plurality of state classifier outputs where each of the state classifier outputs is indicative of whether a respective one of one or more physiological states has been detected for the patient based on data received from one or more physiological sensors. Another example exit condition is a timer which, when expires, causes the state to transition to another state. Using state parameters to specify exit conditions and associated next states for states in a state machine may allow sensed physiological states of a patient to be used to control the execution paths in the state machine.

In additional examples, the state parameters may include state parameters that are indicative of a priority assigned to each of the exit conditions for a particular state. The priority assigned to each of the exit conditions may indicate an order of precedence for the exit conditions in a case where multiple different exit conditions are satisfied when operating in the current state. Assigning priorities to the exit conditions may avoid the need to include every single combination of a set of possible state machine inputs in a data representation of the state machine. In this way, the amount of data needed to represent and/or store the state machine may be reduced.

Although FIG. 1 shows a fully implantable IMD 16, the state machine framework techniques described in this disclosure may be applied to medical devices that are external to patient 14 or may be applied to systems that use multiple devices, such as IMD 16 in conjunction with an external device. An external device may have electrodes deployed via percutaneously implantable leads. In addition, the techniques of this disclosure is not limited to the configuration of leads and electrodes shown in FIG. 1, but in other examples may include more or less leads, more or less electrodes, and electrodes disposed on other locations besides an implantable lead (e.g., an electrode located on a housing 24 of IMD 16 (i.e., a "can" or "case" electrode)). In addition, in some cases, implantable electrodes may be deployed on a leadless implantable medical device. Although the example techniques of this disclosure are primarily described with respect to medical devices that deliver DBS or CS therapy, the techniques of this disclosure may also be applied to other medical devices including, e.g., medical devices that provide spinal cord stimulation therapy, medical devices that provide gastroenterological therapy (e.g., gastro/urology therapy) and/or medical devices that deliver drug therapy, optical therapy, and/or ultrasound stimulation therapy.

Figure 2:
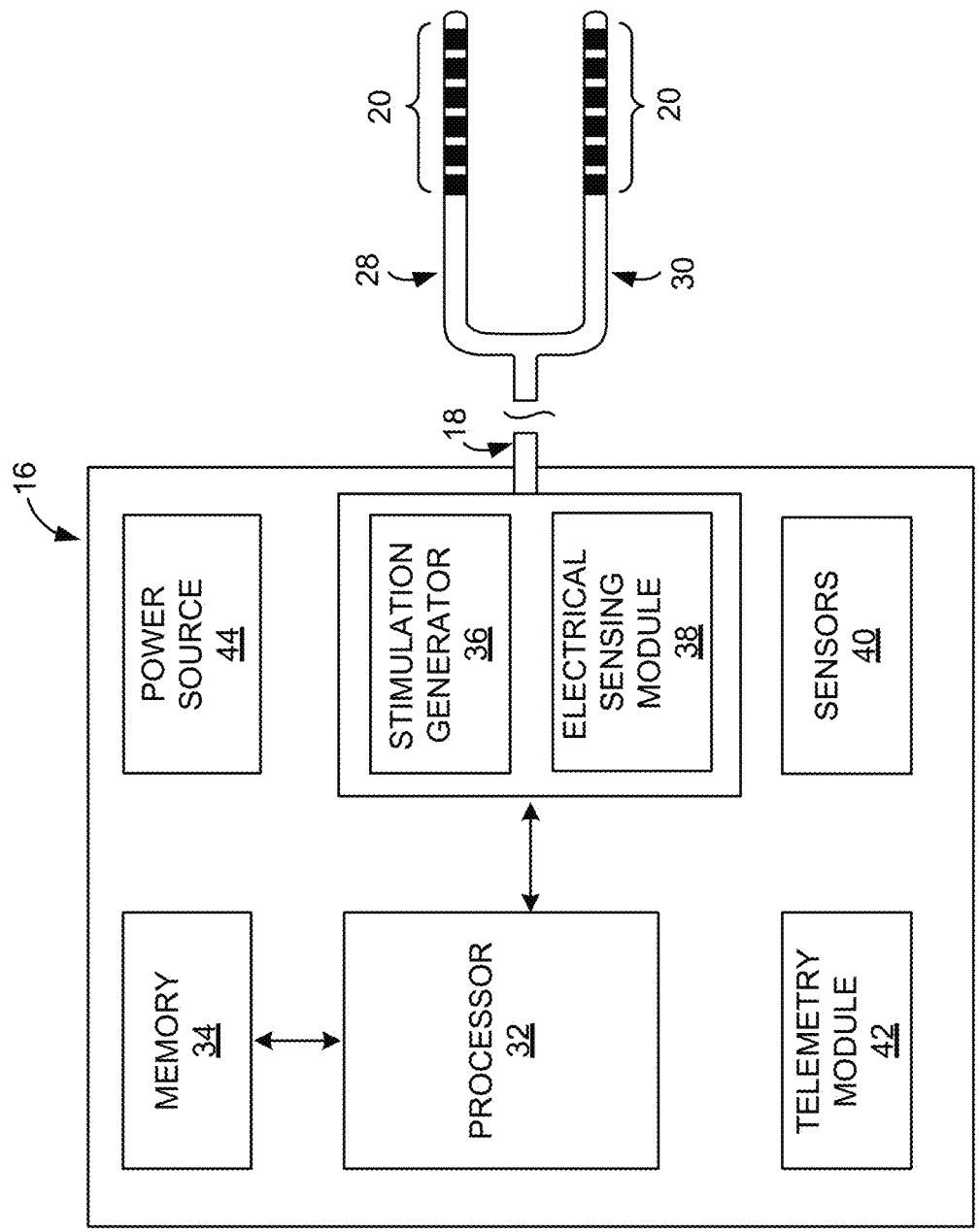
FIG. 2 is a functional block diagram illustrating an example of the implantable medical device (IMD) of FIG. 1 in greater detail.

FIG. 2 is a functional block diagram illustrating the IMD 16 of FIG. 1 in greater detail. IMD 16 is configured to deliver electrical stimulation therapy to patient 14 based on one or more sensed states of patient 14. IMD 16 includes a processor 32, a memory 34, a stimulation generator 36, an electrical sensing module 38, sensors 40, a telemetry module 42 and a power source 44. Each of the components included in IMD 16 may be disposed in housing 24 of IMD 16. Stimulation generator 36 and electrical sensing module 38 are electrically coupled to electrodes 20 via lead 18.

Processor 32 is configured to control the operation of IMD 16 to perform the functions attributed to IMD 16 in this disclosure. For example, processor 32 may control IMD 16 to sense one or more states of patient 14, and to deliver electrical stimulation to brain 12 of patient 14 based on the sensed states of patient 14. To control the delivery of electrical stimulation based on the sensed states of patient 14, processor 32 may execute a state machine framework that is configured to control delivery of therapy by IMD 16 based on a state machine. The state machine may generate one or more therapy decisions based on one or more sensed states of patient 14. The state machine may have a structure that is defined at least in part by one or more programmable state parameters. In some cases, processor 32 may be configured to receive the programmable state parameters from a device other than IMD 16 (i.e., an external device (e.g., programmer 22)) via telemetry module 42.

In some examples, the state machine may define a control policy algorithm for controlling the delivery of therapy based on sensed and/or classified physiological states of patient 14. In such examples, processor 32 may control the delivery of therapy in accordance with the control policy algorithm defined by the programmable state machine.

To control IMD 16 to deliver electrical stimulation therapy, processor 32 may cause stimulation generator 36 to deliver electrical stimulation therapy to one or more tissue sites of brain 12 of patient 14 via lead 18. In some cases, processor 32 may subdivide electrodes 20 into different subsets of electrodes and cause each of the different subsets of electrodes to deliver electrical stimulation to a respective one of a plurality of target tissue sites. For example, processor 32 may cause stimulation generator 36 to deliver electrical stimulation to a first target tissue site via a first subset of electrodes 20 (e.g., electrodes 20 located on lead segment 28) in a first stimulation mode and to deliver electrical stimulation to a second target area via a second subset of electrodes 20 (e.g., electrodes 20 located on lead segment 30) in a second stimulation mode. In some cases, the electrical stimulation delivered by each of the subsets of electrodes may be delivered according to a different one of a plurality of therapy programs. For example, the electrical stimulation delivered via the first subset of electrodes may be delivered via a first therapy program in the first stimulation mode, and the electrical stimulation delivered via the second subset of electrodes may be delivered via a second therapy program different than the first therapy program in the second stimulation mode. The electrical stimulation that is delivered via each of the subsets of electrodes 20 may be controlled independently and may be controlled and delivered either simultaneously or alternately in time. In other examples, processor 32 may cause stimulation generator 36 to deliver electrical stimulation to several different target tissue sites with some or all of the same electrodes.

To sense the patient states, processor 32 may use one or both of electrical sensing module 38 and sensors 40, e.g., as described above. For example, processor 32 may receive physiological data from one or both of electrical sensing module 38 and sensors 40 and classify or detect patient states based on the received physiological data, e.g., by detecting the presence of a biomarker. In some examples, the physiological data may be bioelectrical physiological data (e.g., LPF, ECG, EMG, etc.) received from electrical sensing module 38. In further examples, the physiological data may be data received from sensors 40. In cases where sensors 40 include an inertial sensor, processor 32 may receive inertial physiological data (e.g., data indicative of patient posture, patient activity, patient movement, a patient motor seizure, patient tremor, etc.) received from sensors 40. In some cases, the physiological data may correspond to a physiological signal. Similarly, the bioelectrical physiological data may correspond to a biomarker detected in a bioelectrical signal, and the inertial physiological data may correspond to an inertial signal. In some cases, the physiological data received by processor 32 may be additionally or alternatively received from one or more sensing modules and sensors that are wirelessly coupled to IMD 16. Such sensors may be fully or partially implanted or may be carried externally by patient 14 (e.g., as in the case of inertial sensors).

In some examples, processor 32 may generate data indicative of the sensed states of patient 14 based on the physiological data received from electrical sensing module 38 and/or sensors 40 and provide the data indicative of the sensed states of patient 14 to the state machine framework. The state machine framework may generate therapy decisions based on the data indicative of the sensed states of patient 14 and a state machine implemented by the state machine framework.

In some examples, processor 32 may receive the data indicative of the physiological data directly from electrical sensing module 38 and/or sensors 40. In further examples, electrical sensing module 38 and/or sensors 40 may store the physiological data in memory 34, and processor 32 may access memory 34 to retrieve the physiological data.

The data indicative of the sensed states of patient 14 may, in some examples, take the form of one or more binary values. In such examples, each of the binary values may correspond to a respective one of a plurality of physiological states that may be sensed by patient 14. For example, each of the binary values may be indicative of whether a respective one of one or more physiological states has been detected for patient 14 based on the data received from one or more physiological sensors (i.e., electrical sensing module 38 and/or sensors 40).

To generate the data indicative of the sensed states of patient 14, processor 32 may execute one or more classifiers. Each of the classifiers may be configured to detect and/or classify whether patient 14 is in a given state based on physiological data received from electrical sensing module 38 and/or sensors 40 and generate data indicative of whether the given state has been detected for patient 14. The classifiers may perform computation and/or statistical analysis to detect and/or classify a particular state. Example states that may be classified and/or detected by classifiers executing on IMD 16 may include whether a patient is experiencing a particular patient condition, such as, e.g., a seizure, Parkinson's disease (PD), network suppression, desynchronization, and/or depression. Other example states that may be classified include PD on/off states, and beta-to-gamma ratio states.

In some examples, the classifiers may compare the detected biosignal to determine if one or more biomarkers are present. The classifiers may, for example, compare the detected biosignal to one or more previously recorded biosignals. For example, processor 32 may compare a particular characteristic of the detected biosignal to the same characteristic (e.g., a signature biosignal characteristic) of the previously recorded biosignals. Example signal characteristics that can be compared include, but are not limited to, a power level within one or more frequency bands, a ratio of power levels within two or more frequency bands, a peak, average or lowest biosignal amplitude within a particular range of time, a characteristic waveform of the biosignal (e.g. "saw-tooth" wave forms from an EEG signal), a pattern in a biosignal amplitude over time, and the like. Any of these various signal characteristics may constitute a biomarker.

Processor 32 may include, for example, any one or more of a microprocessor, a controller, a digital signal processor (DSP), an application specific integrated circuit (ASIC), a field-programmable gate array (FPGA), and discrete logic circuitry. The functions attributed to processor 32 herein may be implemented as firmware, hardware, software or any combination thereof. In general, components described as processors within IMD 16, programmer 22, or any other device described in this disclosure may each comprise one or more processors, such as one or more microprocessors, DSPs, ASICs, FPGAs, programmable logic circuitry, or the like, either alone or in any suitable combination. The functions attributed to processors described herein may be provided by a hardware device and implemented as software, firmware, hardware, or any combination thereof.

Memory 34 may store data relating to patient 14, such as the patient's name and age, the type of IMD 16 or electrodes 20 implanted within patient 14, medication prescribed to patient 14, and the like. Processor 32 of IMD 16 may also collect diagnostic information and store diagnostic information within memory 34 for future retrieval by a clinician. Diagnostic information may include information or activities indicated by patient 14 using programmer 22, such as changes in symptoms, medication ingestion, or other activities of patient 14. A clinician may review the diagnostic information in a variety of forms, such as timing diagrams or a graph resulting from statistical analysis of diagnostic information, e.g., a bar graph. The clinician may, for example, download diagnostic information from IMD 16 via programmer 22 or another computing device. Diagnostic information may also include calibration routines for electrodes 20 and malfunction algorithms to identify stimulation dysfunctions.

Each program may specify a set of stimulation parameters, such as amplitude, pulse width and pulse rate, if applicable and may specify one or more stimulation patterns (e.g., cycling, randomized, staircase, etc.). For a continuous waveform, parameters may include amplitude and frequency. In addition, each program may specify a particular electrode combination for delivery of stimulation, and an electrode configuration in terms of the polarities and regulated/unregulated status of the electrodes. Again, the electrode combination may specify particular electrodes in a single array or multiple arrays, and on a single lead or among multiple leads.

Memory 34 may store data indicative of a state machine that defines a control policy algorithm for IMD 16. The state machine and/or the control policy algorithm may generate therapy decisions based on one or more sensed states of patient 14. In some examples, the data indicative of the state machine may be stored in the form of a state transition table. The state transition table may, in some examples, include an entry for each state transition in the state machine. Each entry of the state transition table may include, in some examples, state parameters associated with the state transition. For example, each entry of the state transition table may include data indicative of the current state associated with a respective one of the state transitions, data indicative of the next state associated with the respective one of the state transitions, entry actions associated with the current state, and exit conditions associated with the respective one of the state transitions. Storing the state machine in the form of a state transition table with transition-specific entries is merely one example of a format for storing the state machine, and other storage formats may be used.

Memory 34 may include any volatile or non-volatile media, such as a random access memory (RAM), a read only memory (ROM), a non-volatile RAM (NVRAM), electrically erasable programmable ROM (EEPROM), flash memory, and the like. Memory 34 may store instructions for execution by processor 32 and information defining delivery of electrical stimulation to patient 14, such as, but not limited to, therapy programs (e.g., sets of stimulation parameter values) or therapy program groups, information associating therapy programs with one or more sleep stages, and any other information regarding the delivery of therapy to patient 14. Therapy information may be recorded in memory 34 for long-term storage and retrieval by a user. Memory 34 may include separate memories for storing information, such as separate memories for therapy programs, diagnostic information, target tissue site information, and patient information. In some examples, memory 34 stores program instructions that, when executed by processor 32, cause IMD 16 and/or processor 32 to perform the functions attributed to them herein.

Memory 34 may be considered, in some examples, a non-transitory computer-readable storage medium comprising instructions that cause one or more processors, such as, e.g., processor 32, to implement one or more of the example techniques described in this disclosure. The term "non-transitory" may indicate that the storage medium is not embodied in a carrier wave or a propagated signal. However, the term "non-transitory" should not be interpreted to mean that memory 34 is non-movable. As one example, memory 34 may be removed from IMD 16, and moved to another device. In certain examples, a non-transitory storage medium may store data that can, over time, change (e.g., the non-transitory storage medium may be a RAM).

In some examples, memory 34 may include a memory that is configured to store firmware code that executes on IMD 16. The firmware code may be generic, state machine-independent firmware code. For example, the firmware code may implement the state machine runtime environment described in this disclosure that is configurable to implement a variety of different state machines depending on programmable state parameters that are received from an external device. Using a state machine runtime environment that operates based on downloadable state parameters may allow, in some examples, different state machines to be implemented on IMD 16 at different times with the same generic, state machine-independent firmware code executing on IMD 16. In this way, the techniques of this disclosure may allow IMD developers and/or users to program, change, and/or download new closed-loop control policy algorithms during the operational lifespan of IMD 16 without requiring new firmware code to be downloaded onto IMD 16.

In some examples, the firmware code may be stored in a non-volatile memory such as, e.g., an EEPROM. Processor 32 may execute the firmware code that is stored in memory 34. In some cases, the portion of memory 34 that stores the firmware code may be integrated on the same microchip and/or die as processor 32.

In further examples, the firmware code may include code that is configured to implement one or more of the classifiers described in this disclosure. Again, each of the classifiers may be configured to detect and/or classify one or more states of patient 14.

Stimulation generator 36 is configured to generate stimulation pulses or waveforms, and to switch the stimulation across different electrode combinations in response to control signals received from processor 32. In some examples, stimulation generator 36 may include stimulation generation circuitry that generates the stimulation pulses and waveforms, and a switch array that switches stimulation across different electrode combinations. Stimulation generator 36 may produce an electrical stimulation signal in accordance with a program based on control signals from processor 32.

Stimulation generator 36 is electrically coupled to electrodes 20 via conductors included in lead 18 (e.g., conductors included in lead segments 28, 30). If one or more housing ("case" or "can") electrodes are provided, stimulation generator 36 may also be electrically coupled to such an electrode via an electrical conductor disposed within housing 24 of IMD 16. A can electrode may be configured as a regulated or unregulated electrode to form an electrode configuration in conjunction with other electrodes 20 located on lead 18.

In some examples, stimulation generator 36 may include a charging circuit that selectively applies energy from power source 44 to a capacitor module for generation and delivery of a supply voltage for generation of a stimulation signal. In addition to capacitors, the capacitor module may include switches. In this manner, the capacitor module may be configurable, e.g., based on signals from processor 32, to store a desired voltage for delivery of stimulation at a voltage or current amplitude specified by a program. For delivery of stimulation pulses, switches within the capacitor module may control the widths of the pulses based on signals from processor 32.

Stimulation generator 36 may be configured to deliver any type of electrical stimulation via electrodes 20. The different types of electrical stimulation may include regulated currents, unregulated currents, regulated voltages and unregulated voltages via electrodes 20. For each of the different electrodes 20, stimulation generator 36 may be configured to deliver the same type or a different type of electrical stimulation.

Electrical sensing module 38 is configured to sense one or more electrical signals indicative of activity within brain 12 of patient 14. In some cases, electrical sensing module 38 may use one or more of electrodes 20 disposed on lead 18 as sense electrodes in order to sense the electrical signals. In other cases, electrical sensing module 38 may use one or more additional electrodes that are not disposed on lead 18 (e.g., electrodes disposed on IMD 16 or another lead) to sense the electrical signals. In some cases, electrical sensing module 38 may include one or more sensors and/or may be a subset of sensors 40.

Example electrical signals that may be sensed by electrical sensing module 38 include LPF signals, ECG signals, EMG signals, microelectrode recordings (MER) signals, evoked response signals, etc. These signals may be referred to as bioelectrical signals or physiological signals. Electrical sensing module 38 may provide the sensed signals to processor 32 (e.g., classifiers executing on processor 32) for further processing.

Although FIG. 2 illustrates electrical sensing module 38 as being incorporated into a common housing with stimulation generator 36 and processor 32, in other examples, electrical sensing module 38 may be in a separate housing from IMD 16 and may communicate with processor 32 via wired or wireless communication techniques. Electrical sensing module 38 may use the same or different electrodes to sense one or more biosignals of brain 12 as that which are used to deliver electrical stimulation generated by stimulation generator 36 to patient 14.

In addition to or instead of monitoring biosignals of patient 14 via electrodes 20 included in lead 18, processor 32 may directly or indirectly receive biosignals indicative of electrical activity within brain 12 from electrodes coupled to another lead that is electrically coupled to electrical sensing module 38, biosignals from electrodes coupled to an outer housing of IMD 16 and electrically coupled to electrical sensing module 38, and/or biosignals from a sensing module that is separate from IMD 16.

Sensors 40 are configured to sense one or more electrical signals indicative of physical activity of patient 14. Sensors 40 may include, for example, inertial sensors (e.g., an accelerometer), chemical sensors, pressure sensors, temperature sensors, optical sensors, impedance sensors, bioelectrical sensors, etc. In some examples, an inertial sensor may be configured to sense and/or detect patient posture, patient activity, patient movement, patient tremor, etc. Bioelectrical sensors may include sensors that sense bioelectrical signals, such as, e.g., LPF signals, ECG signals, EMG signals, etc. The signals generated by sensors 40 may include, for examples, signals indicative of the posture of patient 14, signals indicative of the activity of patient 14, signals indicative of the acceleration of patient 14, and signals indicative of the physical movement of patient 14. IMD 16 may identify biomarkers in detected bioelectrical signals.

In the example shown in FIG. 2, processor 32 may select one or more therapy programs from memory 34 to define the electrical stimulation delivered to patient 14 to treat symptoms of patient 14. Alternatively, programmer 22 may store one or more therapy programs, and processor 32 of IMD 16 may receive selected programs from programmer 22 via telemetry module 42. For example, a processor in programmer 22 may select one or more therapy programs from a memory in programmer 22 and transmit the selected therapy program(s) to processor 32, which may then control stimulation generator 36 to deliver therapy according to the selected therapy program(s).

As described above, in the case of electrical stimulation therapy, each of the programs stored in memory 34 may include respective values for a plurality of therapy parameters, such as, e.g., voltage or current amplitude, signal duration, frequency, and electrode configuration (e.g., an indication of the electrodes 20 selected to deliver stimulation and the respective polarity of the electrodes). The therapy programs stored in memory 34 may be generated using programmer 22, e.g., during an initial or follow-up programming session, and received by processor 32 from programmer 22 via telemetry module 42.

According to examples of this disclosure, processor 32 may be able to dynamically change one or more of these therapy parameters based on a state machine and based on one or more sensed states of a patient. For example, the entry actions for the states in the state machine may specify which programs are to be enabled for a given state, which therapy parameters to use for a given state, and/or what changes to make to the therapy parameters for a given state.

Telemetry module 42 is configured to send information to and receive information from one or more devices external to IMD 16. In some examples, telemetry module 42 may use radio frequency (RF) communication techniques to communicate between IMD 16 and one or more external devices (e.g., programmer 22). In additional examples, telemetry module 42 may use proximal inductive interaction communication techniques to communicate between IMD 16 and one or more external devices (e.g., programmer 22). Telemetry module 42 may send information to external programmer 22 on a continuous basis, at periodic intervals, or upon request by IMD 16 or programmer 22. In some examples, telemetry module 42 may be electrically coupled to an antenna to facilitate communication between IMD 16 and programmer 22.

According to examples of this disclosure, telemetry module 42 may be configured to receive from an external device (e.g., programmer 22) one or more state parameters that define at least part of the structure of a state machine. In some examples, telemetry module 42 may receive the state parameters in form of parameter values and not as part of any firmware code. Transferring the state parameters in the form of parameter values instead of firmware code may allow the state machine to be reconfigured and/or reprogrammed without requiring new firmware code to be downloaded to IMD 16 via telemetry module 42.

Power source 44 may be a non-rechargeable primary cell battery or a rechargeable battery and may be coupled to power circuitry. However, this disclosure is not limited to examples in which the power source is a battery. For example, power source 44 may comprise a supercapacitor. In some examples, power source 44 may be rechargeable via induction or ultrasonic energy transmission, and include an appropriate circuit for recovering transcutaneously received energy. For example, power source 44 may be coupled to a secondary coil and a rectifier circuit for inductive energy transfer. In additional examples, power source 44 may include a small rechargeable circuit and a power generation circuit to produce the operating power. Recharging may be accomplished through proximal inductive interaction between an external charger and an inductive charging coil within IMD 16. In some examples, power requirements may be small enough to allow IMD 16 to utilize patient motion at least in part and implement a kinetic energy-scavenging device to trickle charge a rechargeable battery. A voltage regulator may generate one or more regulated voltages using the battery power.

Figure 3:
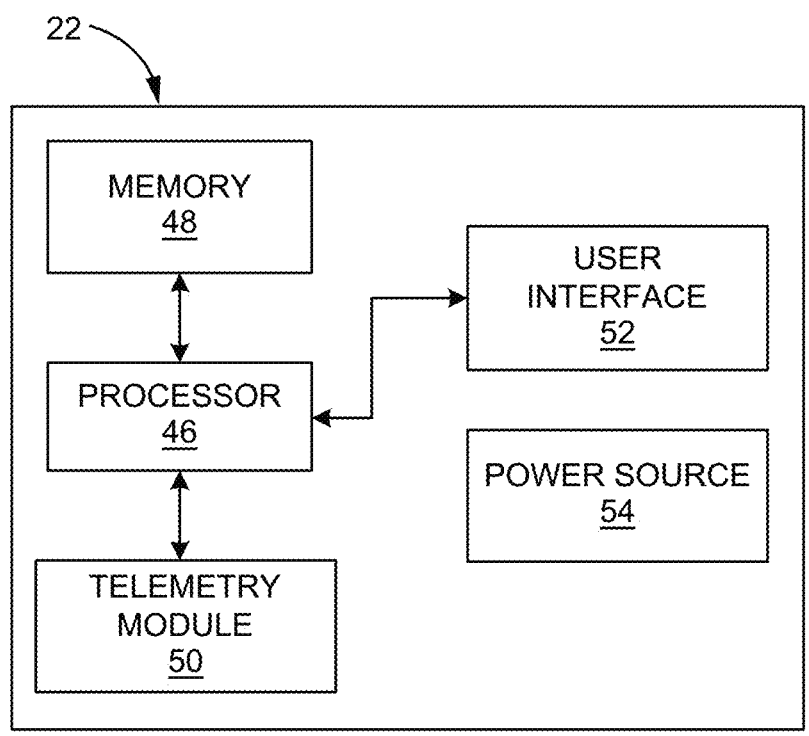
FIG. 3 is a functional block diagram illustrating an example of the external programmer of FIG. 1 in greater detail.

FIG. 3 is a functional block diagram illustrating the programmer 22 of FIG. 1 in greater detail. Programmer 22 may correspond to one or both of a patient programmer and a clinician programmer. Programmer 22 includes processor 46, memory 48, telemetry module 50, user interface 52, and power source 54. In general, processor 46 controls user interface 52, stores and retrieves data to and from memory 48, and controls transmission of data to and from IMD 16 via telemetry module 50. Processor 46 may take the form of one or more microprocessors, controllers, DSPs, ASICS, FPGAs, or equivalent discrete or integrated logic circuitry. The functions attributed to processor 46 herein may be implemented as software, firmware, hardware or any combination thereof.

Memory 48 may store instructions that cause processor 46 to provide various aspects of the functionality ascribed to programmer 22 herein. Memory 48 may include any fixed or removable magnetic, optical, or electrical media, such as RAM, ROM, CD-ROM, magnetic disks, EEPROM, or the like. Memory 48 may also include a removable memory portion that may be used to provide memory updates or increases in memory capacities. A removable memory may also allow patient data to be easily transferred to another computing device, or to be removed before programmer 22 is used to program therapy for another patient. Memory 48 may store information that controls operation of IMD 16, such as therapy delivery values. In addition, memory 48 may store state parameters received from user interface 52.

A clinician or patient 14 may interact with user interface 52 in order to, for example, manually select, change or modify programs, adjust voltage or current amplitude, provide efficacy feedback, or view stimulation data. User interface 52 may include a screen and one or more input buttons that allow external programmer 22 to receive input from a user. The screen may be a liquid crystal display (LCD), plasma display, dot matrix display, or touch screen. The input buttons may include a touch pad, increase and decrease buttons, emergency shut off button, and other input media needed to control the stimulation therapy.

Telemetry module 50 facilitates the transfer of data to and from IMD 16. Telemetry module 50 may communicate automatically with IMD 16 at a scheduled time or when the telemetry module 50 detects the proximity of IMD 16. Alternatively, telemetry module 50 may communicate with IMD 16 when signaled by a user through user interface 52. To support RF communication, telemetry module 50 may include appropriate electronic components, such as amplifiers, filters, mixers, encoders, decoders, and the like.

Programmer 22 may communicate wirelessly with implantable IMD 16 using, for example, RF communication or proximal inductive interaction. This wireless communication is possible through the use of telemetry module 50 which may be coupled to an internal antenna or an external antenna. Telemetry module 50 may be similar to telemetry module 50 of implantable IMD 16.

Programmer 22 may also be configured to communicate with another computing device via wireless communication techniques, or direct communication through a wired, e.g., network, connection. Examples of local wireless communication techniques that may be employed to facilitate communication between programmer 22 and another computing device include RF communication based on the 802.11 or Bluetooth specification sets, infrared communication, e.g., based on the IrDA standard.

Power source 54 delivers operating power to the components of programmer 22. Power source 54 may be a rechargeable battery, such as a lithium ion or nickel metal hydride battery. Other rechargeable or conventional batteries may also be used. In some cases, external programmer 22 may be used when coupled to an alternating current (AC) outlet, i.e., AC line power, either directly or via an AC/DC adapter. Power source 54 may include circuitry to monitor power remaining within a battery. In this manner, user interface 52 may provide a current battery level indicator or low battery level indicator when the battery needs to be replaced or recharged. In some cases, power source 54 may be capable of estimating the remaining time of operation using the current battery.

According to examples of this disclosure, user interface 52 of programmer 22 may be configured to receive one or more state parameters that define at least part of a structure of a state machine that generates one or more therapy decisions based on one or more sensed states of patient 14. In general, user interface 52 may implement any of the user interfaces described in this disclosure as well as other graphical user interfaces and/or text-based user interfaces for receiving state parameters.

In response to receiving the state parameters, telemetry module 50 of programmer 22 may transfer and/or download the received state parameters to IMD 16. The state parameters may, in some examples, be transferred in the form of parameter values instead of firmware code. In this way, a control policy algorithm for IMD 16 may be able to be programmed and/or reconfigured by an external device without requiring new firmware code to be reloaded onto IMD 16.

In some examples, user interface 52 may provide state-specific data entry dialog boxes that allow a user to enter one or more state parameters associated with a particular state. For example, a user may be able to specify state parameters for a particular state that control entry actions for the state and/or exit conditions for the state. Providing state-specific data entry dialog boxes may allow users to easily and efficiently enter state parameters into user interface 52 for programming control policy algorithms.

In further examples, user interface 52 may provide an interactive, graphical representation of a state diagram along with interactive state diagram components. For example, user interface 52 may graphically represent states nodes and transition arcs (e.g., arrows) connecting the state nodes. In such examples, user interface 52 may allow users to add and delete state nodes to the state diagram, to add and delete state transition arcs to the state diagram, and to position the state nodes and state transition arcs on a display. In some cases, user interface 52 may allow users to manipulate the state diagram components using drag and drop functionality. In further cases, user interface 52 may allow users to interactively join different states with state transition arcs to generate next state relationships between the different states. In additional cases, user interface 52 may provide a state-specific dialog box in response to the user clicking on a state. A user interface that includes an interactive, graphical state diagram may provide an intuitive interface for users to configure and build a state machine.

In other examples, user interface 52 may provide an interactive table or matrix representation of a state diagram.

Figure 30:
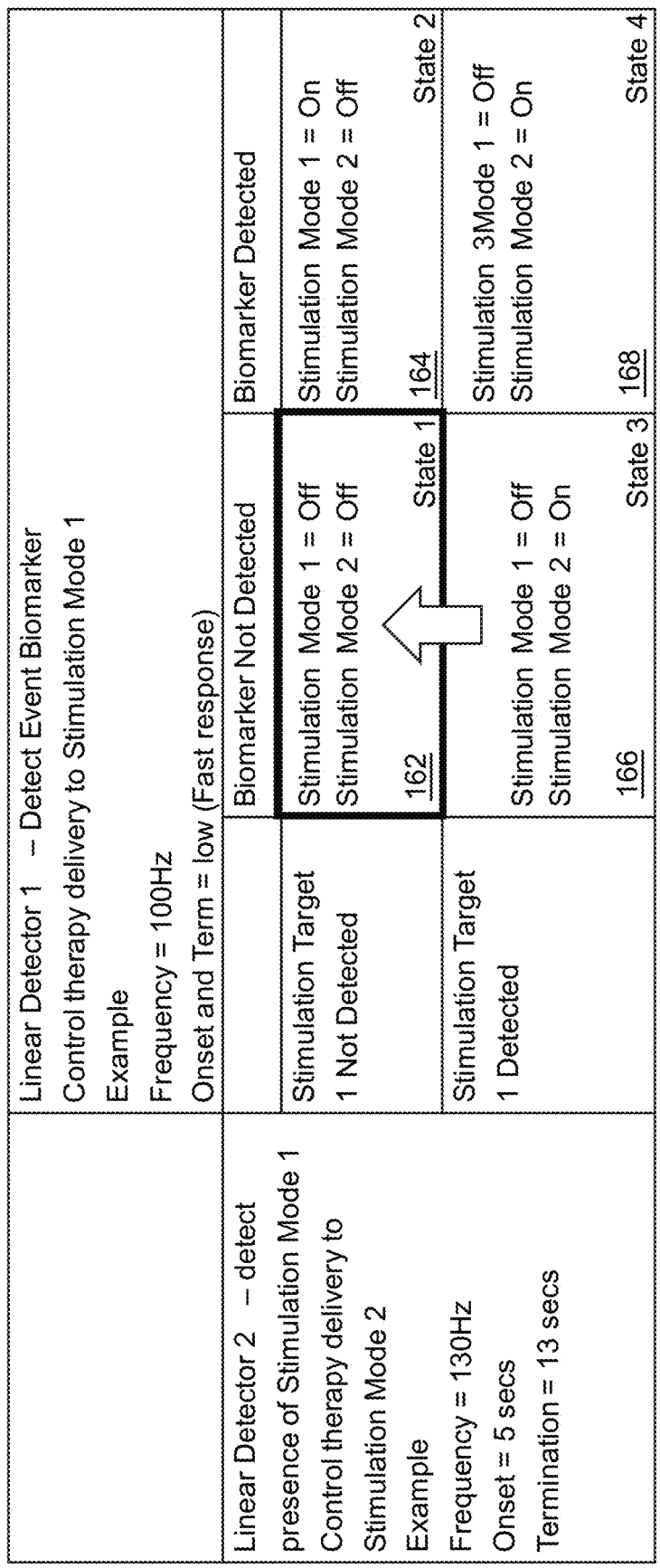
FIG. 30 is a table illustrating an example of the closed loop state diagram of FIG. 17 corresponding to a transition from the third state (State 3) to the first state (State 1).

For instance, user interface 52 may present to a user tables, such as those shown in FIGS. 11, 15, and 30 as a way for a user to program IMD 16.

Figure 4:
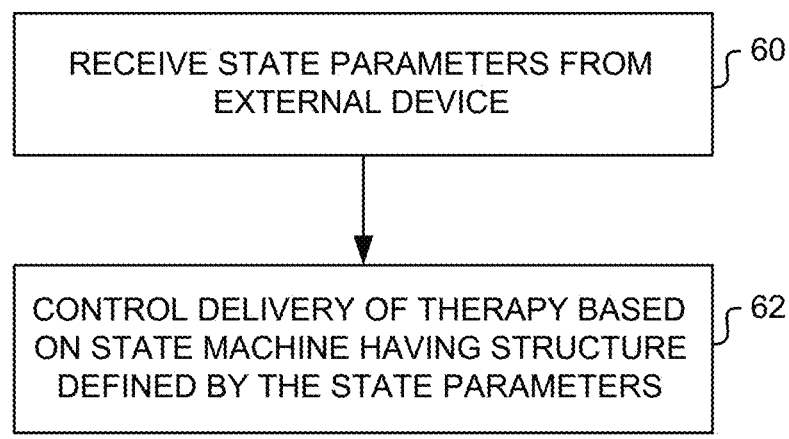
FIG. 4 is a flow diagram illustrating a technique for controlling the delivery of neurostimulation therapy by an IMD according to examples of this disclosure.

FIG. 4 is a flow diagram illustrating an example technique for controlling the delivery of therapy by a medical device according to techniques of this disclosure. The example technique shown in FIG. 4 may be used in any of the implantable medical devices described in this disclosure as well as in other implantable and non-implantable medical devices.

IMD 16 receives one or more programmable state parameters from an external device (60). The external device may be a device other than IMD 16 (e.g., programmer 22). IMD 16 controls the delivery of therapy by IMD 16 to patient 14 based on a state machine having a structure that is defined at least in part by the one or more programmable state parameters (62). The state machine may generate one or more therapy decisions based on one or more sensed states of patient 14.

Figure 5:
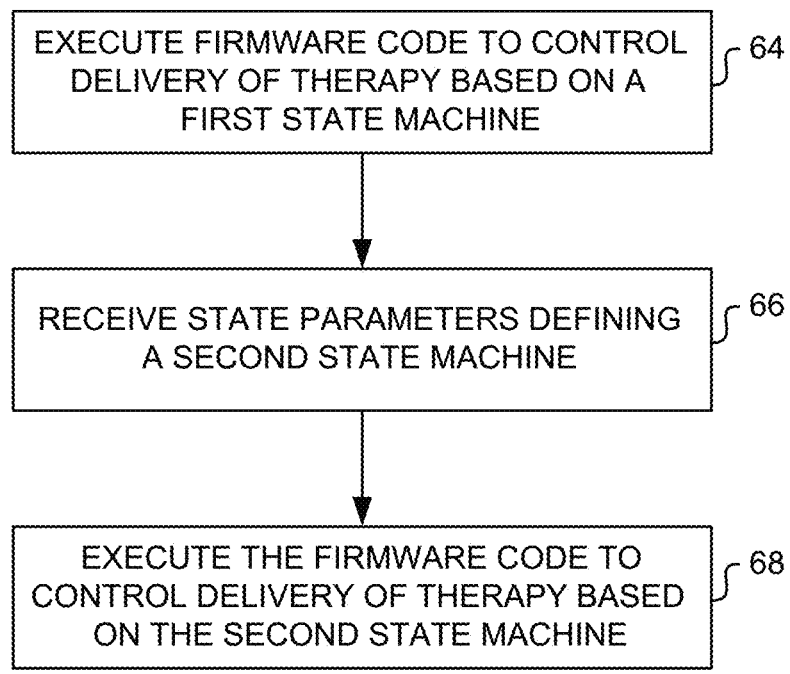
FIG. 5 is a flow diagram illustrating another technique for controlling the delivery of neurostimulation therapy by an IMD according to examples of this disclosure.

FIG. 5 is a flow diagram illustrating another example technique for controlling the delivery of therapy by a medical device according to techniques of this disclosure. The example technique shown in FIG. 5 may be used in any of the implantable medical devices described in this disclosure as well as in other implantable and non-implantable medical devices.

IMD 16 executes firmware code to control the delivery of therapy based on a first state machine (64). IMD 16 receives one or more state parameters from a device other than IMD 16 (66). In some examples, the device other than IMD 16 may be programmer 22. The one or more state parameters may define a second state machine (e.g., define a structure of the second state machine). The second state machine may be different than the first state machine. For example, the structure of the second state machine may be different than the structure of the first state machine. In some examples, the structure of a state machine may refer to one or more of the following: the number of states in the state machine, the configuration of state transitions that occur between the different states in the state machine, the entry actions for each of the states in the state machine, and/or the exit conditions for each of the states in the state machine.

IMD 16 executes firmware code to control the delivery of therapy based on the second state machine (68). The firmware code that is used to control delivery of therapy based on the second state machine may be the same firmware code that is used to control delivery of therapy based on the first state machine. For example, the firmware code may implement a generic, state-machine independent state machine runtime environment as described in examples of this disclosure. Example state machine runtime environments are described in this disclosure, for instance, with respect to FIGS. 6-9.

In some cases, the firmware code may be configurable to implement a plurality of different state machines. The state machine that is implemented by the firmware code may have a structure that is defined by the programmable state parameters.

Figure 6:
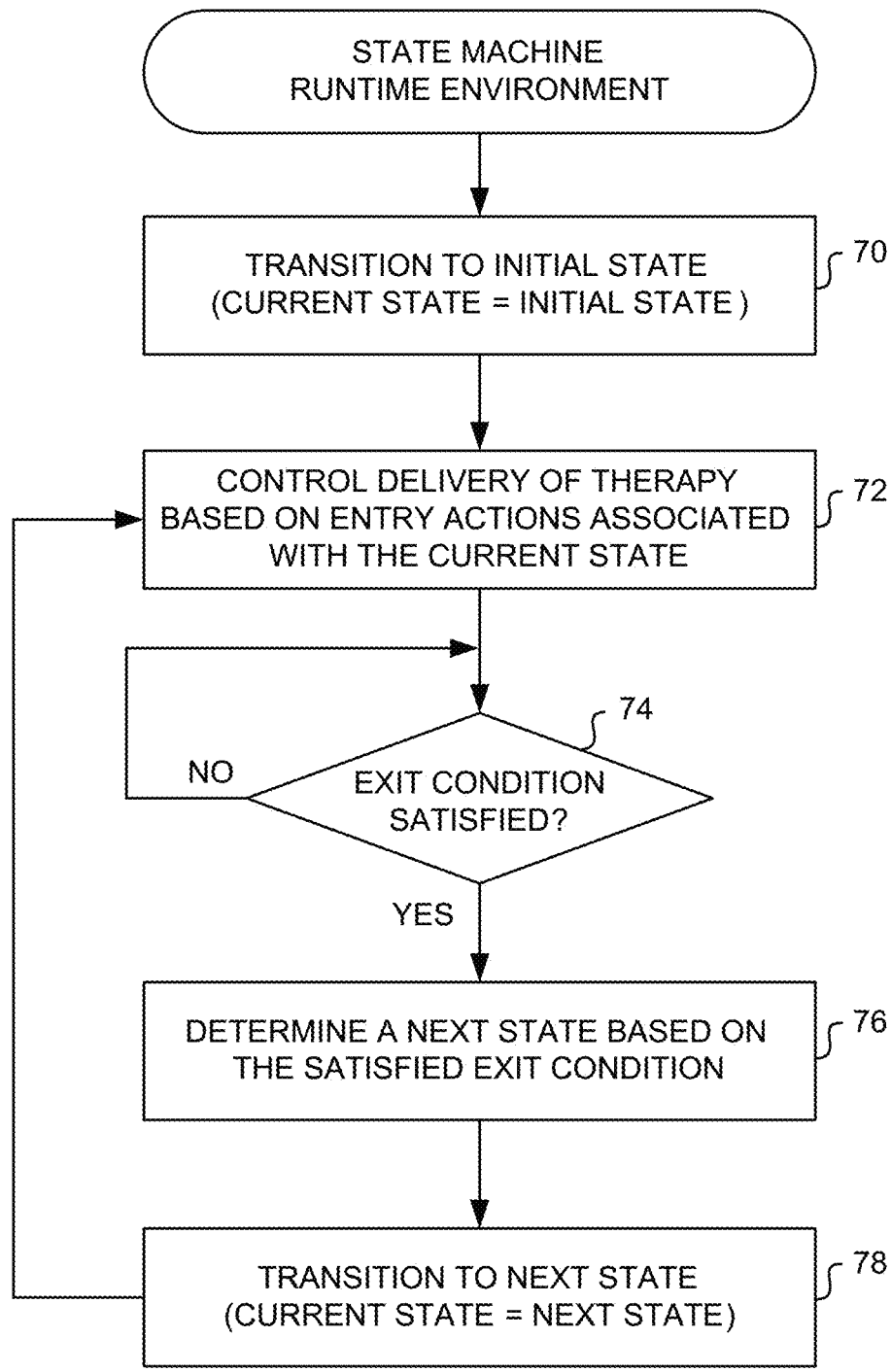
FIG. 6 is a flow diagram illustrating an example state machine runtime environment that may be implemented in an IMD according to techniques of this disclosure.

FIG. 6 is a flow diagram illustrating an example state machine runtime environment according to techniques of this disclosure. In some examples, state machine runtime environment may be implemented in firmware that is stored in IMD 16 (e.g., memory 34) and executed on IMD 16 (e.g., processor 32). In further examples, the state machine runtime environment may be hardware implemented, or any combination of hardware, software, and/or firmware.

IMD 16 transitions to an initial state of a state machine such that the initial state of the state machine becomes the current state (70). IMD 16 controls the delivery of therapy by IMD 16 based on one or more entry actions that are associated with the current state in the state machine (72). The one or more entry actions associated with the current state may be specified by programmable state parameters that are received from an external device (e.g., programmer 22).

IMD 16 determines whether one or more exit conditions that are associated with the current state are satisfied (74). The one or more exit conditions associated with the current state may be specified by the programmable state parameters that are received from an external device (e.g., programmer 22). If at least one of the exit conditions is satisfied, IMD 16 may proceed to process box 76. If no exit conditions are satisfied, then IMD 16 may repeat decision box 74 until one of the exit conditions is satisfied. In other words, IMD 16 may continue to control the delivery therapy according to the entry actions specified for the current state and continue to determine whether any exit conditions are satisfied until at least one of the exit conditions is satisfied. In cases where a timeout is enabled, if the timeout timer expires prior to any exit conditions being satisfied, then IMD 16 may transition to a next state specified by the timeout.

In response to determining that at least one of the exit conditions is satisfied for the current state, IMD 16 determines a next state of the state machine based on the at least one of exit conditions that is satisfied (76). The next state may be associated with the exit condition that is satisfied and may be specified by the programmable state parameters that are received from an external device (e.g., programmer 22). For example, the programmable state parameters may specify a next state for each of the exit conditions, and IMD 16 may select the next state that corresponds to the exit condition that is satisfied. In some cases, one or more of the exit conditions may specify a combination of one or more sensed states of the patient that are needed to satisfy the condition.

In some examples, for at least some of the states in the state machine, the programmable state parameters may specify multiple exit conditions that are capable of being satisfied during the same processing cycle. In such examples, the programmable state parameters may specify a priority for each of the exit conditions (e.g., an order of precedence for the exit conditions). If multiple exit conditions are satisfied during the same processing cycle while operating in a particular state, then IMD 16 may select the satisfied exit condition with the highest priority as the exit condition from which to determine the next state, and determine the next state based on the selected exit condition.

In some cases, when the programmable state parameters are transferred and/or stored, the exit conditions may be transferred and/or stored in a particular order. In such cases, the order in which the exit conditions are transferred and/or stored may, in some examples, determine the priority of the exit conditions. For example, the first exit condition for a state may have the highest priority for that state and the last exit condition for a state may have the lowest priority for that state.

IMD 16 transitions to the next state associated with the satisfied exit condition such that the next state becomes the current state (78). IMD 16 may proceed to process box 72 where IMD 16 controls the delivery of therapy by IMD 16 based on one or more entry actions that are associated with the current state in the state machine. Processing may continue to cycle through the states of the state machine until execution of the control policy has ceased.

With respect to block 74 of FIG. 6, the exit condition may be one of determining that a patient's symptoms have been aborted or determining that a threshold amount of time has passed since IMD 16 began the delivery of therapy. If the exit condition of the patient's symptoms having been aborted is satisfied (e.g., 74, yes), then the next state of block 76 may include turning off stimulation therapy. If the exit condition of the threshold amount of time having passed since IMD 16 began the delivery of therapy is satisfied (e.g., 74, yes), then the next state of block 76 may include turning off stimulation to a first target area and turning on stimulation to a different target area or turning on stimulation to a different target area in addition to the first target area.

Figure 7:
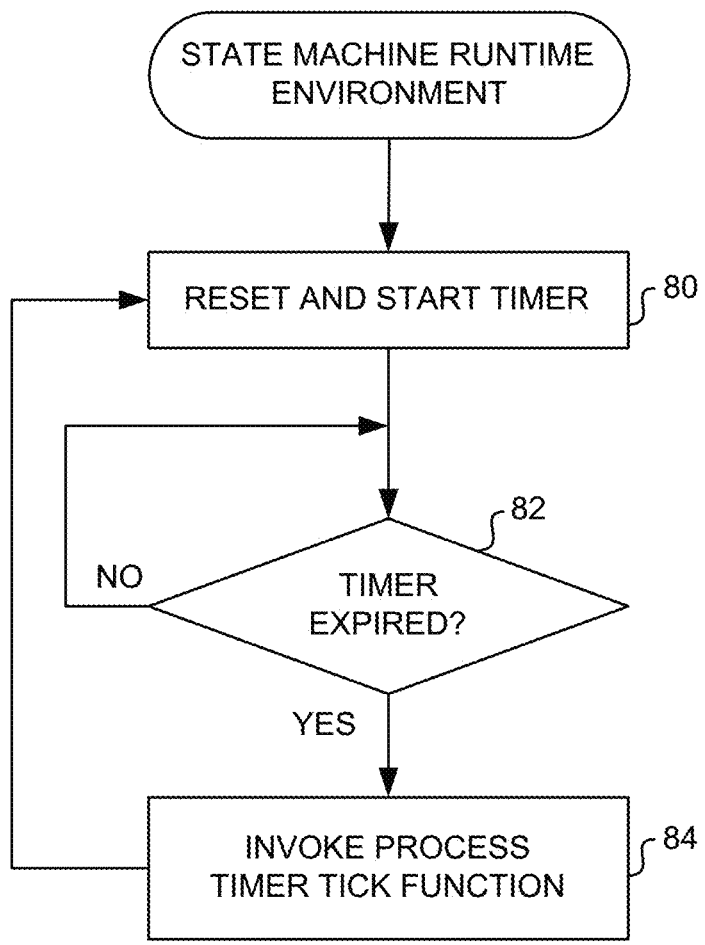
FIG. 7 is a flow diagram illustrating an example top-level process for a state machine runtime environment that may be implemented in an IMD according to techniques of this disclosure.
Figure 8:
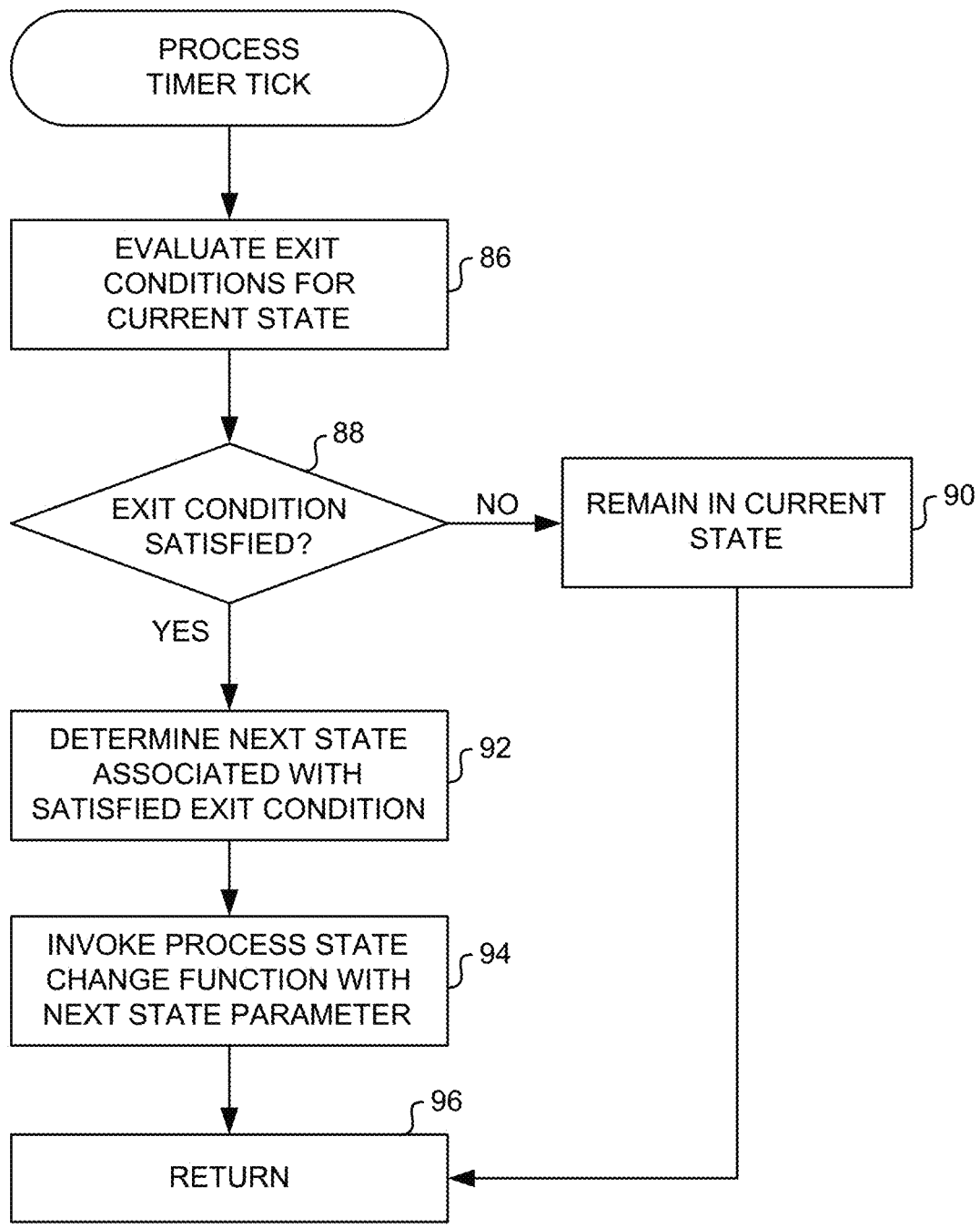
FIG. 8 is a flow diagram illustrating an example process timer tick function that may be implemented in an IMD according to techniques of this disclosure.
Figure 9:
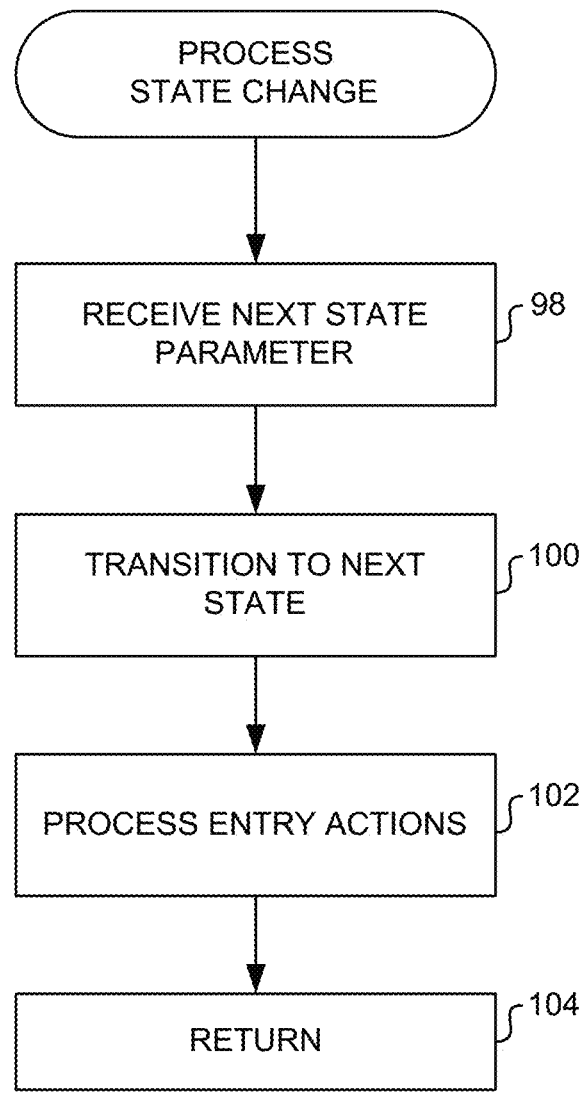
FIG. 9 is a flow diagram illustrating an example process state change function that may be implemented in an IMD according to techniques of this disclosure.

FIGS. 7-9 are flow diagrams illustrating another example state machine runtime environment according to techniques of this disclosure. In some examples, the example state machine runtime environment shown in FIGS. 7-9 may be used to implement the example state machine runtime environment illustrated in FIG. 6. The techniques shown in FIGS. 7-9 provide a modular framework for implementing a state machine runtime environment that uses callable functions to evaluate exit conditions and perform entry actions.

The state machine runtime environment shown in FIGS. 7-9 may, in some examples, be implemented in firmware that is stored in IMD 16 (e.g., memory 34) and executed on IMD 16 (e.g., processor 32). In further examples, the state machine runtime environment may be hardware implemented, or any combination of hardware, software, and/or firmware.

FIG. 7 is a flow diagram illustrating an example top-level process for an example state machine runtime environment according to techniques of this disclosure. In response to invoking execution of the state machine runtime environment, IMD 16 resets and starts a timer (80). IMD 16 determines whether the timer has expired (82). If the timer has not expired, IMD 16 repeats decision box 82 until the timer has expired. In response to the timer expiring, IMD 16 may invoke a process timer tick function (84), which is described in FIG. 8. The process timer tick function may be configured to evaluate exit conditions for a current state and cause a transition to a new state in the event that one of the exit conditions is satisfied. After invoking the process timer tick function, IMD 16 returns to process box 80 to begin a new processing cycle.

FIG. 8 is a flow diagram illustrating an example process timer tick function according to techniques of this disclosure. In some examples, the process timer tick function may be invoked as part of the example top-level process shown in FIG. 7.

IMD 16 evaluates the exit conditions for the current state (86). The exit conditions for the current state may be specified by one or more programmable state parameters received from an external device (e.g., programmer 22). IMD 16 determines if at least one of the exit conditions is satisfied (88). If no exit condition is satisfied, IMD 16 remains in the current state (90) and proceeds to process box 96, which returns processing to the top-level process for the state machine runtime environment.

If at least one exit condition is satisfied, then IMD 16 may determine a next state associated with the satisfied exit condition (92). In some examples, multiple exit conditions for a single state may be satisfied during the same processing cycle. In such examples, IMD 16 may select the exit condition with the highest priority, and determine the next state based on the selected exit condition as discussed above with respect to process box 76 of FIG. 6. For example, if the two exit conditions are determining that a patient's symptoms have been aborted and determining that a threshold amount of time has passed since IMD 16 began the delivery of therapy, then determining that a patient's symptoms have been aborted may have a highest priority. Thus, in cases where both exit conditions are satisfied, IMD 16 stops delivering therapy rather than commences delivering therapy to a second target area.

IMD 16 invokes a process state change function with the next state determined in process box 92 as an input parameter (94). The process state change function is described in FIG. 9. The process state change function may be configured to transition to a next state and perform the entry actions associated with the next state. IMD 16 returns processing to the top-level process for the state machine runtime environment (96).

FIG. 9 is a flow diagram illustrating an example process state change function according to techniques of this disclosure. In some examples, the process state change function may be invoked as part of the example process timer tick function shown in FIG. 8.

IMD 16 receives a next state parameter (98). The next state parameter may be a parameter indicative of a next state of the state machine to process. IMD 16 transitions to the next state specified by the next state parameter (100). Transitioning to the next state may include updating a current state variable and/or a current state register or may include initiating the delivery of therapy to a second target area instead of or in addition to a first target area.

IMD 16 processes the entry actions associated with the next state (102). The entry actions may be specified by one or more programmable state parameters received from an external device (e.g., programmer 22). Processing the entry actions may include performing the entry actions. IMD 16 returns processing to the process timer tick function (104).

In an embedded closed loop system the signal sampling and classifier firmware may typically operate on regular timing intervals. At a selected interval when the classifier firmware outputs are valid, state processing may be invoked by calling the "ProcessTimerTick" function. A call to this function may cause the exit conditions of the current state to be evaluated from highest priority to lowest priority (including a possible state timer expiration) to see if any classifier conditions that are not marked as don't cares are met. The first evaluated exit condition to be satisfied may cause a state transition to the assigned next state. It should be noted that when none of the conditional exit directives for a state are satisfied, the current state may remain unchanged.

When the "ProcessTimerTick" function has determined to transition to a new state the "ProcessTimerTick" function may call the "ProcessStateChange" function with the next state specified for the exit condition as a parameter. The "ProcessStateChange" function may perform the switching to the new state and process the stimulation control policies of the new state.

The entry actions for the new state and their associated parameters may include one or more of the following: a stimulation program parameter, a stimulation control parameter, an increment/decrement stimulation flags parameter, and a timer count parameter. The stimulation program parameter may specify whether the stimulation program is switched to a specified program or kept the same. The stimulation control parameter may specify an action that is to be performed with respect to the delivery of stimulation (e.g., ON, OFF or leave unchanged). The increment/decrement stimulation flags parameter may be used to set either an increment (INC) flag or a decrement (DEC) flag (or none) to be processed by another state that turns stimulation on. The timer count parameter may be loaded into the state timer. If the timer count parameter is set to 0, then the timer may be disabled (e.g., there may be no timeout from the state and the state does not transition until one of the other conditions is satisfied).

For the increment/decrement stimulation flags parameter, if stimulation is turned ON, an adjustment to the stimulation may be made immediately in response to entering a new state. If stimulation is turned OFF, then a global flag may be set (e.g., a global Increment flag or a global Decrement flag) indicating that the next time stimulation is turned ON with the same stimulation program in a subsequent processing cycle, the stimulation amplitude may either be incremented or decremented from the previous "stimulation on" value (i.e., the amplitude that was used when stimulation was previously turned ON).

If turning stimulation ON (and the stimulation program was unchanged from last state in which stimulation was ON), the INC/DEC stimulation global flags, which may have been set by a previous state, may cause the stimulation to be increased/decreased, respectively, in pre-determined voltage steps. In some cases, these flags may be mutually exclusive. Both flags may be cleared after the stimulation is turned on.

IMD 16 may execute one or more classifiers and a control policy, which may be stored as firmware code in a memory (e.g., memory 34 of FIG. 2). Characteristics of signals sensed by one or more sensors 40 may be applied to the classifiers. Outputs of the classifiers 130 may be applied as inputs to the control policy 132 to stimulation generator 36.

Sensors 40 may sense various states of a nervous system of patient 10, and stimulation generator 36 may deliver electrical stimulation in response to the sensed states, in response to state transitions detected by application of the outputs of the classifiers to the control policy. In general, the sensing may correspond to percepts, the stimulation may correspond to actions, stimulation generator 36 may correspond to effectors, and the nervous system may correspond to the environment of a state machine executed by processor 32 of IMD 16.

Sensors 40 within IMD 16 may obtain signals from the nervous system of patient 10 directly or indirectly. In some examples, sensors 40 may include an inertial sensor configured to identify patient posture, patient activity, a tremor, or the like. Additionally, or alternatively, sensors 40 may include one or more bioelectrical sensors, such as sense electrodes and associated sensing circuitry, to sense bioelectric signals such as, for example, LFP, ECG or EMG signals. LFPs may be an example of a signal sensed directly from the brain, e.g., via one or more sense electrodes carried by leads 28, 30. Inertial signals may provide a more indirect indication of brain state.

Also, in some examples, embedded within implantable stimulation generator 36, e.g., as firmware code, are algorithms to classify states (e.g., to implement the classifiers) and to control the stimulation therapy (e.g., to implement the control policy). Each of the classifiers 130 may be configured to detect and/or classify, e.g., upon execution by processor 32, whether the nervous system of patient 10 is in a particular state based on data received from one or more sensors 40 and generate data indicative of whether the particular state has been detected for the nervous system.

The control policy may be configured, e.g., upon execution by processor 32, to control the delivery of therapy by stimulation generator 36 of IMD 16 based on the sensed states of the nervous system received from the classifiers. In some examples, the control policy may be implemented by a state machine runtime environment that is configurable to implement a state machine based on one or more programmable state parameters that are received from an external device. The one or more state parameters may define at least part of the structure of the state machine. Because the same state machine runtime environment may be configurable to implement a variety of different state machines depending on the downloaded state parameters, the same generic, state machine-independent firmware code may be used to implement different state machines. In this way, the control policy algorithm for IMD 16 may be able to be programmed and/or reconfigured by an external device without requiring firmware code to be reloaded onto the IMD.

Figure 10:
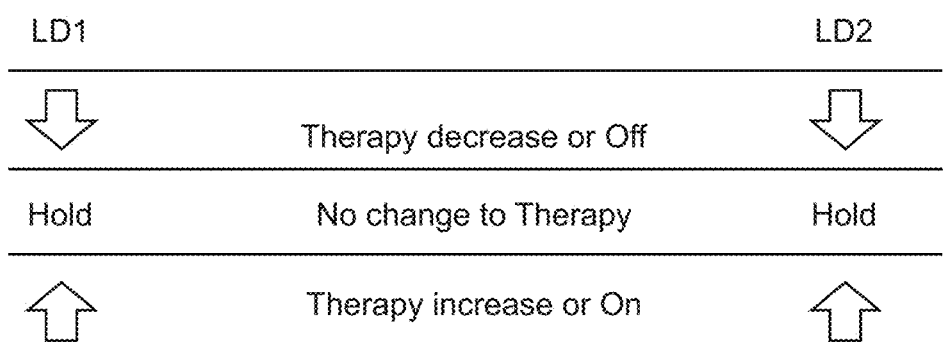
FIG. 10 is a conceptual diagram illustrating an example of a fixed table approach to state transitions.

FIG. 10 is a conceptual diagram illustrating a fixed table approach to state transitions. The fixed table approach to state transitions will be described with respect to IMD 16, but it should be understood, that in some examples, IMD 16 may implement this fixed table approach as part of a system that include other devices, such as an external device or another internal device. As shown in the example of FIG. 10, IMD 16 may be configured to deliver a first therapy based on a first linear discriminant (LD1) and a second therapy based on a second linear discriminant (LD2). If LD1 detects a biomarker that is below a first threshold and a second threshold, then IMD 16 may decrease a first therapy or turn the first therapy off. If LD1 detects a biomarker that is between a first threshold and a second threshold, then IMD 16 may hold, or not change the first therapy. If LD1 detects a biomarker that is above a first threshold and a second threshold, then IMD 16 may increase the first therapy or turn the first therapy on. If LD2 detects a biomarker that is below a first threshold and a second threshold, then IMD 16 may decrease a second therapy or turn the second therapy off. If LD2 detects a biomarker that is between a first threshold and a second threshold, then IMD 16 may hold, or not change the second therapy. If LD2 detects a biomarker that is above a first threshold and a second threshold, then IMD 16 may increase the second therapy or turn the second therapy on. The thresholds used by LD1 may be different than LD2. Additionally, the second therapy may be performed in addition to or in lieu of the first therapy.

Figure 11B:

FIGS. 11A and 11B show examples of state tables that may be used by IMD 16 to implement state transitions. The state table of FIG. 11A is a 3×3, 9-state table that utilizes two LDs, both with dual thresholds. The state table of FIG. 11A is a 3×3, 9-state table that utilizes two LDs, both with dual thresholds. The state table of FIG. 11B is a 2×2, 4-state table that utilizes two LDs, each with single thresholds. In the examples of FIGS. 11A and 11B, LB represents a lower bound for a threshold, and UB represents an upper bound for a threshold. Out represents the output of LD1 or LD2. The arrows in the lower left corners of the state boxes represent the changes to the first and second therapies, as described with respect to FIG. 10.

Figure 12:
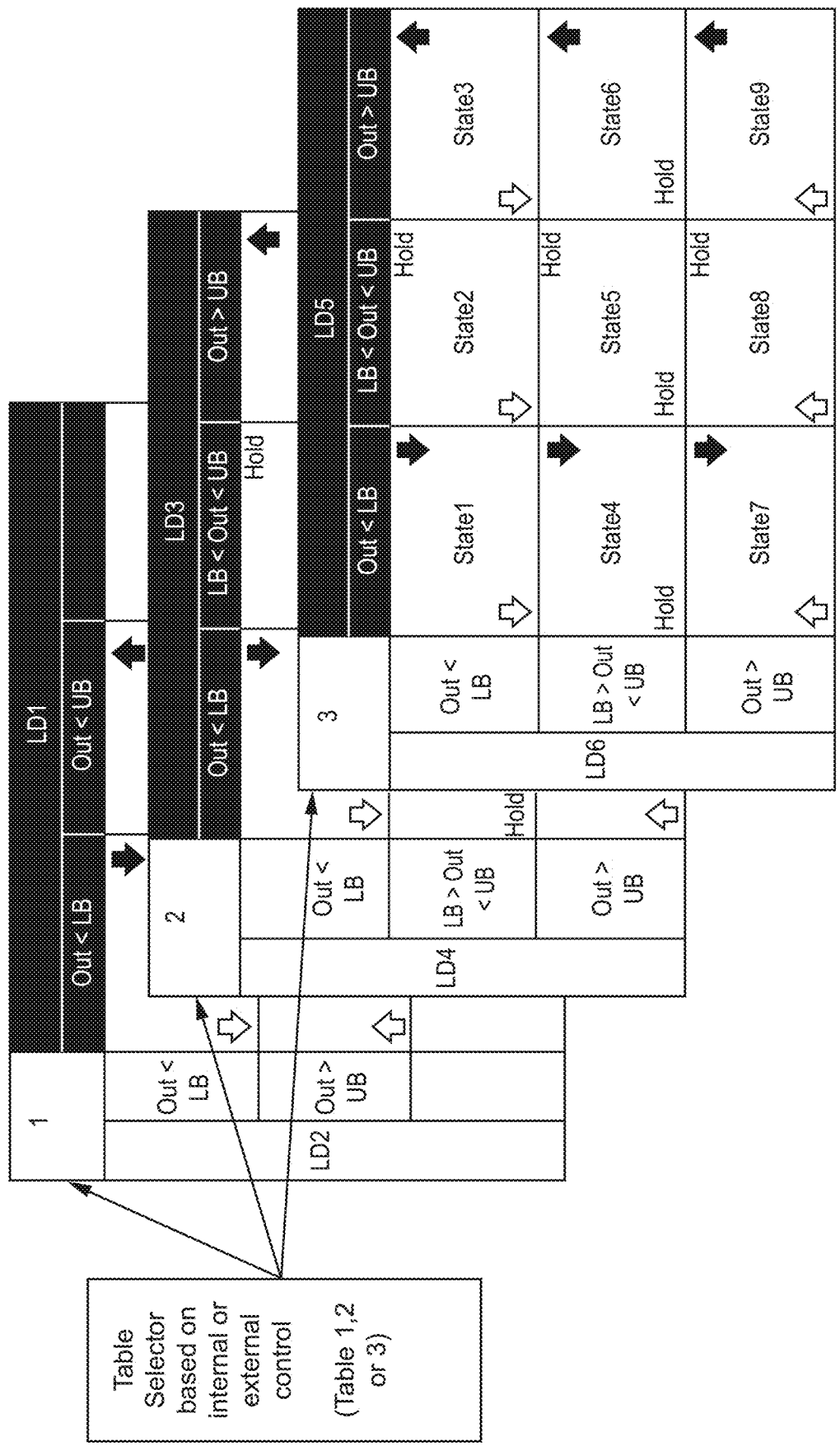
FIG. 12 shows an example of a matrix of tables, like the tables described above with respect to FIGS. 11A and 11B.

FIG. 12 shows an example of a matrix of tables, like the tables described above with respect to FIGS. 11A and 11B. IMD 16 may maintain, e.g., store or retrieve, two or more fixed tables. The example of FIG. 12 shows three tables, but two tables or more than three tables may also be used. Additionally, FIG. 12 shows 3×3 tables, but tables of other sizes may also be used and not all tables need to necessarily be the same size. IMD 16 may select one of the two or more fixed tables based on an internal or external control input. This control input may, for example, be one or more of an internal additional biomarker, a derived overall patient state (e.g., sleeping, upright and active, off meds, classified symptomatic state[seizure, dystonic. etc.]), or an external control input (e.g., from a patient activator, distributed algorithm, etc.). In this regard, based on the control input, IMD 16 may perform a 'context' switch and run a completely different policy or set of policies. IMD 16 may also use a timer to provide a fixed or set time to change states or table.

Figure 13:
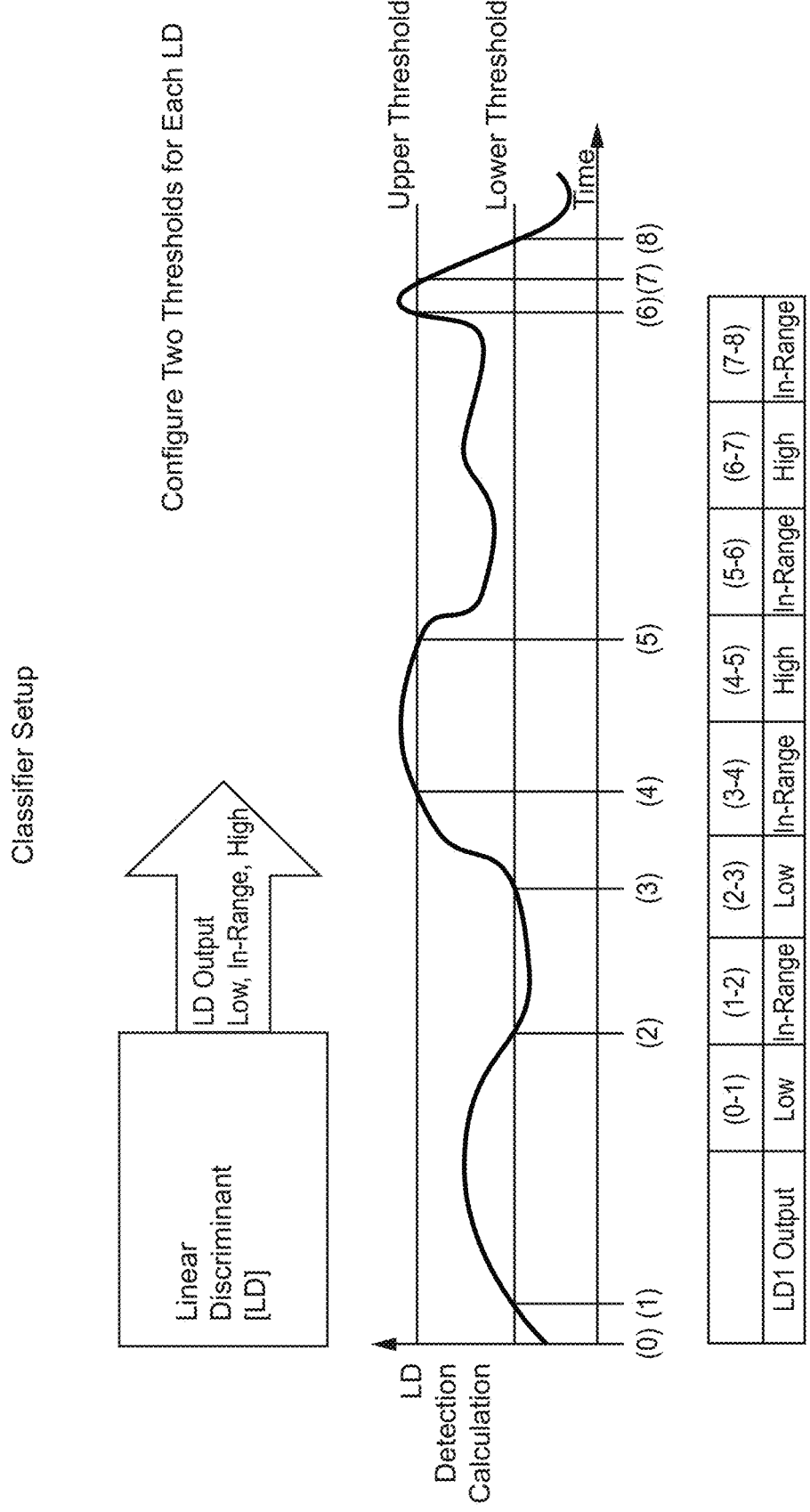
FIG. 13 shows an example of a classifier setup for a linear discriminant.

This disclosure describes examples for a table-based state machine framework. The number of possible states for this state machine framework approach may be defined by the number of unique combinations of outputs from the classifiers of the system. For example, if the system has a single classifier with an output of either IN or OUT of detect, the number of possible states would be two. In some examples described herein, there are two linear discriminants (LD) available. It should be notes that the classifiers are not required to be LDs, and could be any computational approach that yields variable output states. Two thresholds can be set for each LD, such that each LD can have a value of above the max threshold (High), below the min threshold (Low), or between the thresholds (In-Range), as shown in the example of FIG. 13.

When both LD classifiers are enabled, a total of 9 states can be achieved, as shown in FIG. 14A. Based on the output of the classifiers, the embedded closed loop algorithm may cause IMD 16 to automatically transition into the appropriate state in the state table. A duration constraint may be configured by the user, such that an LD classifier must maintain a consistent output relative to each threshold (independently) for some duration, before a state transition is allowed. These duration constraints may be known as 'onset duration' and 'termination duration', where the onset duration is the timer used when moving across the LD thresholds in the upward (positive) direction, and the termination duration is the timer used when moving across the LD thresholds in the downward (negative) direction. A single onset duration may be shared for crossing each threshold in the upward direction for a particular LD. Similarly, a single termination duration may be shared for crossing each threshold in the downward direction for a particular LD. Note that the duration constraint may be checked against each threshold independently, such that crossing one threshold does not affect the output of the other threshold. Additionally, the user can configure a single 'detection blanking timer' per LD, where the LD outputs are not evaluated after a LD state change until this detection blanking timer expires. At the point of this detection blanking timer expiring, then the onset/termination timer can start counting again for the next state change. Users may find this useful when trying to mask stimulation artifacts in sense channels, without having to slow down the onset/termination timers. It is important to note that one can use the average of some number of FFT outputs (e.g. 4) when evaluating LDs. In this case, counting for onset/termination timers may be iterated by one after each new bin of averaged FFTs (e.g. 4) are computed. Counting for the detection blanking timer in this case may still be iterated at the FFT output rate, not the averaged bin output rate. This allows the detection blanking timer to be faster than the averaged bin output rate and remains functional because the LDs are not running during detection blanking, they restart upon detection blanking timer expiration. While many users may use a single FFT output as their bin size, others may find using an average provides desired smoothing effects.

FIG. 14B shows example targets for each state of a program in FIG. 14A. For brevity, FIG. 14B only shows examples for four of the nine states of FIG. 14A. States 2, 5, 6, 7, and 8 may similarly include a variety of different parameters in the same manner that states 0, 1, 3, and 4 do. In the examples of FIGS. 14A-14C P1-P4 represent different programs that may utilize different stimulation parameters. Each state for the different programs has defined targets for each configurable stimulation parameter (amp, pw, rate, etc.) as well as the ability to indicate HOLD for a given parameter when entering a given state.

FIG. 14C shows an example of limits that may be used for setting the parameters in the P1-P4 targets of FIGS. 14A and 14B. The safe limits for amplitude (upper and lower) may be set on a per program basis. The safe limits (maximum) on rise and fall may be set on a per program basis. The safe limits (upper and lower) on rate may be configurable only for all programs. In some implementations, a pulse width may be adjustable, while in other implementations a pulse width may be adjustable within the state machine, but instead may be fixed for all programs.

Figure 15A:
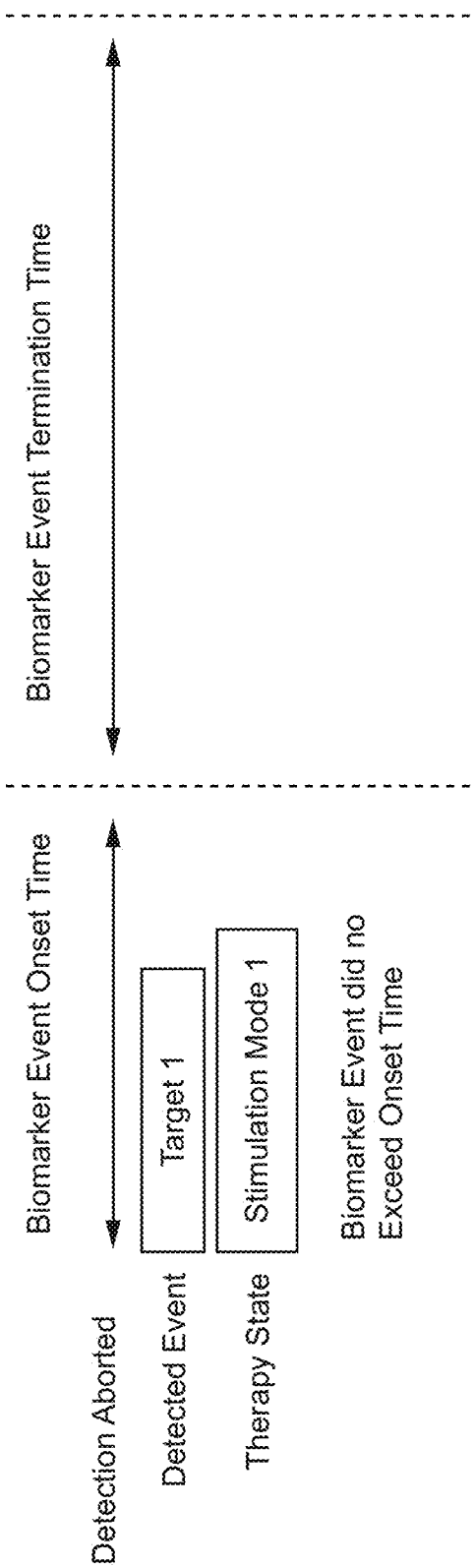
FIG. 15A is a timing map of a detection response of a multi-target adaptive neurostimulation therapy control algorithm in accordance with examples of this disclosure, illustrating aborted detection.
Figure 15B:
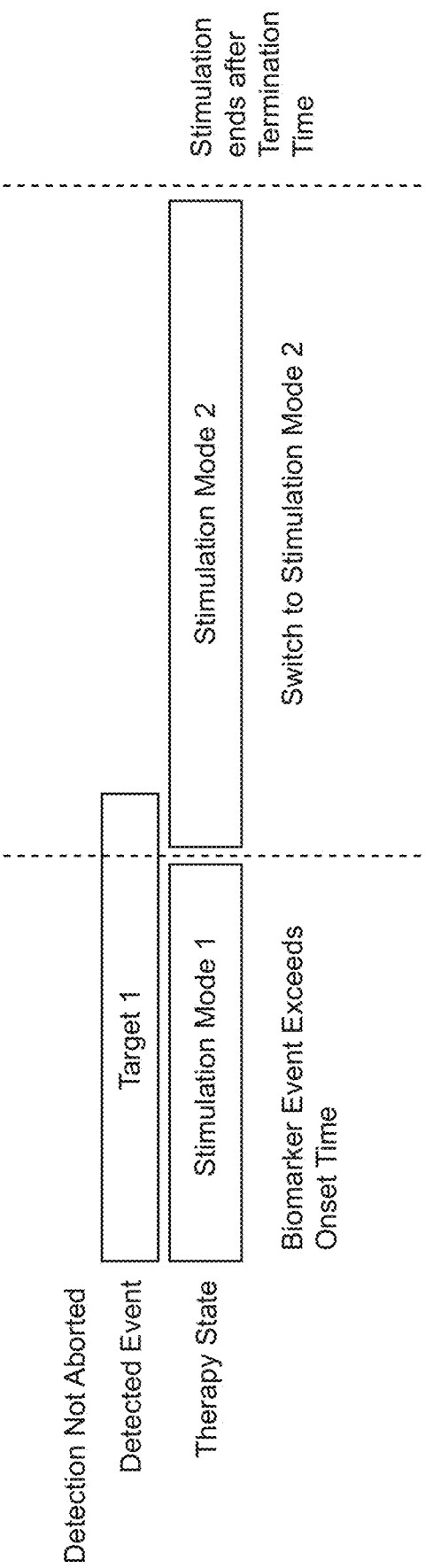
FIG. 15B is another timing map of a detection response of a multi-target adaptive neurostimulation therapy control algorithm in accordance with examples of this disclosure, illustrating non-aborted detection.

FIGS. 15A and 15B are timing maps of a detection response of a multi-target adaptive neurostimulation therapy control algorithm implemented by IMD 16 in accordance with an example of this disclosure, illustrating aborted detection and non-aborted detection, respectively. In the examples of FIGS. 15A and 15B, target 1 represents the detection of a symptom, e.g., a biomarker event in target 1. In FIG. 15A, in response to detecting an event or biomarker at a spatial target (i.e., target 1 in FIGS. 15A and 15B), IMD 16 enters stimulation mode 1, and in response to the event or biomarker detection terminating in target 1, e.g., the seizure event ceasing, before the passing of an onset time period, IMD 16 stops delivering therapy in accordance with stimulation mode 1. In FIG. 15B, in response to detecting an event or biomarker in target 1, IMD 16 enters stimulation mode 1, and in response to the biomarker detection persisting past an onset time period, IMD 16 begins delivering therapy in accordance with stimulation mode 2 and may or may not continue delivering therapy in accordance with stimulation mode 1. In FIG. 15B, all stimulation ends after a termination time, even if the event or biomarker detection in target 1 has not terminated.

Figure 16:
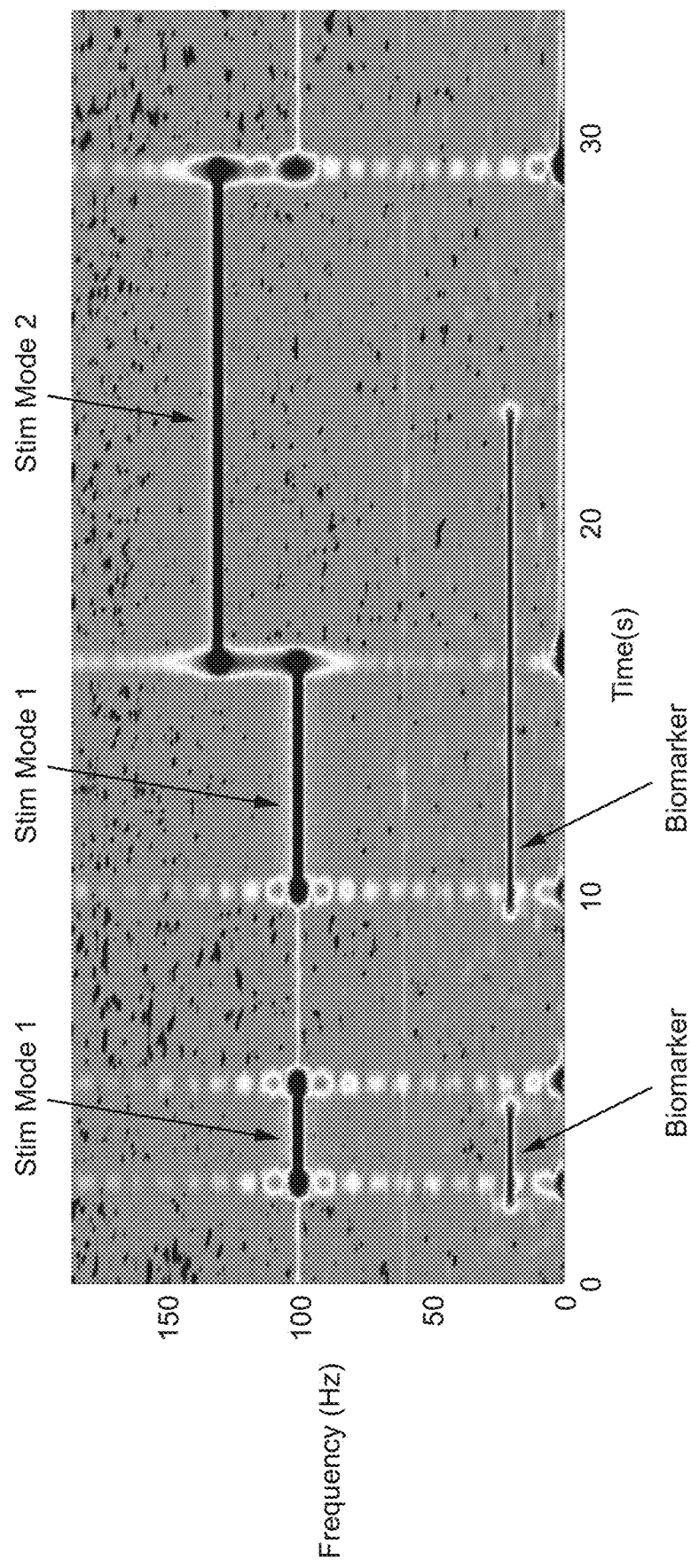
FIG. 16 is a graph illustrating an example of a spectral response during operation of a multi-target adaptive neurostimulation therapy control algorithm in accordance with examples of this disclosure.

FIG. 16 is a graph illustrating an example of a spectral response during operation of a multi-target adaptive neurostimulation therapy control algorithm in accordance with an example of this disclosure. The graph of FIG. 16 illustrates a spectral response that corresponds to the detection algorithm scenario of FIGS. 15A and 15B. In the example of FIG. 16, the graph illustrates detection of first stimulation (Stim Mode 1) at first and second time periods and at a first frequency, detection of second stimulation (Stim Mode 2) at a second time period and at a second frequency, and detection of a biomarker at first and second time periods and at a third frequency, different than the first and second frequencies. In some examples, the first and second frequencies of the first stimulation and second stimulation, respectively may be the same or different.

FIG. 17 shows an example of a closed loop state diagram with control policy actions. The closed loop state diagram of FIG. 17 shows four states. IMD 16 may include sensors, e.g., formed by at least two linear discriminants (LD1 and LD2) configured to implement the policy actions of FIG. 17. LD1 and LD2 may, for example, be bioelectric sensors. In state 1, LD1 does not detect a biomarker, and LD2 does not detect that stimulation is being performed. In state 1, both stimulation mode 1 and stimulation mode 2 are off. In state 2, LD1 detects a biomarker, and LD2 does not detect that stimulation is being performed. In state 2, stimulation mode 1 is on and stimulation mode 2 is off. In state 3, LD1 does not detect a biomarker, and LD2 detects that stimulation is being performed. In state 3, stimulation mode 1 is off and stimulation mode 2 is on. In state 4, LD1 detects a biomarker, and LD2 detects that stimulation is being performed. In state 2, stimulation mode 1 is off and stimulation mode 2 is on.

FIG. 18 is a table illustrating an example of the closed loop state diagram of FIG. 17 corresponding to a first state (State 1). In FIG. 18, LD1 does not detect a biomarker, and LD2 does not detect that stimulation is being performed, causing IMD 16 to stay in state 1, where both stimulation mode 1 and stimulation mode 2 are off. In FIGS. 18, 20, 22, 24, 26, 28, and 30, state 1 is labeled with reference numeral 162; state 2 is labeled with reference numeral 164; state 3 is labeled with reference numeral 166; and state 4 is labeled with reference numeral 168.

Figure 19:
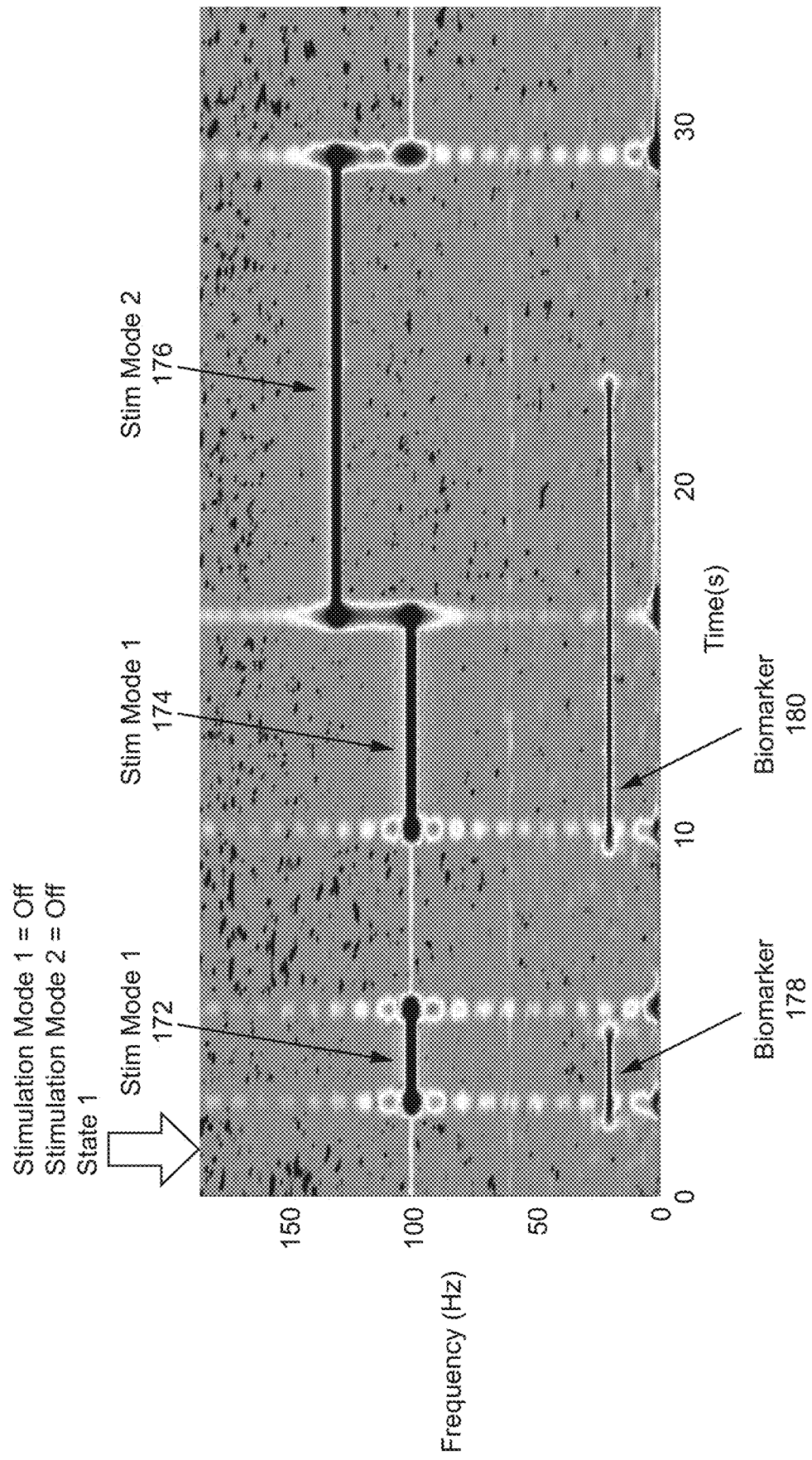
FIG. 19 is a graph illustrating an example of a spectral response during operation of multi-target adaptive neurostimulation therapy control algorithm in accordance with the example of FIG. 17.

FIG. 19 is a graph illustrating an example of a spectral response during operation of multi-target adaptive neurostimulation therapy control algorithm in accordance with the example of FIG. 18. FIG. 19 shows sensed LFP signals at different frequencies and at different delivery times. Stimulation modes 172, 174, and 176 represent the stim mode signals of what IMD 16 is delivering. Biomarker signals 178 and 180 represent observations of what the brain LFP is doing and may, for example, represent a seizure biomarker based on comparison to thresholds (e.g., low, mid or high relative to threshold). The biomarker may, for example, be an amplitude or power level of a signal in a frequency band or a ratio of amplitude or power of signals in different frequency bands, such as beta, gamma, and/or theta. The biomarker may also be identified based on comparing foreground and background ratios of amplitude or power. Additionally, the biomarker may be identified by changes in amplitude or power level or ratio of amplitude or power determined by comparing an instantaneous value or average to an ongoing average.

As one example, IMD 16 may be configured to measure the power of a sensed signal tuned in the 20-25 Hz frequency range. The 20-25 Hz frequency range represents the expected range of a biomarker, with high power content in the beta frequency range being a signature indicative of seizure and impaired motor condition.

Figure 20:
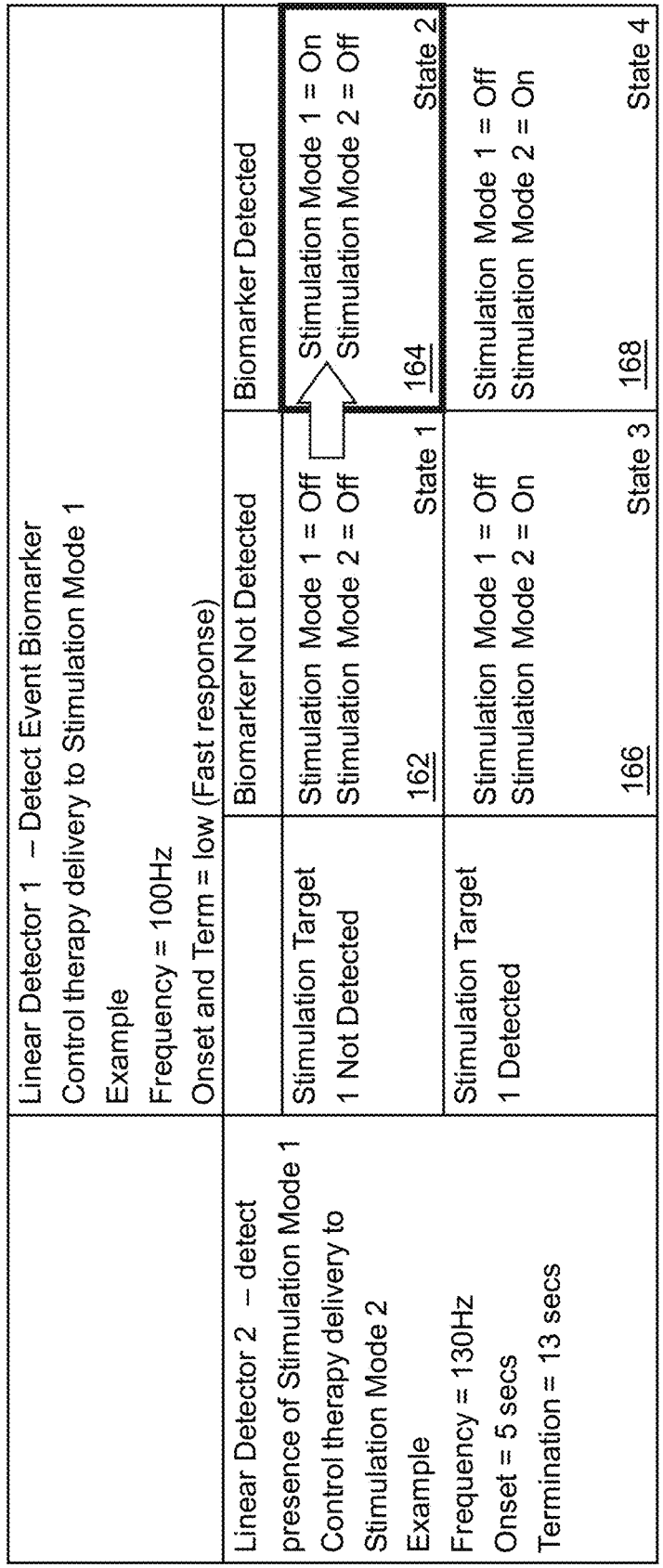
FIG. 20 is a table illustrating an example of the closed loop state diagram of FIG. 17 corresponding to a transition from the first state (State 1) to a second state (State 2).

FIG. 20 is a table illustrating an example of the closed loop state diagram of FIG. 17 corresponding to a transition from the first state (State 1) to a second state (State 2). In state 1, LD1 does not detect a biomarker, and LD2 does not detect that stimulation is being performed. In state 1, both stimulation mode 1 and stimulation mode 2 are off. In response to LD1 detecting a biomarker and LD2 not detecting that stimulation is being performed, IMD 16 transitions from state 1 to state 2. In state 2, stimulation mode 1 is on and stimulation mode 2 is off. IMD 16 may, for example, perform the state 1 to state 2 transition in response to detecting a symptom or the onset of a symptom. State 2 is labeled with reference numeral 164 in FIG. 20.

Figure 21:
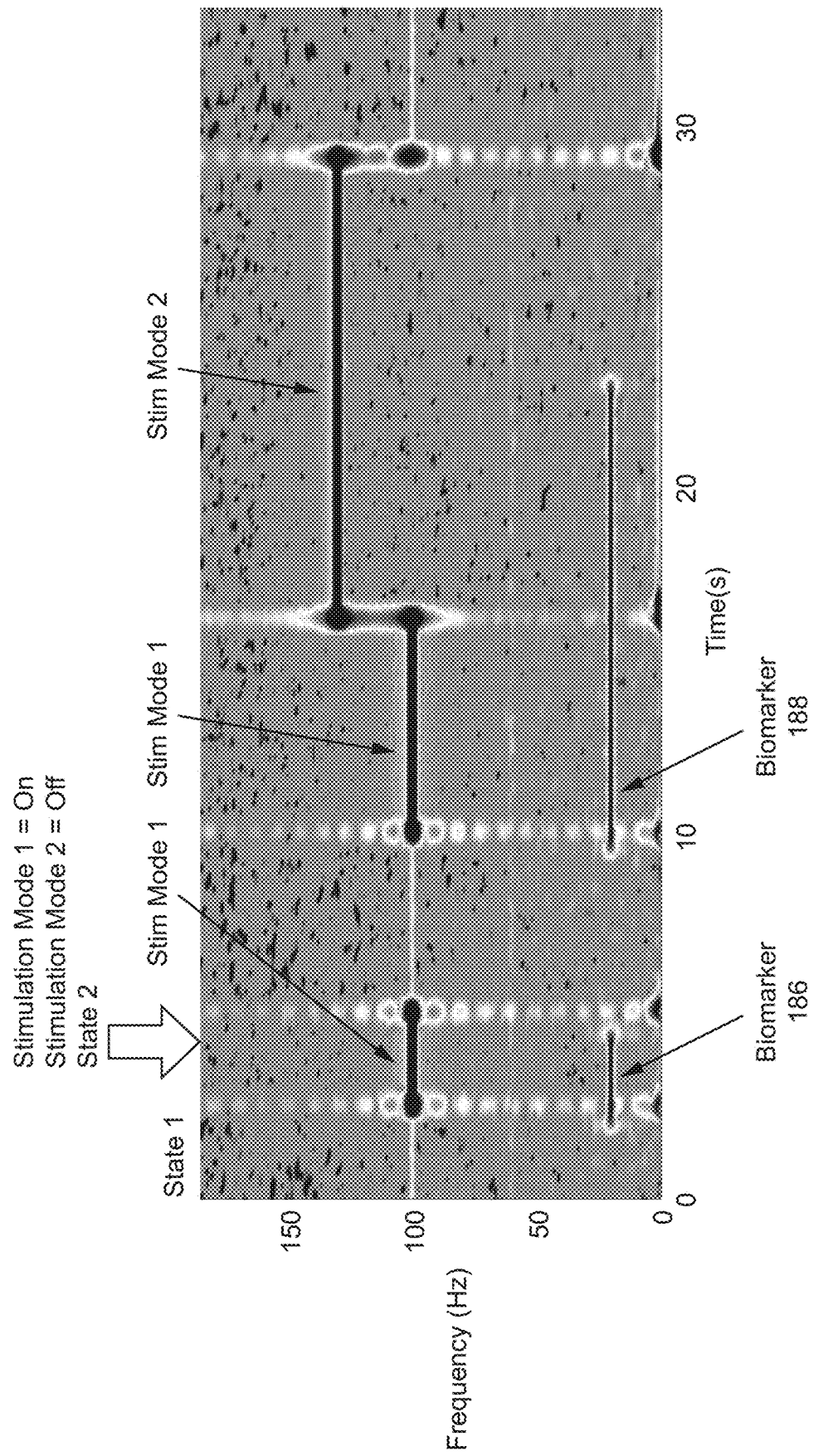
FIG. 21 is a graph illustrating an example of a spectral response during operation of multi-target adaptive neurostimulation therapy control algorithm in accordance with the example of FIG. 20.

FIG. 21 is a graph illustrating an example of a spectral response during operation of multi-target adaptive neurostimulation therapy control algorithm in accordance with the example of FIG. 20. As can be seen in FIG. 21, from time t=0 to approximately time t=1, there is no biomarker present, so neither stim mode 1 or stim mode 2 is turned on. At approximately time t=2, a biomarker 186 appears, and shortly after time t=2, stim mode 1 is turned on. Shortly before time t=5, biomarker 186 is no longer present, and shortly after time t=5, stim mode 1 is turned off. Shortly before time t=10, biomarker 188 is present, and at time t=10, stimulation mode 1 is turned on. At approximately time t=16, biomarker 188 is still present, and stim mode 1 is turned off while stim mode 2 is turned on. At time t=25, the biomarker 188 disappears, and at time 30, stim mode 2 is turned off.

Figure 22:
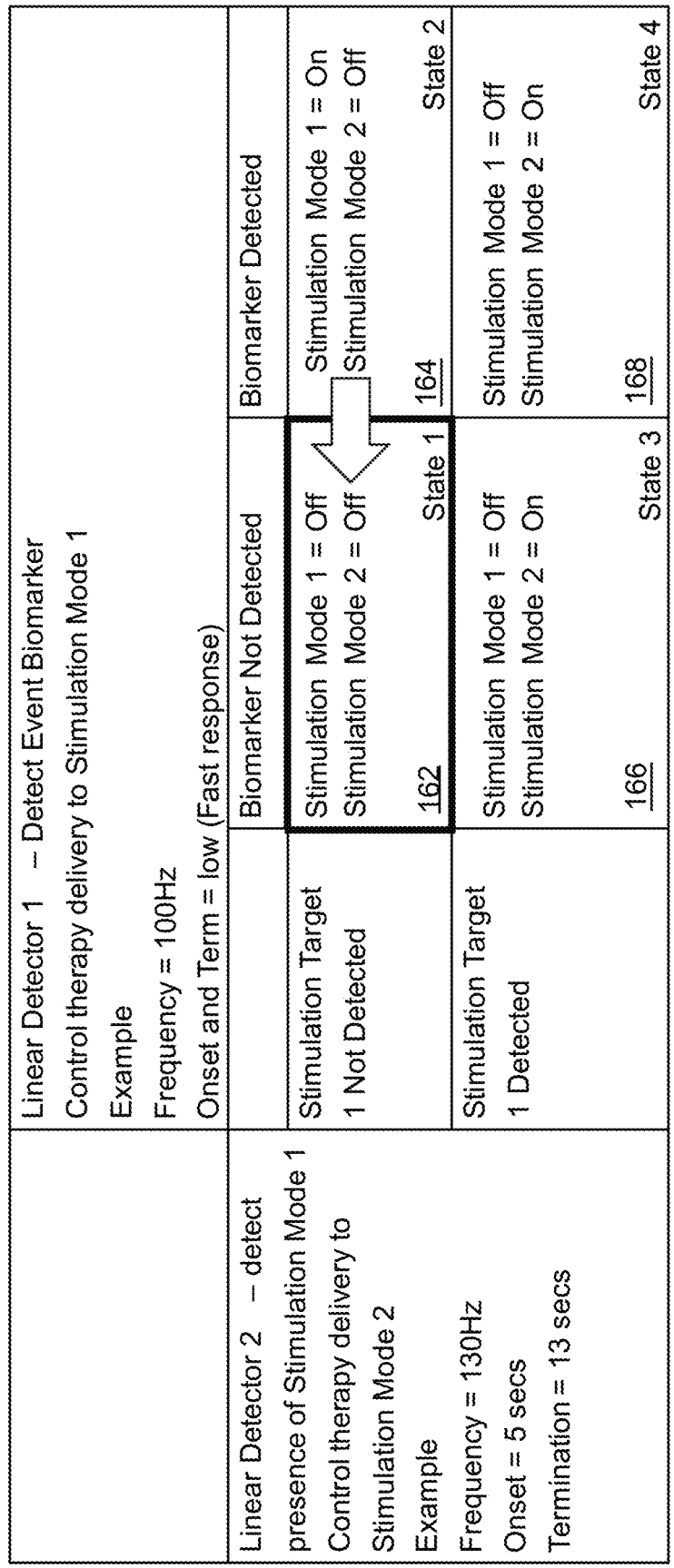
FIG. 22 is a table illustrating an example of the closed loop state diagram of FIG. 17 corresponding to a transition from the second state (State 2) to the first state (State 1).

FIG. 22 is a table illustrating an example of the closed loop state diagram of FIG. 17 corresponding to a transition from the second state (State 2) to the first state (State 1). In state 2, LD1 detects a biomarker, and LD2 detects that stimulation is being performed. In state 2, stimulation mode 1 is on and stimulation mode 2 is off. In response to LD1 no longer detecting a biomarker and LD2 detecting that stimulation is being performed, IMD 16 transitions from state 2 to state 1. In state 1, both stimulation mode 1 and stimulation mode 2 are off. State 1 is labeled with reference numeral 162 in FIG. 18.

Figure 23:
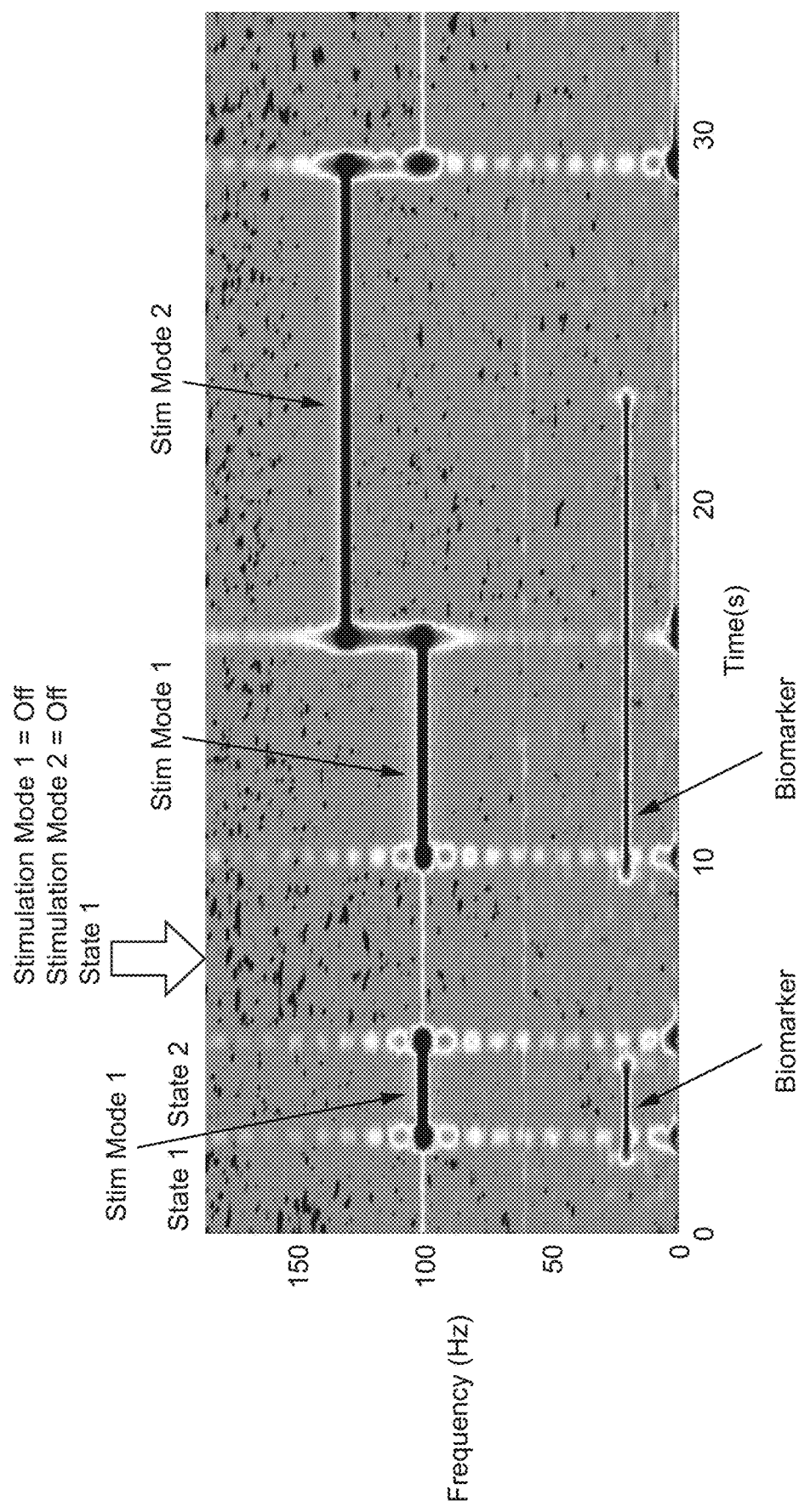
FIG. 23 is a graph illustrating an example of a spectral response during operation of multi-target adaptive neurostimulation therapy control algorithm in accordance with the example of FIG. 22.

FIG. 23 is a graph illustrating an example of a spectral response during operation of multi-target adaptive neurostimulation therapy control algorithm in accordance with the example of FIG. 22. In FIG. 23, the state 2 to state 1 transition of FIG. 22 occurs at approximately time t=6.

Figure 24:
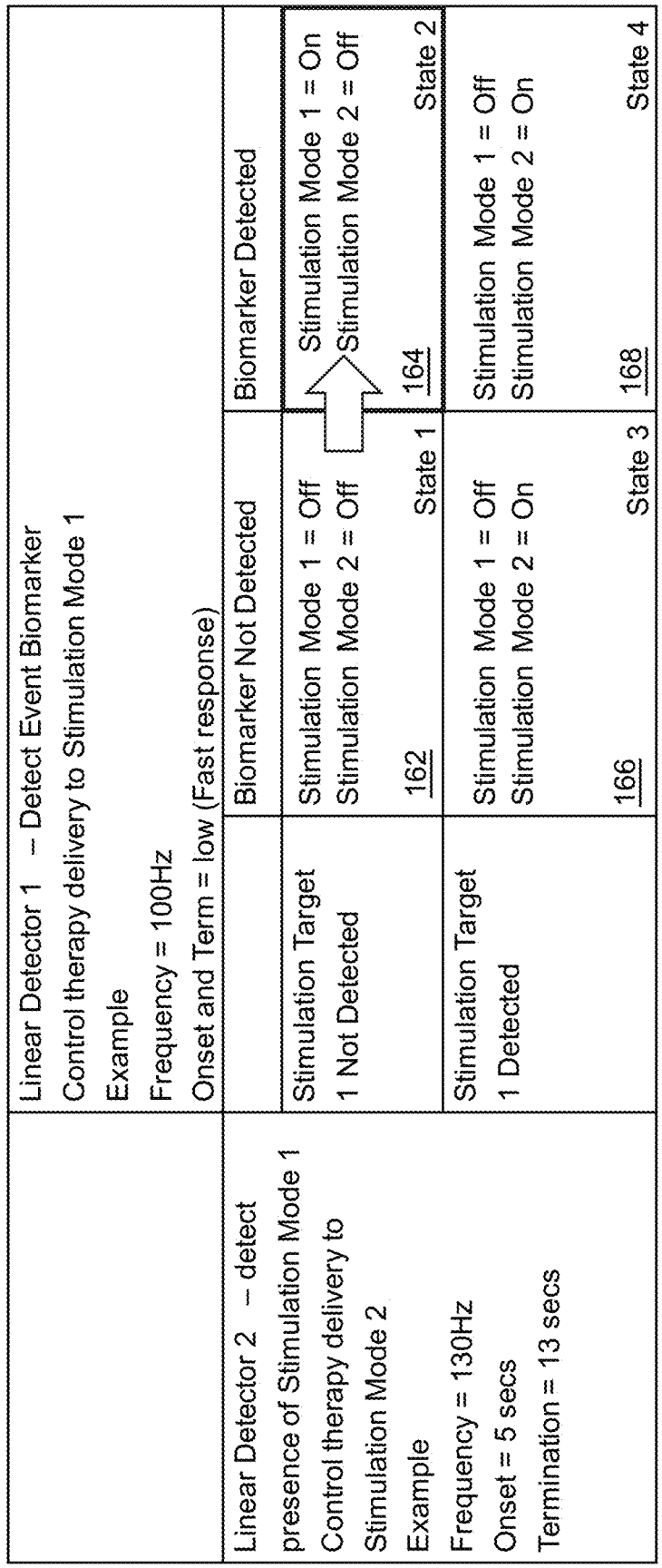
FIG. 24 is a table illustrating an example of the closed loop state diagram of FIG. 17 corresponding to another transition from the first state (State 1) to the second state (State 2).

FIG. 24 is a table illustrating an example of the closed loop state diagram of FIG. 17 corresponding to another transition from the first state (State 1) to the second state (State 2). In state 1, LD1 does not detect a biomarker, and LD2 does not detect that stimulation is being performed. In state 1, both stimulation mode 1 and stimulation mode 2 are off. In response to LD1 detecting a biomarker and LD2 not detecting that stimulation is being performed, IMD 16 transitions from state 1 to state 2. In state 2, stimulation mode 1 is on and stimulation mode 2 is off.

Figure 25:
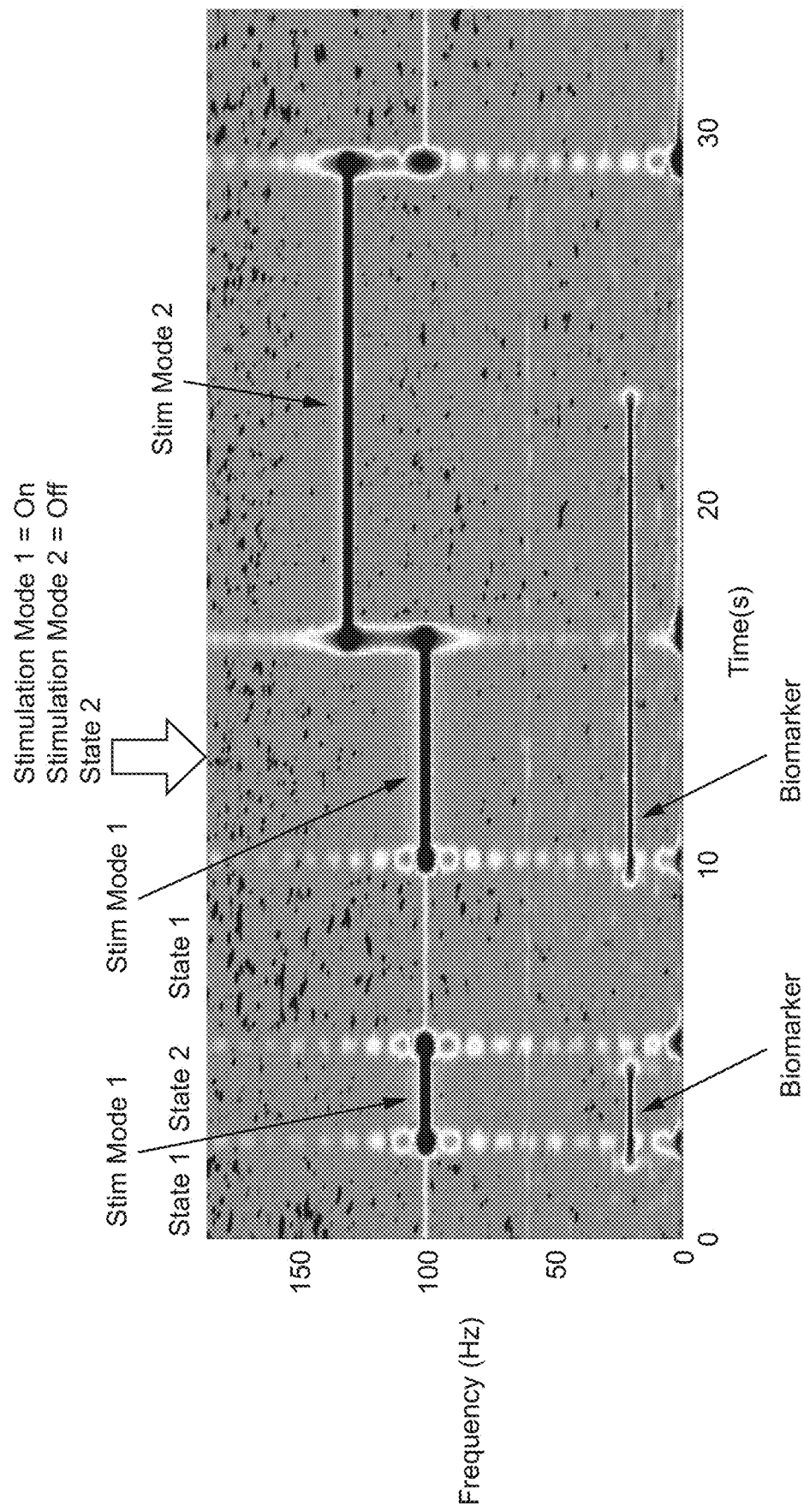
FIG. 25 is a graph illustrating an example of a spectral response during operation of multi-target adaptive neurostimulation therapy control algorithm in accordance with the example of FIG. 24.

FIG. 25 is a graph illustrating an example of a spectral response during operation of multi-target adaptive neurostimulation therapy control algorithm in accordance with the example of FIG. 24. In FIG. 25, the state 1 to state 2 transition of FIG. 24 occurs at approximately time t=10.

FIG. 26 is a table illustrating an example of the closed loop state diagram of FIG. 17 corresponding to a transition from the second state (State 2) to a fourth state (State 4). In state 2, LD1 detects a biomarker and LD2 detects that stimulation is being performed. In state 2, stimulation mode 1 is on, and stimulation mode 2 is off. In response to LD1 continuing to detect the biomarker for longer than a threshold period of time and LD2 detecting that stimulation is being performed in stimulation mode 1, IMD 16 transitions from state 2 to state 4. In state 4, stimulation mode 1 is off, and stimulation mode 2 is on. In some implementations, stimulation mode 1 and stimulation mode 2 may operate concurrently. In this context, concurrently may mean that IMD 16 performs stimulation in modes 1 and 2 in a simultaneous, interleaved, and/or overlapped manner. IMD 16 may, for example, perform the state 2 to state 4 transition in response to stimulation mode 1 not eliminating a patient's symptom.

Figure 27:
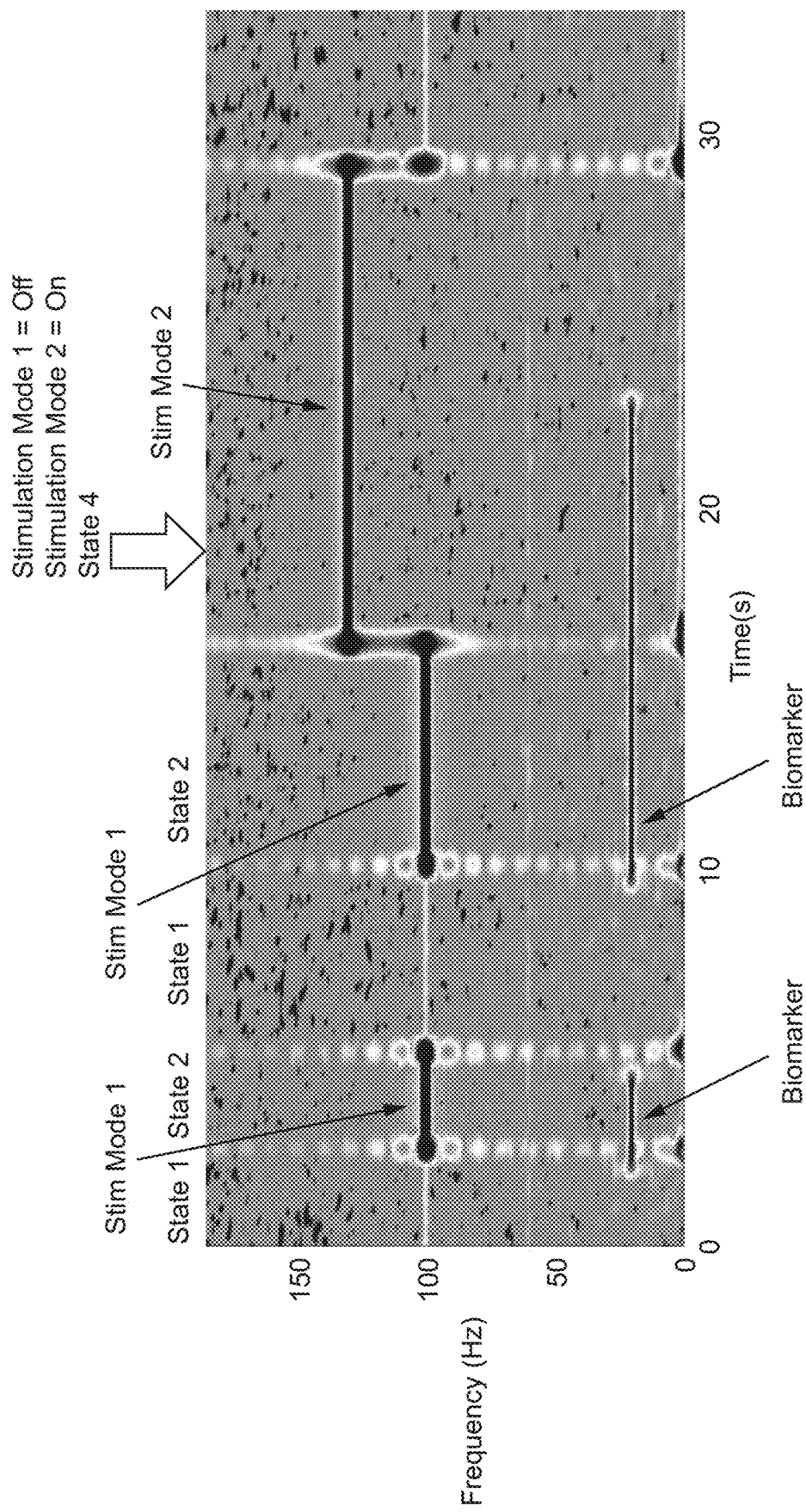
FIG. 27 is a graph illustrating an example of a spectral response during operation of multi-target adaptive neurostimulation therapy control algorithm in accordance with the example of FIG. 26.

FIG. 27 is a graph illustrating an example of a spectral response during operation of multi-target adaptive neurostimulation therapy control algorithm in accordance with the example of FIG. 26. In FIG. 27, the state 2 to state 4 transition of FIG. 26 occurs at approximately time t=16.

FIG. 28 is a table illustrating an example of the closed loop state diagram of FIG. 17 corresponding to a transition from the fourth state (State 4) to a third state (State 3). In state 4, LD1 detects a biomarker, and LD2 detects that stimulation is being performed. In state 4, stimulation mode 1 is off, and stimulation mode 2 is on. In response to, LD1 no longer detecting the biomarker and LD2 detecting that stimulation is being performed, IMD 16 can transition from state 4 to state 3. In state 3, stimulation mode 1 is off, and stimulation mode 2 is on.

Figure 29:
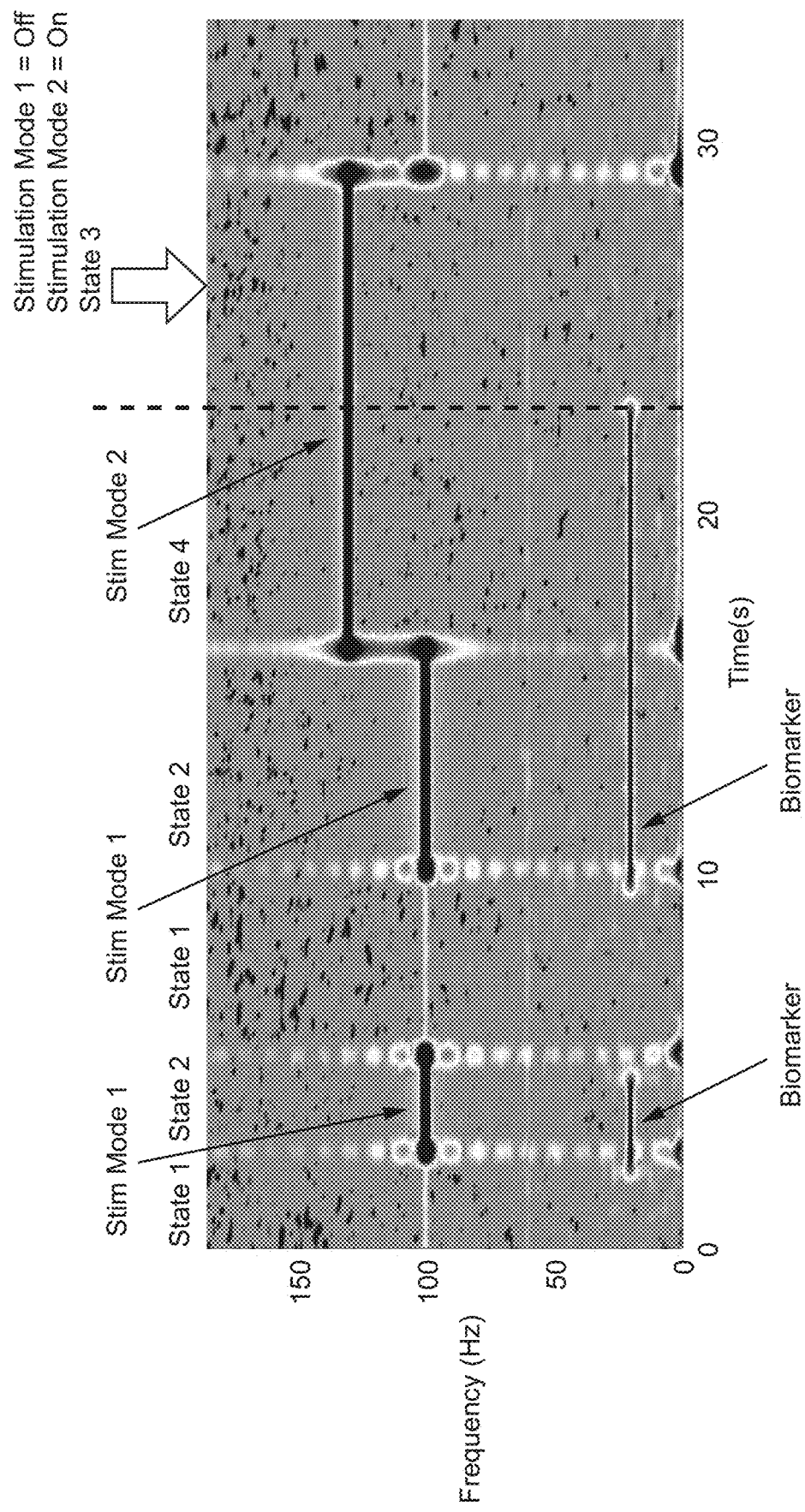
FIG. 29 is a graph illustrating an example of a spectral response during operation of multi-target adaptive neurostimulation therapy control algorithm in accordance with the example of FIG. 28.

FIG. 29 is a graph illustrating an example of a spectral response during operation of multi-target adaptive neurostimulation therapy control algorithm in accordance with the example of FIG. 28. In FIG. 29, the state 4 to state 3 transition of FIG. 28 occurs at approximately time t=23.

FIG. 30 is a table illustrating an example of the closed loop state diagram of FIG. 17 corresponding to a transition from the third state (State 3) to the first state (State 1). In state 3, LD1 detects a biomarker, and LD2 detects that stimulation is being performed. In state 3, stimulation mode 1 is off, and stimulation mode 2 is on. In response to, LD1 no longer detecting the biomarker and LD2 detecting that stimulation is being performed, IMD 16 can transition from state 3 to state 1. In state 1, stimulation mode 1 is off, and stimulation mode 2 is off. IMD 16 may, for example, perform the state 3 to state 1 transition in response to a patient's symptom being aborted or the delivery of continued stimulation otherwise being undesirable.

Figure 31:
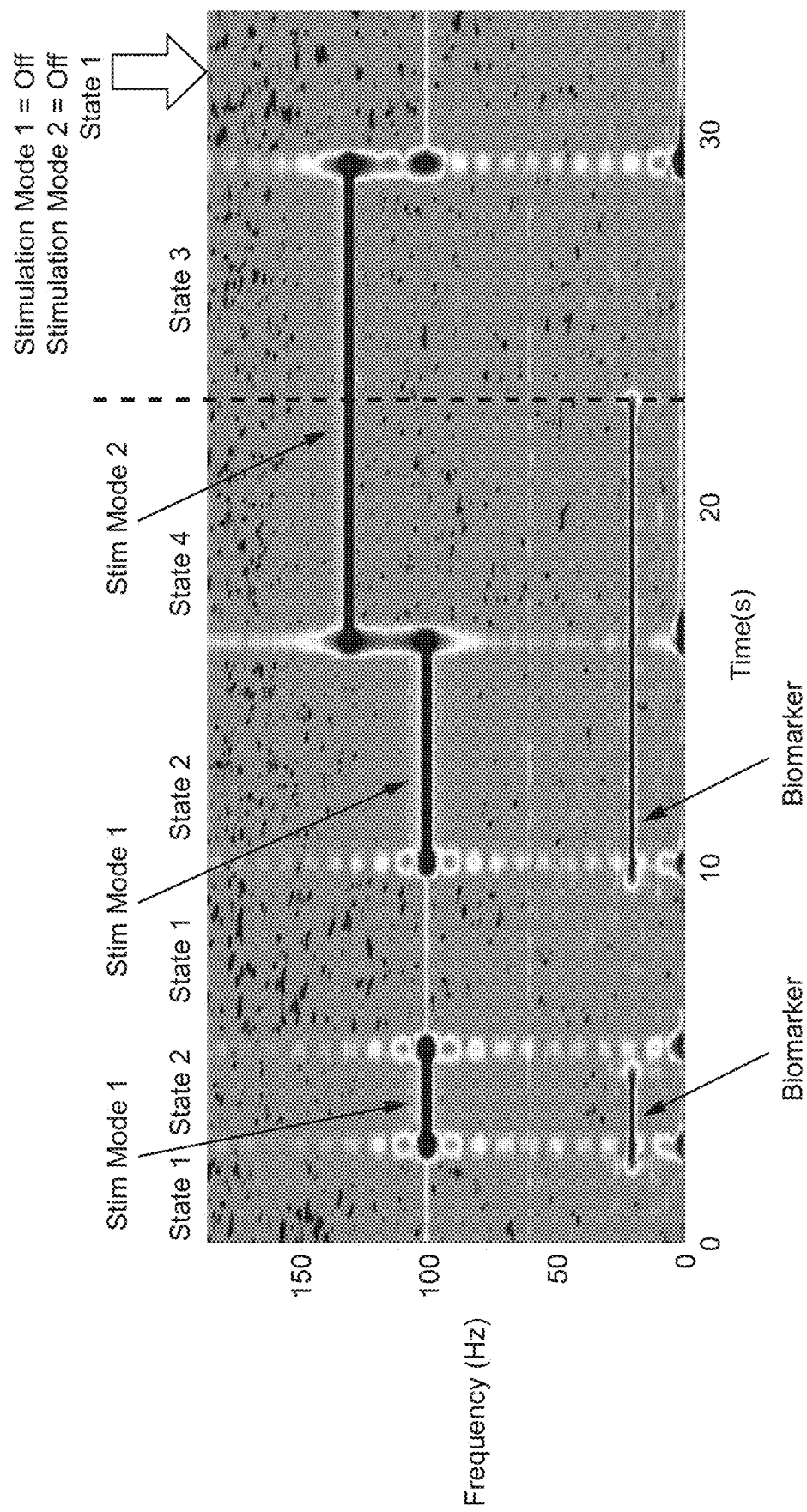
FIG. 31 is a graph illustrating an example of a spectral response during operation of multi-target adaptive neurostimulation therapy control algorithm in accordance with the example of FIG. 30.

FIG. 31 is a graph illustrating an example of a spectral response during operation of multi-target adaptive neurostimulation therapy control algorithm in accordance with the example of FIG. 30. In FIG. 31, the state 3 to state 1 transition of FIG. 30 occurs at approximately time t=30.

FIG. 32 is a table illustrating another example of a closed loop state diagram for a multi-target adaptive neurostimulation therapy control algorithm in accordance with another example of this disclosure. In one particular implementation of the techniques of this disclosure, illustrated in FIG. 32, a system including IMD 16, possibly in conjunction with a second device, may be configured to perform detection and automatic stimulation. The second device may, for example, be an external device, a second internal device, or may be the same device as IMD 16. It is desirable for IMD 16 to be able to perform detection and automatic stimulation with low latency from seizure detection to stimulation adjustment and be able to perform computation intensive classifiers for some brain states. A distributed algorithm, e.g., distributed between IMD 16 and the external device, may be better suited for handling more computationally intensive classification algorithms.

The system may be configured to classify four brain states—(1) nominal, (2) asleep, (3) pre-seizure, and (4) seizure. Of these four states, it can be expected that the seizure state requires the least computationally intensive algorithm to detect.

The system may be configured to implement a hybrid, distributed and embedded control policy that allows the system to be both low latency and computationally intensive. The distributed control policy, running on the external device, may be used to determine if the patient is in brain state 1, 2, or 3. The embedded control policy, running on IMD 16, may be configured to always be looking to detect whether the brain state is 4 or not 4. Stimulation may be configured and running in Group D (the embedded adaptive group) all of the time.

IMD 16 may include at least two detectors. A first detector (LD1) may use an on-chip linear discriminant, such that a sensed brain signal, analyzed as a weighted set of power bands, above a certain threshold, indicates a seizure. Anything else is not a seizure. A second detector (LD2) may be configured to be directly controlled by the external device. LD1 may, for example, be configured with a single threshold, such that below the threshold is not a seizure and above the threshold is a seizure (i.e., brain state 4). The power bands used in the computation on-board IMD 16 for LD1 may be selected so as to not include the desired stimulation frequency, as stimulation artifacts could then pollute the detector. Additionally, to reduce the chance of stimulation artifacts appearing on sense channels, sensing electrodes may be configured to be symmetric around stimulation electrodes.

In some examples, LD2 may be configured with dual thresholds, such that below both thresholds (low) indicates a nominal brain state, between the two thresholds (in-range) indicates an asleep brain state, and above both thresholds (high) indicates a pre-seizure brain state. In other examples, LD2 may be configured to implement a detection scheme that is more complex than the described threshold detection scheme. In fact, any number of mathematical approaches may be used, especially in examples where LD2 is processed externally and thus not subject to the size, power, and other constraints of an implantable device.

While neurological signals may be used as the input to both detectors, LD1 may be the only detector which is evaluated on IMD 16. The brain states for LD2 may be classified by the external device, and then the external device can send a command to IMD 16 indicating if LD2 should be low, in-range, or high. In this way, LD1 remains a low latency seizure detector, and LD2 utilizes the computational power of the external device.

The desired stimulation targets (e.g., amplitude and rate) for each of the described four brain states may be programmed to IMD 16, in the adaptive therapy stimulation target table. In this use case, the table may have 6 states, instead of 9, as shown in FIG. 32. When LD1 indicates a change to/from seizure, the INS stimulation may adjust accordingly, with low latency. When LD2 indicates a change to/from brain states 1, 2, or 3, again the INS stimulation may adjust accordingly, but with higher latency as the external device controls this LD.

With respect to FIG. 32, X, Y, Z and Q1, Q2, Q3 may all be different stimulation paradigms, or in some instances, Q1, Q2, and Q3 may all be the same.

Figure 33:
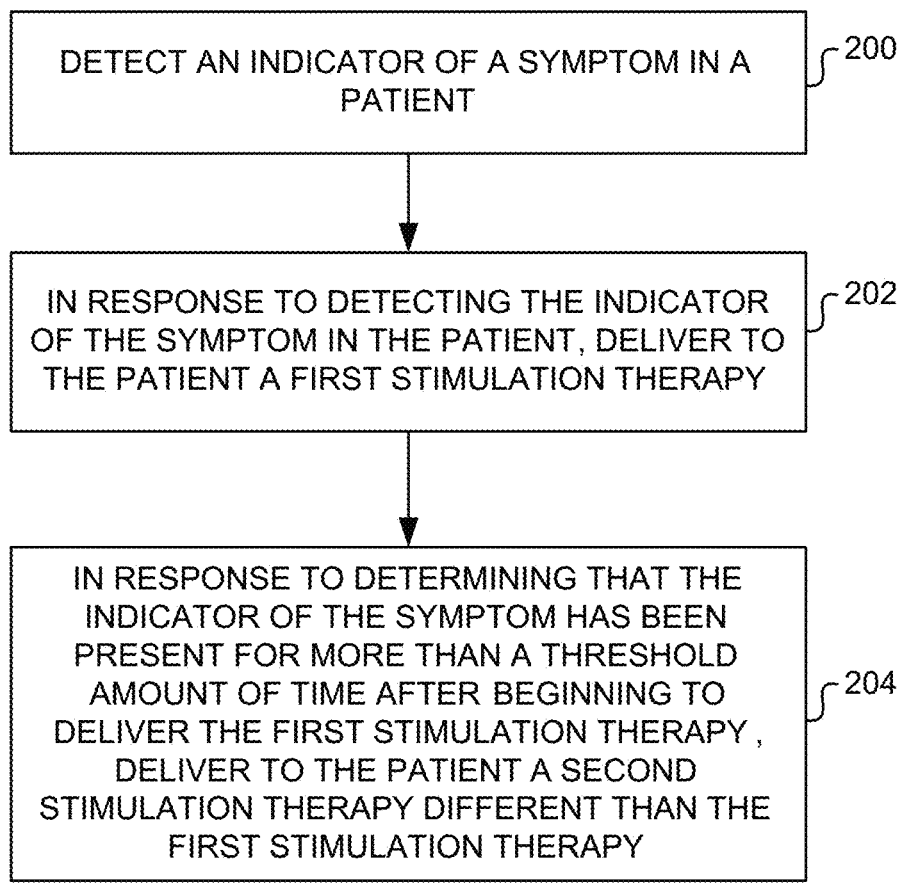
FIG. 33 is a flow diagram illustrating an example process according to techniques of this disclosure.

FIG. 33 is a flow diagram illustrating an example process according to techniques of this disclosure. The techniques of FIG. 33 will be described with respect to IMD 16 but may also be performed by other devices or systems of devices.

IMD 16 may execute a state-machine runtime environment that is configurable to implement a state machine based on programmable state parameters. IMD 16 may control delivery of therapy to the patient based on the state machine. The state machine may, for instance, generate one or more therapy decisions to control the delivery of the therapy based on one or more sensed states of the patient. The state machine may have a structure that is defined at least in part by the one or more programmable state parameters.

In the example of FIG. 33, IMD 16 detects an indicator of a symptom in a patient (200). IMD 16 may, for example detect the indicator of the symptom in the patient by detecting a presence of a biomarker in the patient. The biomarker may, for example, be one or both of a measure of electrical activity or a measure of patient movement.

In response to detecting the indicator of the symptom in the patient, IMD 16 delivers to the patient a first stimulation therapy (202). IMD 16 may deliver the first stimulation therapy in response to determining that the first stimulation therapy is not being delivered. IMD 16 may, for example, determine that the first stimulation therapy is not being delivered based on a control state of control logic in IMD 16 or based on detecting (or not detecting) electrical signals within the patient.

In response to determining that the indicator of the symptom has been present for more than a threshold amount of time after beginning to deliver the first stimulation therapy, IMD 16 delivers to the patient a second stimulation therapy different than the first stimulation therapy (204). In some examples, in response to determining that the indicator of the symptom has been present for more than the threshold amount of time after beginning to deliver the first stimulation therapy, IMD 16 may terminate the delivery of the first stimulation therapy. In other examples, IMD 16 may deliver the second stimulation therapy concurrently with the first stimulation therapy. To determine that the indicator of the symptom has been present for more than the threshold amount of time after beginning to deliver the first stimulation therapy, IMD 16 may, for example, detect the presence of a biomarker in the patient after more than the threshold amount of time after beginning to deliver the first stimulation therapy.

IMD 16 may deliver the first stimulation therapy to a first target area and deliver the second stimulation therapy to a second target area of the patient that is different than the first target area. The first target area may, for example, be a first area in the brain of the patient, and the second target area may be a second area in the brain of the patient. IMD 16 may deliver the first stimulation therapy to the patient via implantable electrodes and also deliver the second stimulation therapy via the implantable electrodes. In other examples, IMD 16 may deliver the first stimulation therapy to the first target area of the patient via a first set of one or more electrodes and deliver the second stimulation therapy to the second target area of the patient via a second set of one or more electrodes, with at least one electrode of the second set being different than the one or more electrodes of the first set. The first and/or second stimulation therapy may be delivered via one or more electrodes in a temporal lobe of the brain. The temporal lobe may, for example, be one of a amygdala, a hippocampus, one or more fields of the hippocampus, a CA region, a subiculum, a dentate gyms, or an entorhinal cortex.

In some examples, in response to determining that the indicator of the symptom has been present for more than a threshold amount of time after beginning to deliver the second stimulation therapy, IMD 16 may stop delivering the second stimulation therapy. In other examples, in response to determining that the indicator of the symptom has been present for more than a threshold amount of time after beginning to deliver the second stimulation therapy, IMD 16 may deliver third stimulation therapy.

At least one of a frequency, a pulse width, or an amplitude for the first stimulation therapy may be different than a frequency, a pulse width, or an amplitude for the second stimulation therapy. In some examples, the first stimulation therapy may be a first deep brain stimulation therapy, and second stimulation therapy may be a second deep brain stimulation therapy. The first stimulation therapy and the second stimulation therapy may each be therapies to alleviate symptoms of at least one of Parkinson's disease, Tourette's syndrome, spasticity, epilepsy, essential tremor, dyskinesia, or dystonia.

In some examples, the first target area and the second target area may be within a circuit of Papez of the brain. The circuit of Papez includes an anterior nucleus of a thalamus, an internal capsule, a cingulate, a hippocampus, a fornix, an entorhinal cortex, mammillary bodies, and a mammillothalamic tract. In some examples, the first target area may be an anterior nucleus, and the second target area may be a hippocampus of the brain. In some examples, the first target area may be one of a subthalamic nucleus or an internal globus pallidus, and the second target area may be one of a motor cortex (M1) or a primary motor cortex. In some examples, the first target area may include a ventral intermediate nucleus of thalamus, and the second target area may include a ventralis oralis.

The following examples are examples of the devices and techniques described above.

Example 1: A method that includes detecting an indicator of a symptom in a patient; in response to detecting the indicator of the symptom in the patient, delivering to the patient by an implantable medical device (IMD), a first stimulation therapy; and in response to determining that the indicator of the symptom has been present for more than a threshold amount of time after beginning to deliver the first stimulation therapy, delivering to the patient by the IMD, a second stimulation therapy different than the first stimulation therapy.

Example 2: The method of example 1, wherein detecting the indicator of the symptom in the patient comprises detecting a presence of a biomarker in the patient.

Example 3: The method of example 2, wherein the biomarker comprises a measure of electrical activity.

Example 4: The method of example 2, wherein the biomarker comprises a measure of patient movement.

Example 5: The method of any of examples 1-4, wherein determining that the indicator of the symptom has been present for more than the threshold amount of time after beginning to deliver the first stimulation therapy comprises detecting the presence of a biomarker in the patient after more than the threshold amount of time after beginning to deliver the first stimulation therapy.

Example 6: The method of any of examples 1-5, wherein delivering the first stimulation therapy comprises delivering the first stimulation therapy to a first target area of the patient and wherein delivering the second stimulation therapy comprises delivering the second stimulation therapy to a second target area of the patient, wherein the second target area is different than the first target area.

Example 7: The method of example 6, wherein the first target area comprises a first area in the brain of the patient and the second target area comprises a second area in the brain of the patient.

Example 8: The method of example 6, wherein delivering the first stimulation therapy to the first target area of the patient comprises delivering the first stimulation therapy via a first set of one or more electrodes and delivering the second stimulation therapy to the second target area of the patient comprises delivering the second stimulation therapy via a second set of one or more electrodes, wherein at least one electrode of the second set is different than the one or more electrodes of the first set.

Example 9: The method of example 1, further that includes in response to determining that the indicator of the symptom has been present for more than the threshold amount of time after beginning to deliver the first stimulation therapy, terminating the delivery of the first stimulation therapy.

Example 10: The method of example 1, further that includes delivering, to the patient by the IMD, the second stimulation therapy concurrently with the first stimulation therapy.

Example 11: The method of example 1, further that includes in response to determining that the indicator of the symptom has been present for more than a threshold amount of time after beginning to deliver the second stimulation therapy, stopping delivery of the second stimulation therapy.

Example 12: The method of example 1, further that includes in response to determining that the indicator of the symptom has been present for more than a threshold amount of time after beginning to deliver the second stimulation therapy, delivering to the patient by the IMD, a third stimulation therapy.

Example 13: The method of example 1, wherein delivering the first stimulation therapy is performed further in response to determining that the first stimulation therapy is not being delivered.

Example 14: The method of example 13, wherein determining that the first stimulation therapy is not being delivered comprises determining that the first stimulation therapy is not being delivered based on a control state of control logic in the IMD.

Example 15: The method of example 13, wherein determining that the first stimulation therapy is not being delivered comprises determining that the first stimulation therapy is not being delivered based on detecting electrical signals within the patient.

Example 16: The method of any of examples 1-15, wherein at least one of a frequency, a pulse width, or an amplitude for the first stimulation therapy is different than a frequency, a pulse width, or an amplitude for the second stimulation therapy.

Example 17: The method of any of examples 1-16, wherein the first stimulation therapy comprises first deep brain stimulation therapy and wherein the second stimulation therapy comprises second deep brain stimulation therapy.

Example 18: The method of any of examples 1-17, wherein the first stimulation therapy and the second stimulation therapy each comprise a therapy configured to alleviate symptoms of at least one of Parkinson's disease, Tourette's syndrome, spasticity, epilepsy, essential tremor, dyskinesia, or dystonia.

Example 19: The method of any of examples 1-18, wherein delivering to the patient the first stimulation therapy comprises delivering the first stimulation therapy to the patient via implantable electrodes and delivering to the patient the second stimulation therapy comprises delivering the second stimulation therapy to the patient via the implantable electrodes.

Example 20: The method of any of examples 1-19, further that includes executing a state-machine runtime environment by the IMD, wherein the state-machine runtime environment is configurable to implement a state machine based on programmable state parameters; and controlling delivery of therapy by the IMD to the patient based on the state machine, wherein the state machine generates one or more therapy decisions to control the delivery of the therapy based on one or more sensed states of the patient, the state machine having a structure that is defined at least in part by the one or more programmable state parameters.

Example 21: The method of any of examples 6-20, wherein the first target area and the second target area are within a circuit of Papez of the brain.

Example 22: The method of example 21, wherein the circuit of Papez includes an anterior nucleus of a thalamus, an internal capsule, a cingulate, a hippocampus, a fornix, an entorhinal cortex, mammillary bodies, and a mammillothalamic tract.

Example 23: The method of any of examples 6-20, wherein the first target area comprises an anterior nucleus and the second target area comprises a hippocampus of the brain.

Example 24: The method of any of examples 6-20, wherein the first target area comprises one of a subthalamic nucleus or an internal globus pallidus, and the second target area comprises one of a motor cortex (M1) or a primary motor cortex.

Example 25: The method of any of examples 6-20, wherein the first target area comprises ventral intermediate nucleus of thalamus, and the second target area comprises a ventralis oralis.

Example 26: The method of any of examples 1-25, wherein the second stimulation therapy is delivered via an electrode in a temporal lobe of the brain.

Example 27: The method of example 26, wherein the electrode in the temporal lobe is at one of a amygdala, a hippocampus, one or more fields of the hippocampus, a CA region, a subiculum, a dentate gyms, or an entorhinal cortex.

Example 28: A medical device system for therapy deliver that includes stimulation circuitry; and processing circuitry configured to: detect an indicator of a symptom in a patient; in response to detecting the indicator of the symptom in the patient, deliver to the patient, by the stimulation circuitry, a first stimulation therapy; and in response to determining that the indicator of the symptom has been present for more than a threshold amount of time after beginning to deliver the first stimulation therapy, deliver to the patient, by the stimulation circuitry, a second stimulation therapy different than the first stimulation therapy.

Example 29: The system of example 28, wherein to detect the indicator of the symptom in the patient, the processing circuitry is configured to detect a presence of a biomarker in the patient.

Example 30: The system of example 29, wherein the biomarker comprises a measure of electrical activity.

Example 31: The system of example 29, wherein the biomarker comprises a measure of patient movement.

Example 32: The system of any of examples 28-31, wherein to determine that the indicator of the symptom has been present for more than the threshold amount of time after beginning to deliver the first stimulation therapy, the processing circuitry is configured to detect the presence of a biomarker in the patient after more than the threshold amount of time after beginning to deliver the first stimulation therapy.

Example 33: The system of any of examples 28-32, wherein to deliver the first stimulation therapy, the processing circuitry is configured to deliver the first stimulation therapy to a first target area of the patient and wherein delivering the second stimulation therapy comprises delivering the second stimulation therapy to a second target area of the patient, wherein the second target area is different than the first target area.

Example 34: The system of example 33, wherein the first target area comprises a first area in the brain of the patient and the second target area comprises a second area in the brain of the patient.

Example 35: The system of example 33, wherein to deliver the first stimulation therapy to the first target area of the patient, the processing circuitry is configured to deliver the first stimulation therapy via a first set of one or more electrodes, and wherein to deliver the second stimulation therapy to the second target area of the patient, the processing circuitry is configured to deliver the second stimulation therapy via a second set of one or more electrodes, wherein at least one electrode of the second set is different than the one or more electrodes of the first set.

Example 36: The system of example 28, wherein the processing circuitry is further configured to: in response to determining that the indicator of the symptom has been present for more than the threshold amount of time after beginning to deliver the first stimulation therapy, terminate the delivery of the first stimulation therapy.

Example 37: The system of example 28, wherein the processing circuitry is further configured to: deliver, to the patient by the stimulation circuitry, the second stimulation therapy concurrently with the first stimulation therapy.

Example 38: The system of example 28, wherein the processing circuitry is further configured to: in response to determining that the indicator of the symptom has been present for more than a threshold amount of time after beginning to deliver the second stimulation therapy, stop delivery of the second stimulation therapy.

Example 39: The system of example 28, wherein the processing circuitry is further configured to: in response to determining that the indicator of the symptom has been present for more than a threshold amount of time after beginning to deliver the second stimulation therapy, deliver to the patient by the stimulation circuitry, a third stimulation therapy.

Example 40: The system of example 28, wherein the processing circuitry is further configured to deliver the first stimulation therapy in response to determining that the first stimulation therapy is not being delivered.

Example 41: The system of example 40, wherein to determine that the first stimulation therapy is not being delivered, the processing circuitry is further configured to determine that the first stimulation therapy is not being delivered based on a control state of control logic.

Example 42: The system of example 40, wherein to determine that the first stimulation therapy is not being delivered, the processing circuitry is further configured to determine that the first stimulation therapy is not being delivered based on detecting electrical signals within the patient.

Example 43: The system of any of examples 28-42, wherein at least one of a frequency, a pulse width, or an amplitude for the first stimulation therapy is different than a frequency, a pulse width, or an amplitude for the second stimulation therapy.

Example 44: The system of any of examples 28-43, wherein the first stimulation therapy comprises first deep brain stimulation therapy and wherein the second stimulation therapy comprises second deep brain stimulation therapy.

Example 45: The system of any of examples 28-44, wherein the first stimulation therapy and the second stimulation therapy each comprise a therapy configured to alleviate symptoms of at least one of Parkinson's disease, Tourette's syndrome, spasticity, epilepsy, essential tremor, dyskinesia, or dystonia.

Example 46: The system of any of examples 28-45, wherein the processing circuitry is further configured to deliver to the patient the first stimulation therapy via implantable electrodes and deliver to the patient the second stimulation therapy via the implantable electrodes.

Example 47: The system of any of examples 28-46, wherein the processing circuitry is further configured to: execute a state-machine runtime environment by the IMD, wherein the state-machine runtime environment is configurable to implement a state machine based on programmable state parameters; and control delivery of therapy by the IMD to the patient based on the state machine, wherein the state machine generates one or more therapy decisions to control the delivery of the therapy based on one or more sensed states of the patient, the state machine having a structure that is defined at least in part by the one or more programmable state parameters.

Example 48: The system of any of examples 33-47, wherein the first target area and the second target area are within a circuit of Papez of the brain.

Example 49: The system of example 48, wherein the circuit of Papez includes an anterior nucleus of a thalamus, an internal capsule, a cingulate, a hippocampus, a fornix, an entorhinal cortex, mammillary bodies, and a mammillothalamic tract.

Example 50: The system of any of examples 33-47, wherein the first target area comprises an anterior nucleus and the second target area comprises a hippocampus of the brain.

Example 51: The system of any of examples 33-47, wherein the first target area comprises one of a subthalamic nucleus or an internal globus pallidus, and the second target area comprises one of a motor cortex (M1) or a primary motor cortex.

Example 52: The system of any of examples 33-47, wherein the first target area comprises ventral intermediate nucleus of thalamus, and the second target area comprises a ventralis oralis.

Example 53: The system of any of examples 28-52, wherein the second stimulation therapy is delivered via an electrode in a temporal lobe of the brain.

Example 54: The system of example 53, wherein the electrode in the temporal lobe is at one of an amygdala, a hippocampus, one or more fields of the hippocampus, a CA region, a subiculum, a dentate gyrus, or an entorhinal cortex.

Example 55: The system of any of examples 28-54, wherein the stimulation circuitry and the processing circuitry are included in a single implantable medical device.

Example 56: The system of any of examples 28-54, wherein the processing circuitry comprises first processing circuitry within a first implantable medical device and second processing circuitry within a second medical device.

Example 57: The system of example 56, wherein the stimulation circuitry is wholly within the first implantable medical device.

Example 58: The system of example 56, the stimulation circuitry comprises first stimulation circuitry within the first implantable medical device and second stimulation circuitry within the second medical device.

Example 59: A computer-readable medium storing instructions that when executed by one or more medical devices cause the one or more medical devices to: detect an indicator of a symptom in a patient; in response to detecting the indicator of the symptom in the patient, deliver to the patient a first stimulation therapy; and in response to determining that the indicator of the symptom has been present for more than a threshold amount of time after beginning to deliver the first stimulation therapy, deliver to the patient a second stimulation therapy different than the first stimulation therapy.

Example 60 A system that includes means for detecting an indicator of a symptom in a patient; means for delivering to the patient a first stimulation therapy in response to detecting the indicator of the symptom in the patient; and means for delivering to the patient a second stimulation therapy different than the first stimulation therapy in response to determining that the indicator of the symptom has been present for more than a threshold amount of time after beginning to deliver the first stimulation therapy.

Although the examples in this disclosure have been described with respect to using programmable state machines to control the delivery of therapy based on sensed states of a patient, in other examples, the programmable state machines may be used for other purposes in addition to or in lieu of controlling the delivery of therapy based on sensed states of a patient. For examples, similar types of programmable state machines may be used to provide "closed loop sensing" where the state machine determines what to sense and/or what control parameters to use for various sensors based on one or more sensed states of a patient. Other examples are also possible.

The techniques described in this disclosure may be implemented, at least in part, in hardware, software, firmware or any combination thereof. For example, various aspects of the techniques may be implemented within one or more microprocessors, digital signal processors (DSPs), application specific integrated circuits (ASICs), field programmable gate arrays (FPGAs), or any other equivalent integrated or discrete logic circuitry, as well as any combinations of such components, implemented in programmers, such as physician or patient programmers, stimulators, or other devices. The terms "processor," "processing circuitry," "controller" or "control module" may generally refer to any of the foregoing logic circuitry, alone or in combination with other logic circuitry, or any other equivalent circuitry, and alone or in combination with other digital or analog circuitry.

For aspects implemented in software, at least some of the functionality ascribed to the systems and devices described in this disclosure may be implemented as instructions on a computer-readable medium such as RAM, ROM, NVRAM, EEPROM, FLASH memory, magnetic media, optical media, or the like. The instructions may be executed to support one or more aspects of the functionality described in this disclosure.

Various examples of the disclosure have been described. These and other examples are within the scope of the following claims.

What is claimed is:

1. A medical device system for therapy delivery, the system comprising:
   a housing configured to be implanted in a patient;
   stimulation circuitry at least partially enclosed in the housing; and
   processing circuitry contained within the housing and configured to:
      while not providing any stimulation therapy to a patient, monitor the patient to detect an indicator of a symptom;
      in response to detecting the indicator of the symptom in the patient, cause the stimulation circuitry to deliver to the patient a first stimulation therapy to a first target area of the patient;
      determine that the indicator of the symptom has been present for more than a threshold amount of time after beginning to deliver the first stimulation therapy; and
      in response to determining that the indicator of the symptom has been present for more than the threshold amount of time after beginning to deliver the first stimulation therapy, automatically cause the stimulation circuitry to deliver to the patient a second stimulation therapy to a second target area that is different than the first target area.

2. The system of claim 1, further comprising:
   a bioelectrical sensor;
   wherein to monitor the patient to detect the indicator of the symptom, the processing circuitry is configured to monitor the patient for a presence of a biomarker based on a signal received from the bioelectrical sensor;
   wherein to detect the indicator of the symptom in the patient, the processing circuitry is configured to detect the presence of a biomarker in the patient based on a change in the signal received from the bioelectrical sensor.

3. The system of claim 2, wherein to determine that the indicator of the symptom has been present for more than the threshold amount of time after beginning to deliver the first stimulation therapy, the processing circuitry is configured to detect the presence of the biomarker in the patient after more than the threshold amount of time after beginning to deliver the first stimulation therapy.

4. The system of claim 2, wherein the processing circuitry is further configured to:
   detect a second change in the signal received from the bioelectrical sensor; and
   in response to detecting the second change in the signal received from the bioelectrical sensor, automatically cause the stimulation circuitry to deliver to the patient the second stimulation therapy to the second target area.

5. The system of claim 1, wherein the first target area comprises a first area in the brain of the patient and the second target area comprises a second area in the brain of the patient.

6. The system of claim 1, wherein to deliver the first stimulation therapy to the first target area of the patient, the processing circuitry is configured to deliver the first stimulation therapy via a first set of one or more electrodes, and wherein to deliver the second stimulation therapy to the second target area of the patient, the processing circuitry is configured to deliver the second stimulation therapy via a second set of one or more electrodes, wherein at least one electrode of the second set is different than the one or more electrodes of the first set.

7. The system of claim 1, wherein the first target area comprises an anterior nucleus and the second target area comprises a hippocampus of the brain.

8. The system of claim 1, wherein the first target area comprises one of a subthalamic nucleus or an internal globus pallidus, and the second target area comprises one of a motor cortex (M1) or a primary motor cortex.

9. The system of claim 1, wherein the first target area comprises ventral intermediate nucleus of thalamus, and the second target area comprises a ventralis oralis.

10. The system of claim 1, wherein the first target area and the second target area are within a circuit of Papez of the brain.

11. The system of claim 10, wherein the circuit of Papez includes an anterior nucleus of a thalamus, an internal capsule, a cingulate, a hippocampus, a fornix, an entorhinal cortex, mammillary bodies, and a mammillothalamic tract.

12. The system of claim 1, wherein the processing circuitry is further configured to:
   in response to determining that the indicator of the symptom has been present for more than the threshold amount of time after beginning to deliver the first stimulation therapy, terminate the delivery of the first stimulation therapy.

13. The system of claim 1, wherein the processing circuitry is further configured to:
   cause the stimulation circuitry to deliver, to the patient, the second stimulation therapy concurrently with the first stimulation therapy.

14. The system of claim 1, wherein the processing circuitry is further configured to:
in response to determining that the indicator of the symptom has been present for more than a threshold amount of time after beginning to deliver the second stimulation therapy, stop delivery of the second stimulation therapy.

15. The system of claim 1, wherein the processing circuitry is further configured to:
in response to determining that the indicator of the symptom has been present for more than a threshold amount of time after beginning to deliver the second stimulation therapy, cause the stimulation circuitry to deliver to the patient a third stimulation therapy.

16. The system of claim 1, wherein the processing circuitry is further configured to deliver the first stimulation therapy in response to determining that the first stimulation therapy is not being delivered.

17. The system of claim 16, wherein to determine that the first stimulation therapy is not being delivered, the processing circuitry is further configured to determine that the first stimulation therapy is not being delivered based on a control state of control logic.

18. The system of claim 16, wherein to determine that the first stimulation therapy is not being delivered, the processing circuitry is further configured to determine that the first stimulation therapy is not being delivered based on detecting electrical signals within the patient.

19. The system of claim 1, wherein at least one of a frequency, a pulse width, or an amplitude for the first stimulation therapy is different than a frequency, a pulse width, or an amplitude for the second stimulation therapy.

20. The system of claim 1, wherein the first stimulation therapy comprises first deep brain stimulation therapy and wherein the second stimulation therapy comprises second deep brain stimulation therapy.

21. The system of claim 1, wherein the first stimulation therapy and the second stimulation therapy each comprise a therapy configured to alleviate symptoms of at least one of Parkinson's disease, Tourette's syndrome, spasticity, epilepsy, essential tremor, dyskinesia, or dystonia.

22. The system of claim 1, wherein the processing circuitry is further configured to deliver to the patient the first stimulation therapy via implantable electrodes and deliver to the patient the second stimulation therapy via the implantable electrodes.

23. The system of claim 1, wherein the processing circuitry is further configured to:
execute a state-machine runtime environment, wherein the state-machine runtime environment is configurable to implement a state machine based on programmable state parameters; and
control delivery of therapy to the patient based on the state machine, wherein the state machine generates one or more therapy decisions to control the delivery of the therapy based on one or more sensed states of the patient, the state machine having a structure that is defined at least in part by the one or more programmable state parameters.

24. The system of claim 1, further comprising an electrode configured to deliver the second stimulation therapy to a temporal lobe of the brain.

25. The system of claim 24, wherein the electrode is configured to deliver the second stimulation therapy at one of an amygdala, a hippocampus, one or more fields of the hippocampus, a CA region, a subiculum, a dentate gyrus, or an entorhinal cortex.

26. The system of claim 1, wherein the processing circuitry is configured to execute a closed-loop algorithm while the housing is implanted in the patient, wherein the closed loop algorithm causes the processing circuitry to:
in response to determining that the indicator of the symptom has been present for more than the threshold amount of time after beginning to deliver the first stimulation therapy, automatically cause the stimulation circuitry to deliver to the patient a second stimulation therapy to the second target area that is different than the first target area.

27. A method comprising:
while not providing any stimulation therapy to a patient, monitoring, by an implantable medical device (IMD), the patient to detect an indicator of a symptom;
in response to detecting the indicator of the symptom in the patient, delivering to the patient, by the IMD, a first stimulation therapy to a first target area of the patient;
determining, by the IMD, that the indicator of the symptom has been present for more than a threshold amount of time after beginning to deliver the first stimulation therapy; and
in response to determining that the indicator of the symptom has been present for more than the threshold amount of time after beginning to deliver the first stimulation therapy, automatically delivering to the patient by the IMD, a second stimulation therapy to a second target area that is different than the first target area.

28. The method of claim 27, wherein detecting the indicator of the symptom in the patient comprises detecting a presence of a biomarker in the patient.

29. The method of claim 28, wherein determining that the indicator of the symptom has been present for more than the threshold amount of time after beginning to deliver the first stimulation therapy comprises detecting the presence of the biomarker in the patient after more than the threshold amount of time after beginning to deliver the first stimulation therapy.

30. The method of claim 27, wherein delivering the first stimulation therapy is performed further in response to determining that the first stimulation therapy is not being delivered.

31. The method of claim 27, wherein at least one of a frequency, a pulse width, or an amplitude for the first stimulation therapy is different than a frequency, a pulse width, or an amplitude for the second stimulation therapy.

32. The method of claim 27, wherein the first stimulation therapy comprises first deep brain stimulation therapy and wherein the second stimulation therapy comprises second deep brain stimulation therapy.

33. The method of claim 27, wherein the first stimulation therapy and the second stimulation therapy each comprise a therapy configured to alleviate symptoms of at least one of Parkinson's disease, Tourette's syndrome, spasticity, epilepsy, essential tremor, dyskinesia, or dystonia.

34. The method of claim 27, further comprising:
executing a state-machine runtime environment by the IMD, wherein the state-machine runtime environment is configurable to implement a state machine based on programmable state parameters; and
controlling delivery of therapy by the IMD to the patient based on the state machine, wherein the state machine generates one or more therapy decisions to control the delivery of the therapy based on one or more sensed states of the patient, the state machine having a structure that is defined at least in part by the one or more programmable state parameters.

35. A non-transitory computer-readable medium storing instructions that when executed by one or more processors of an implantable medical device (IMD) cause the IMD to:
while not providing any stimulation therapy to a patient, monitor the patient to detect an indicator of a symptom;
in response to detecting the indicator of the symptom in the patient, deliver to the patient a first stimulation therapy to a first target area of the patient;
determine that the indicator of the symptom has been present for more than a threshold amount of time after beginning to deliver the first stimulation therapy; and
in response to determining that the indicator of the symptom has been present for more than the threshold amount of time after beginning to deliver the first stimulation therapy, automatically deliver to the patient a second stimulation therapy to a second target area that is different than the first target area.

\* \* \* \* \*